US011517464B2

(12) United States Patent
Decker et al.

(10) Patent No.: US 11,517,464 B2
(45) Date of Patent: *Dec. 6, 2022

(54) REDUCTION SPLINT FOR EDENTULOUS PATIENTS

(71) Applicants: Summer Joy Decker, Tampa, FL (US); Jonathan Michael Ford, Tampa, FL (US); Jessica Allen Ching, Tampa, FL (US)

(72) Inventors: Summer Joy Decker, Tampa, FL (US); Jonathan Michael Ford, Tampa, FL (US); Jessica Allen Ching, Tampa, FL (US)

(73) Assignee: University of South Florida, Tampa, FL (US)

( * ) Notice: Subject to any disclaimer, the term of this patent is extended or adjusted under 35 U.S.C. 154(b) by 991 days.

This patent is subject to a terminal disclaimer.

(21) Appl. No.: 16/252,868

(22) Filed: Jan. 21, 2019

(65) Prior Publication Data
US 2019/0159923 A1 May 30, 2019

Related U.S. Application Data

(63) Continuation of application No. PCT/US2017/044863, filed on Aug. 1, 2017, which is
(Continued)

(51) Int. Cl.
*G06T 15/00* (2011.01)
*A61F 5/058* (2006.01)
(Continued)

(52) U.S. Cl.
CPC ........ *A61F 5/05891* (2013.01); *A61B 17/663* (2013.01); *A61B 34/10* (2016.02);
(Continued)

(58) Field of Classification Search
CPC ... A61F 5/05891; A61C 5/007; A61C 9/0046; A61C 7/08; A61C 7/002;
(Continued)

(56) References Cited

U.S. PATENT DOCUMENTS 6,086,365 A 7/2000 Fields
6,227,861 B1 5/2001 Cartledge et al.
(Continued)

OTHER PUBLICATIONS

Chen X, Li X, Xu L, Sun Y, Politis C, Egger J. Development of a computer-aided design software for dental splint in orthognathic surgery. Scientific Reports. Dec. 14, 2016;6(1):1-0.*
(Continued)

*Primary Examiner* — Phu K Nguyen
(74) *Attorney, Agent, or Firm* — Nicholas Pfeifer; Smith & Hopen, P. A.

(57) ABSTRACT

An off-the-shelf oral splint that is operatively secured to the maxilla and mandible to assist in reduction and provide maintenance of reduction of maxillary and mandibular fractures in the edentulous or partially edentulous patient. The oral splint is fabricated into a plurality of standardized sizes. These sizes are determined by imaging a population of jaws, measuring dimensions thereof, manipulating (e.g., calculating the mean) these dimensions, and generating a size that is representative of a subset of that population. This can be done for all sizes that would represent individuals in that population. The splint itself is fabricated virtually by creating "U-shapes", splitting them horizontally into halves, creating an evacuation channel, and generating a coupling mechanism to hold the halves together. The splint can then be printed or otherwise manufactured.

20 Claims, 53 Drawing Sheets

Related U.S. Application Data a continuation-in-part of application No. 15/244,249, filed on Aug. 23, 2016, now abandoned, which is a continuation of application No. PCT/US2015/017126, filed on Feb. 23, 2015.

(60) Provisional application No. 61/943,636, filed on Feb. 24, 2014, provisional application No. 62/369,413, filed on Aug. 1, 2016.

(51) Int. Cl.

| | |
|---|---|
| *A61C 9/00* | (2006.01) |
| *G06T 17/20* | (2006.01) |
| *A61B 17/66* | (2006.01) |
| *A61B 34/10* | (2016.01) |
| *B33Y 80/00* | (2015.01) |
| *B33Y 50/00* | (2015.01) |
| *B29C 64/386* | (2017.01) |
| *G05B 19/4099* | (2006.01) |
| *A61C 5/00* | (2017.01) |
| *G06T 19/00* | (2011.01) |
| *A61C 7/08* | (2006.01) |
| *A61C 7/00* | (2006.01) |
| *A61B 17/00* | (2006.01) |
| *A61B 17/56* | (2006.01) |
| *B33Y 10/00* | (2015.01) |

(52) U.S. Cl.
CPC .............. *A61C 5/007* (2013.01); *A61C 7/002* (2013.01); *A61C 7/08* (2013.01); *A61C 9/0046* (2013.01); *B29C 64/386* (2017.08); *B33Y 50/00* (2014.12); *B33Y 80/00* (2014.12); *G05B 19/4099* (2013.01); *G06T 17/20* (2013.01); *G06T 19/00* (2013.01); *A61B 2017/00526* (2013.01); *A61B 2017/564* (2013.01); *B33Y 10/00* (2014.12); *G05B 2219/35134* (2013.01); *G05B 2219/49007* (2013.01); *G06T 2210/41* (2013.01)

(58) Field of Classification Search
CPC ........ A61B 2017/00526; A61B 17/663; A61B 2017/564; A61B 34/10; G06T 19/00; G06T 2210/41; G06T 17/20; G05B 2219/35134; G05B 19/4099; G05B 2219/49007; B33Y 10/00; B33Y 80/00; B33Y 50/00; B29C 64/386
USPC .......................................................... 345/418
See application file for complete search history.

(56) References Cited

U.S. PATENT DOCUMENTS

| | | | |
|---|---|---|---|
| 6,671,539 B2 | 12/2003 | Gateno et al. | |
| 8,246,663 B2 | 8/2012 | Lovald et al. | |
| 8,282,635 B1 | 10/2012 | Amato | |
| 9,192,505 B2* | 11/2015 | Decker | A61C 5/007 |
| 2007/0074729 A1 | 4/2007 | Magnin | |
| 2011/0166572 A1 | 7/2011 | Ihde | |
| 2012/0028221 A1* | 2/2012 | Williams | A61C 5/007 |
| | | | 433/215 |
| 2012/0214121 A1 | 8/2012 | Greenberg | |
| 2013/0310963 A1 | 11/2013 | Davidson | |
| 2015/0083140 A1* | 3/2015 | Youngman | A61C 7/36 |
| | | | 264/16 |
| 2015/0238345 A1* | 8/2015 | Decker | A61C 5/007 |
| | | | 382/128 |
| 2016/0184129 A1* | 6/2016 | Liptak | A61C 7/08 |
| | | | 128/848 |
| 2016/0354227 A1* | 12/2016 | Decker | G06T 17/20 |
| 2016/0378883 A1* | 12/2016 | Lucas | A61F 5/566 |
| | | | 703/1 |
| 2018/0024530 A1* | 1/2018 | Kim | A61F 5/56 |
| | | | 128/848 |
| 2018/0078344 A1* | 3/2018 | Falkel | A61C 7/36 |
| 2019/0159923 A1* | 5/2019 | Decker | A61C 7/002 |
| 2022/0087793 A1* | 3/2022 | Sisson | B33Y 80/00 |

OTHER PUBLICATIONS

Gholampour S, Gholampour H, Khanmohammadi H. Finite element analysis of occlusal splint therapy in patients with bruxism. BMC oral health. Dec. 2019;19(1):1-9.*

Pojda D, Tomaka AA, Luchowski L, Skabek K, Tarnawski M. Applying computational geometry to designing an occlusal splint. InInternational Symposium Computational Modeling of Objects Represented in Images Jul. 2, 2018 (pp. 186-200). Springer, Cham.*

Salmi M, Tuomi J, Sirkkanen R, Ingman T, Mäkitie A. Rapid tooling method for soft customized removable oral appliances. The open dentistry journal. 2012;6:85.*

Ye N, Wu T, Dong T, Yuan L, Fang B, Xia L. Precision of 3D-printed splints with different dental model offsets. American Journal of Orthodontics and Dentofacial Orthopedics. May 1, 2019;155(5):733-8.*

Wang S, Li Z, Ye H, Zhao W, Liu Y, Zhou Y. Preliminary clinical evaluation of traditional and a new digital PEEK occlusal splints for the management of sleep bruxism. Journal of Oral Rehabilitation. Dec. 2020;47(12):1530-7.*

Kocabay, C. et al., The conservative treatment of pediatric mandibular fracture with prefabricated surgical splint: a case report, Dental Traumatology, 2007; vol. 23, Issue 4, pp. 247-250.

Metzger, M. C. et al., Manufacturing splints for orthognathic surgery using a three-dimensional printer, Oral Surgery, Oral Medicine, Oral Pathology, Oral Radiology, and Endodontology, vol. 105, Issue 2, Feb. 2008, pp. e1-e7.

International Search Report and Written Opinion of International Searching Authority dated Oct. 5, 2017 for corresponding PCT International Application No. PCT/US2017/044863.

International Preliminary Report on Patentability dated Feb. 14, 2019 for corresponding PCT International Application No. PCT/US2017/044863.

International Search Report and Written Opinion of International Searching Authority dated Jun. 12, 2015 for corresponding PCT International Application No. PCT/US2015/017126.

International Preliminary Report on Patentability dated Sep. 9, 2016 for corresponding PCT International Application No. PCT/US2015/017126.

* cited by examiner

REDUCTION SPLINT FOR EDENTULOUS PATIENTS

CROSS-REFERENCE TO RELATED APPLICATIONS

This nonprovisional application is a continuation of and claims priority to PCT International Patent Application No. PCT/US2017/044863, entitled "REDUCTION SPLINT FOR EDENTULOUS PATIENTS," filed Aug. 1, 2017, which is a continuation-in-part of U.S. Nonprovisional patent application Ser. No. 15/244,249, entitled "Custom Reduction Splint for Edentulous Patients," filed Aug. 23, 2016, which is a continuation of International Patent Application No. PCT/US2015/017126, entitled "Custom Reduction Splint for Edentulous Patients," filed on Feb. 23, 2015, which claims priority to U.S. Provisional Application No. 61/943,636, entitled "Custom Reduction Splint for Edentulous and Partially Edentulous Patients," filed Feb. 24, 2014. PCT International Patent Application No. PCT/US2017/044863, entitled "REDUCTION SPLINT FOR EDENTULOUS PATIENTS," filed Aug. 1, 2017 also claims priority to U.S. Provisional Patent Application No. 62/369,413, entitled "Reduction Splint for Edentulous Patients," filed Aug. 1, 2016. This nonprovisional application is also related to U.S. Pat. No. 9,192,505, entitled "Custom Reduction Splint for Edentulous Patients," filed Feb. 23, 2015 and issued Nov. 24, 2015, which also claims priority to U.S. Provisional Application No. 61/943,636, entitled "Custom Reduction Splint for Edentulous and Partially Edentulous Patients," filed Feb. 24, 2014. Each of the foregoing disclosures is incorporated herein by reference in its entirety.

TECHNICAL FIELD

This invention relates, generally, to oral splints. More specifically, it relates to the reduction and maintenance of reduction in mandible and/or maxilla fractures of edentulous or partially edentulous patients.

BACKGROUND

Oral splints are commonly known in the art, including those utilized for fixation of the jaw during recovery from mandibular or maxillary fractures. For example, U.S. Pat. No. 6,227,861 to Cartledge et al. discusses a pre-formed mandible splint and a method of aligning and stabilizing a fractured mandible with such a splint. The splint approximates the curvature of the lower teeth or gingiva of the lower jaw. The splint is U-shaped, follows the human dentition, and has rows of holes or slots along its outer and inner perimeter. The splint is placed on the teeth and wired through the holes or slots to the mandible to align the mandible. Fractures are then to be screwed into place according to the curvature of the splint. Cartledge attempts to improve upon the art by eliminating the need of wiring the patient's jaw shut. However, the splint of Cartledge is pre-formed and is intended to uniformly fit the population, and thus is not contoured to each patient's anatomy, but rather provides a singular, uniform flat surface in contact with variable anatomy. As the splint is in a fixed, straight plane, the patient's teeth may not all be at the same height in order to make adequate contact with the splint. Inconsistent dental height between adjacent teeth is common, especially in partially edentulous patients. Partially edentulous patients often have gaps between teeth from missing teeth. Any areas of missing teeth can lead to lengthening of the opposing tooth, as it does not have proper occlusal contact. For example, if a mandibular lateral incisor is absent, the opposing maxillary dentition will lack normal occlusal contact, which can result in lengthening of the opposing maxillary tooth. This further adds to any height discrepancies between teeth and leads to areas of non-contact between the tooth and splint, ultimately causing fracture malreduction. As such, Cartledge fails to provide either equally distributed contact or stability of fracture reduction. Further, the splint of Cartledge does not address the occlusion of the patient. If the splint rests in contact with dentition, it interferes with proper occlusion, which is the primary objective in fracture reduction. If the splint rests in contact with the gingiva directly, as in the case of an edentulous patient, then the proper distance is not maintained for the patient to wear their denture appliance postoperatively. Also, the Cartledge device is designed only for tooth-bearing regions of the mandible, including fractures of the symphysis, parasymphysis, and body. The device does not assist in reduction of mandible fractures of the angle, ramus, condyle or coronoid.

Additionally, U.S. Pat. No. 6,671,539 to Gateno et al. describes a method of forming a surgical splint to receive a patient's dentition and align the upper jaw and the lower jaw during surgery. The method disclosed includes generating a computed tomography (CT) computer model of bone structure, generating a digital dental computer model of the patient's dentition, and combining the CT computer model and the digital dental computer model to form a composite computer model. The upper jaw and lower jaw are repositioned to form a "planned position" computer model. Thereafter, a computer model of the surgical splint is formed to direct fabrication of the splint. However, this methodology is quite complex and involves multiple steps, including separate dental trays, dental modeling, and merging of the facial bone CT with dental CT data. This can become very time-consuming and inefficient in the fabrication of the splint. This device also does not address fracture reduction but rather is for craniofacial and maxillofacial deformities requiring osteotomies, which is not used for fracture reduction. The device also does not address postoperative maintenance of the surgical splint. The device does not appear to be designed to remain in place postoperatively, but rather serves only as an intraoperative device.

U.S. Pat. No. 6,086,365 to Fields discusses fracture reduction and maxillary fixation by using a dental splint that is cemented directly to the patient's teeth to immobilize the patient's jaw during and following oral surgery. The splint includes an arch band having a back side that receives the bonding cement and a facial side from which multiple ligature studs project for engaging ligature wires. The arch band further includes flow passages that permit bonding cement deposited on the back side to flow onto the facial side as the arch band is pressed against the patient's teeth. However, this device is not personalized for individual patient and also requires bonding to the patient's teeth. As it requires bonding to teeth, the device cannot be used in edentulous patients. Furthermore, the postoperative stability of the device is limited by the relative strength of the bonding agent used.

U.S. Patent Application Publication No. 2007/0074729 to Magnin describes a mandibular advancement splint used to treat snoring and sleep apnea. The splint is formed of two thermoformable trays designed to envelop the upper and lower arch. In order to adapt to individual variations in teeth, the splint includes an articulated frame having rigid and flexible elements, immersed in the thermoformable flexible material or molded around it. However, as indicated, the device is incapable of assisting with fracture reduction and is constructed of a thermoformable tray. This device is also only used while sleeping.

Metzger et al. (Marc Christian Metzger, Bettina Hohlweg-Majert, Uli Schwarz, Matthias Teschner, Beat Hammer, Rainer Schmelzeisen, Manufacturing splints for orthognathic surgery using a three-dimensional printer, Oral Surgery, Oral Medicine, Oral Pathology, Oral Radiology, and Endodontology, Volume 105, Issue 2, February 2008, Pages e1-e7, ISSN 1079-2104) discusses the use of various tomographic techniques to produce a virtual rendering of a patient's jaw in order to produce splints for orthognathic surgery using a 3D printer. Data is acquired from the patient with orthognathic deformation via CT scan or cone beam computed tomography (CBCT) scan. The jaws are virtually repositioned and encoded, followed by printing of the splint. However, this device fabrication requires a separate dental scan or scanning of plaster dental models, the information of which is then incorporated into a facial bones CT scan. The device also addresses orthognathic surgical procedures, rather than reduction of maxillary or mandibular fractures and is incapable of performing as such. Further, the device utilizes intraoperative splints, but does not comment on the ability of the splint to remain postoperatively. The device can only be used in patients with dentition and thus cannot be applied to partially or completely edentulous patients.

Kocabay et al. (Ceyda Kocabay, Mustafa Sancar Ataç, Burak Öner, Nadir Güngör, The conservative treatment of pediatric mandibular fracture with prefabricated surgical splint: a case report, Dental Traumatology Volume 23, Issue 4, pages 247-250, August 2007) discusses the use of a pre-formed surgical splint for mandibular fracture fixation. This publication discusses the development of a custom, pre-formed splint for mandibular fracture fixation though the use of pressure molds. The device utilizes plaster dental modeling for formation of the acrylic splint, which can hinder the availability of the splint for operative use. The device further requires dentition to maintain fracture stability, and thus does not have application to partially or completely edentulous patients.

In the case described by Kocabay et al., the fracture was a midline symphyseal mandible fracture. In this type of fracture, the rotational forces are minimal. In all other types of mandibular fractures, the rotational forces acting to disrupt fracture alignment are much greater. As the device is depicted, it is unlikely the acrylic splint alone could maintain fracture reduction with these strong, additional rotation forces characteristic of mandibular fractures. The device is illustrated in a pediatric fracture, which is likely a greenstick fracture, as the authors acknowledge. This means that the periosteum overlying the fractured bone remains intact on at least one side. With intact periosteum from a greenstick fracture, reduction of the fracture becomes significantly easier than when the entire periosteum is disrupted, and the fracture segments are freely mobile. In the adult patient, greenstick fractures are not seen, but rather, the entire periosteum is disrupted. Thus, in an adult fracture, it is doubtful that the acrylic splint would reduce the fracture and maintain postoperative alignment.

Generally, in difficult patient populations, such as those with edentulism or partial edentulism, there are very limited options for maxillomandibular fixation, and none provide stable reduction of fractures, including the foregoing devices and methodologies discussed. What is currently practiced in the art for an edentulous and partially edentulous patient with dentures, is that the patient's jaw is imaged upon removal of the dentures to ensure that the dentures are not blocking any visible fractures or other dentition. In many cases, the dentures are worn down and thus are not positioned where the patient's jaws should be aligned. As a result, the patient's jaw may have collapsed to an extent. To maintain the jaw in place then, the dentures are drilled or screwed into place since there is no other manner of estimating the spacing between the maxilla and mandible. This destroys the dentures for any future use and forces the patient to purchase a new set of expensive dentures.

Accordingly, what is needed is an improved reduction splint, and method of fabrication thereof, for edentulous and partially edentulous subjects or patients. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

The long-standing but heretofore unfulfilled need for a standardized but still well-fitting oral splint is now met by a new, useful, and nonobvious invention.

In an embodiment, the current invention is a method of fabricating an oral splint for reduction of an oral fracture in an edentulous or partially edentulous subject or patient. The method includes scanning/imaging a jaw of each of a plurality of individuals in a patient population to determine an array of dimensions of the jaws (e.g., palate width, palate length, maxillary length, maxillary width, maxillary anterior thickness, maxillary lateral thickness, maxillary curvature, posterior maxillary height, mandibular length, mandibular width, mandibular anterior thickness, mandibular lateral thickness, mandibular curvature, and posterior mandibular height of said plurality of individuals). These dimensions are then manipulated or transformed to generate a representative set of dimensions that is representative of a subset of the patient population. For example, a mean and standard deviation of each dimension can be calculated and thus be representative of a subset of the population.

The results of this manipulation/transformation are important into a software application that creates and image of a jaw that is representative of the subset of the patient population. This representative jaw image includes a maxilla and a mandible. The upper palate of the jaw is outlined, as is the lower palate of the jaw. The distances between the outlines is interpolated, and that distance is indicated as the initial splint configuration. At this point, the bone and dentition of the maxilla and mandible can be removed from the image of the jaw, and the initial splint configuration can be split into a maxillary splint and a mandibular splint, thus forming a virtual image of the resulting oral splint.

Upon importing the imaging results into the software program, the maxilla and mandible may be tessellated into a three-dimensional model.

The initial splint configuration may be expanded outwardly so that the mandible and maxilla of the subject can fit snugly or be contained therewithin.

An evacuation aperture may be formed in an anterior portion of the initial splint configuration, such that an upper portion of the evacuation aperture is disposed in the anterior portion of the maxillary splint and a lower portion of the evacuation aperture is disposed in the anterior portion of the mandibular splint.

The step of splitting the initial splint configuration into the maxillary and mandibular splints can be performed by positioning an anterior-posterior plane within a midsection of the initial splint configuration. The position of the plane in a cranial-caudal direction is based on the presence or absence of teeth within the jaw of the subject. In this case, the maxillary and mandibular splints can be split along this plane.

An extrusion can be disposed on a superior surface of the mandibular splint or on an inferior surface of the maxillary splint. A channel would then be disposed on the splint that did not receive the extrusion. The extrusion and channel would correspond positionally and dimensionally, so that a tongue and groove fitting is formed between the maxillary and mandibular splints. In a further embodiment, both the extrusion and channel are U-shaped along a jawline of the subject.

A plurality of wire apertures may be formed in the maxillary and mandibular splints to accommodate wiring to secure the maxillary and mandibular splints to the maxilla and mandible, respectively.

Projections may be disposed on the left and right sides of the maxillary splint, and projections may be disposed on the left and right sides of the mandibular splint. The projections on the maxillary splint may be aligned with the projections on the mandibular splint to facilitate wiring.

The step of fabricating the oral splint based on the virtual image of the oral splint may be performed by transmitting the virtual image to a three-dimensional printer for printing the oral splint.

An upper edge and/or lower edge of the initial splint configuration may be trimmed or filed down to better fit the jaw and soft tissue of the subject or patient (i.e., correcting for gum line, etc.)

If there is over rotation of the mandible when approximating the anterior edges of the maxilla and mandible, a spacer may be positioned on the mandible and/or maxilla (wherever dentition is absent) in order to provide proper spacing between the mandible and maxilla.

In a separate embodiment, the current invention is a surgical technique for reduction of an oral fracture in an edentulous or partially edentulous subject or patient. A virtual image of the oral splint can be generated using the foregoing descriptions. Upon creation of that virtual image, the oral splint can be fabricated therefrom, for example by three-dimensional printing. Once the physical splint has been fabricated, the maxillary splint is positioned and secured on the maxilla of the subject with the maxilla and its fractures in a reduced position. Similarly, the mandibular splint is positioned and secured on the mandible of the subject with the mandible and its fractures in a reduced position.

The step of securing the maxillary splint onto the maxilla of the subject may be performed by pyriform drop wire and/or transpalatal-pyriform wire. The step of securing the mandibular splint onto the mandible of the subject may be performed by circummandibular wires via use of an awl or similar method.

Projections may be disposed on the left and right sides of the maxillary splint, and projections may be disposed on the left and right sides of the mandibular splint. The projections on the maxillary splint may align with the projections on the mandibular splint to facilitate wiring, if desired. In a further embodiment, the maxillary and mandibular splints can be secured to each other via intersplint wires wrapped around the corresponding projections on the maxillary and mandibular splints.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 3B(b) shows the multi-step process for point registration in order to realign or reassemble the jaw of FIG. 3A and the fractured shards thereof.

FIG. 3B(c) shows the multi-step process for point registration in order to realign or reassemble the jaw of FIG. 3A and the fractured shards thereof.

DETAILED DESCRIPTION

Figure 1A:
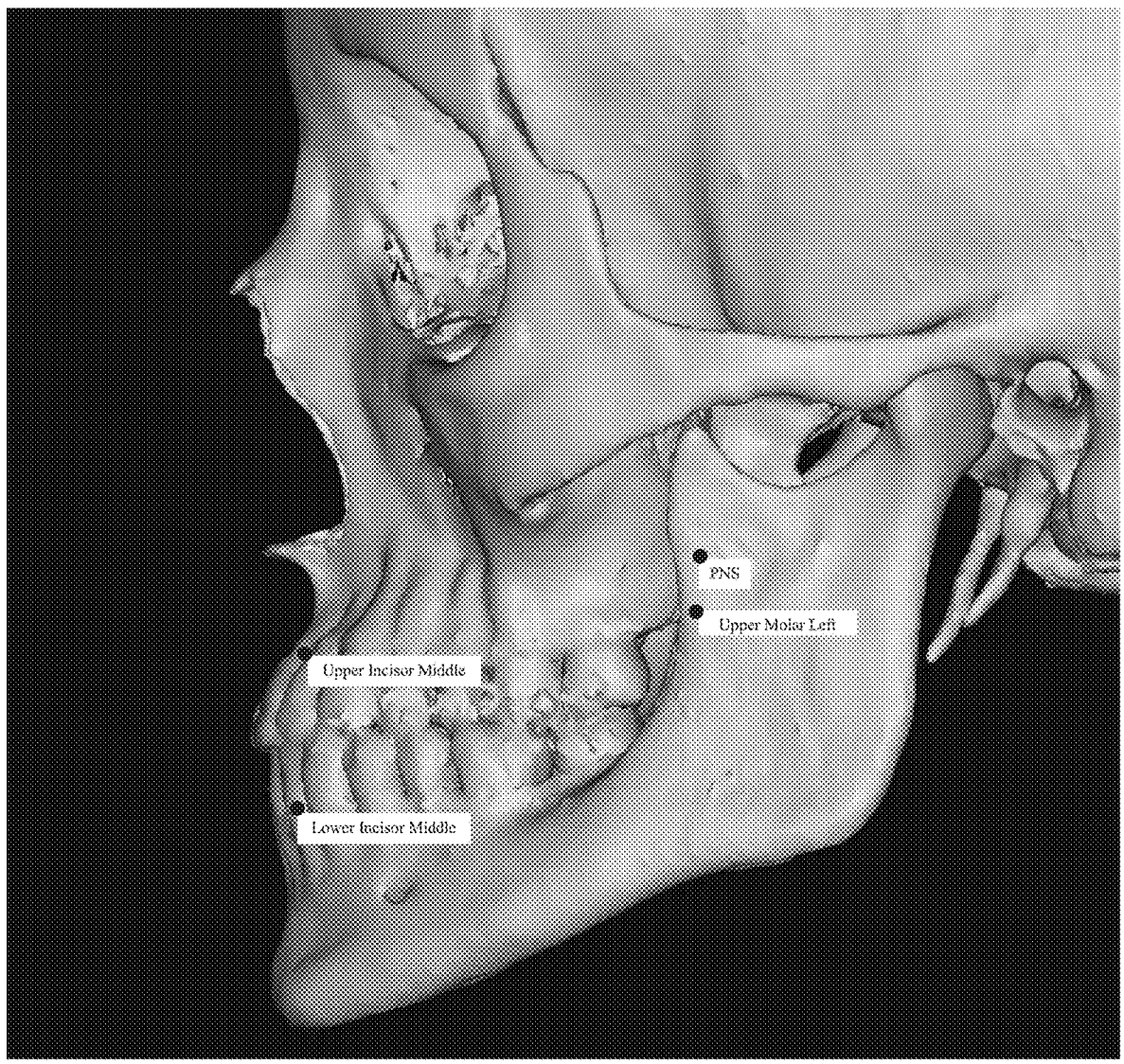
FIG. 1A is a lateral view of a jaw.

In the following detailed description, reference is made to the accompanying drawings, which form a part thereof, and within which are shown by way of illustration specific embodiments by which the invention may be practiced. It is to be understood that other embodiments may be used, and structural changes may be made without departing from the scope of the invention.

These embodiments are described in sufficient detail to enable those of ordinary skill in the art to practice the present disclosure, and it is to be understood that other embodiments may be utilized, and that structural, logical, and electrical changes may be made within the scope of the disclosure.

From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. Only those process acts and structures necessary to understand the embodiments of the disclosure are described in detail below. A person of ordinary skill in the art will understand that some process components are inherently disclosed herein and that adding various conventional process components and acts would be in accord with the disclosure. In this description, specific implementations are shown and described only as examples and should not be construed as the only way to implement the present disclosure unless specified otherwise herein.

Illustrations presented herein are not meant to be actual views of any particular material, component, or system, but are merely idealized representations that are employed to describe embodiments of the disclosure. Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Any headings used herein should not be considered to limit the scope of embodiments of the invention as defined by the claims below and their legal equivalents. Concepts described in any specific heading are generally applicable in other sections throughout the entire specification.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a device. The proximal end of the device is defined as the end of the device closest to the user when the device is in use. The distal end is the end opposite the proximal end, along the longitudinal direction of the device, or the end furthest from the user.

The use of "including," "comprising," or "having," "containing," "involving," and variations thereof herein, is meant to encompass the items listed thereafter and equivalents thereof as well as any additional items a person of ordinary skill in the art would reasonably understand to be included.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The current invention is related to, and in some embodiments and extension of, U.S. Pat. No. 9,192,505 (the '505 patent), which is incorporated herein by reference in its entirety. The '505 patent generally teaches the fabrication of an oral splint that is operatively secured to the maxilla and mandible of a subject/patient to assist in reduction and provide maintenance of reduction of maxillary and mandibular fractures in the edentulous or partially edentulous subject/patient. The fabrication of this oral splint typically occurs on a patient-by-patient basis, such that the fabricated oral splint is customized to each patient. However, the current invention contemplates fabricating one or more standard sizes (e.g., small, medium, large) of oral splints for use on a group of patients/subjects. As contemplated herein, oral splints are fabricated in a similar way and for a similar patient population. The standard sizes would be based on averaged dimensions and features of a patient population.

Example 1—Determination of Sizing

To fabricate a range of sizes of a standardized reduction splint for edentulous patients, an array of individuals is sized to generate a data set. A distribution is created from this data set, where the distribution includes particular parameters that divides the distribution into a predetermined number of subsets based on the sizing. Each subset corresponds to a size of the reduction splint, and the dimensions of the size are determined generally by average dimensions contained within the data set corresponding to the particular subset.

Figure 1B:
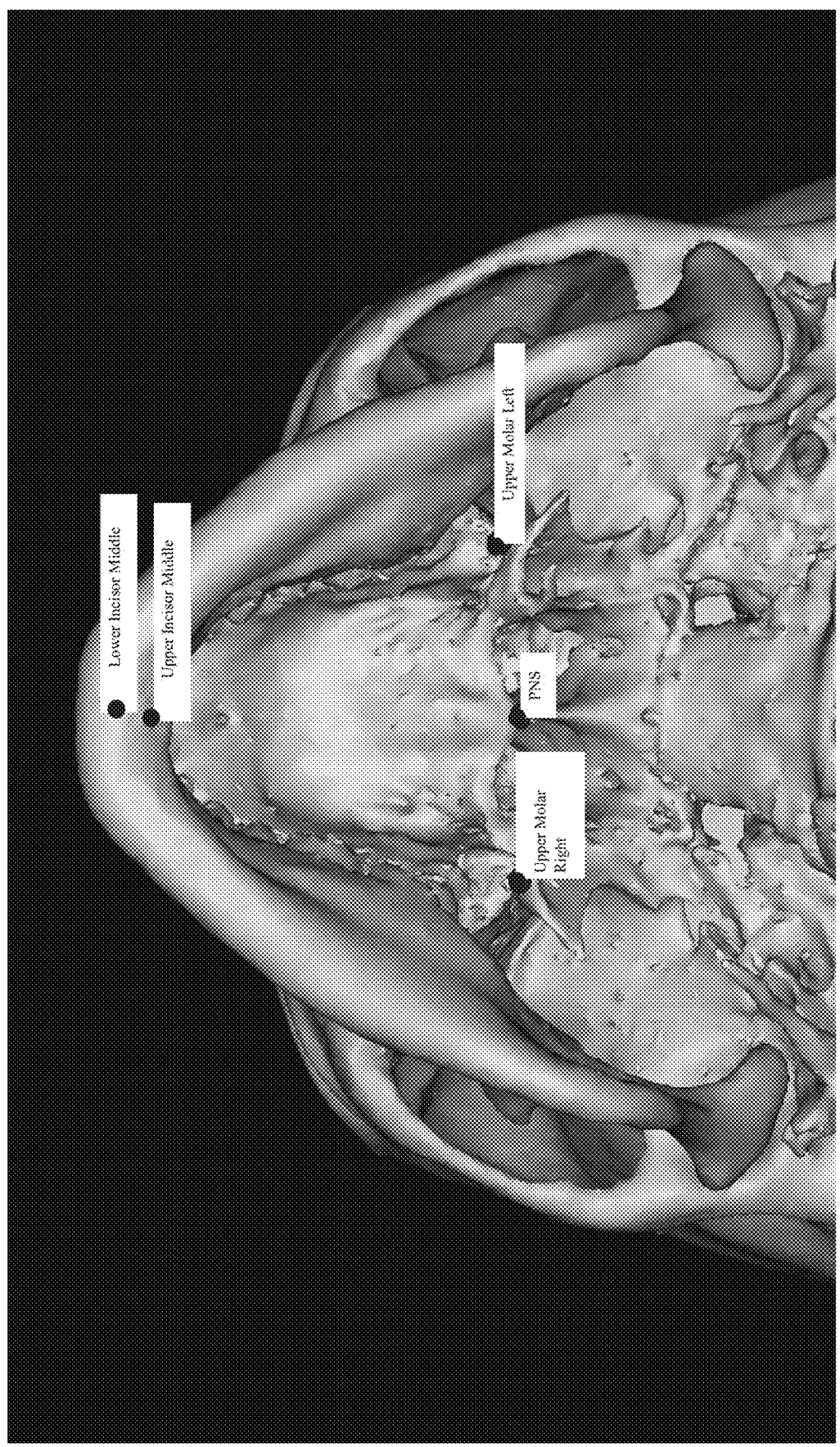
FIG. 1B is an inferior view of a jaw.
Figure 2A:
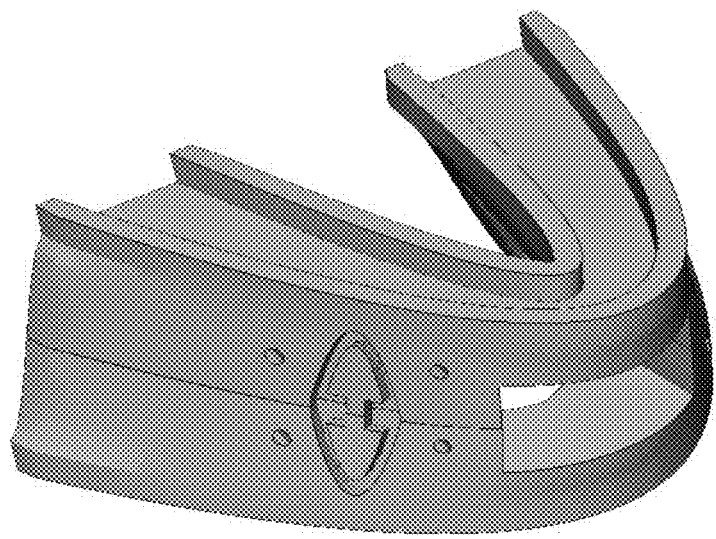
FIG. 2A is a perspective view of a reduction splint, fabricated according to certain embodiments of the current invention.
Figure 2B:
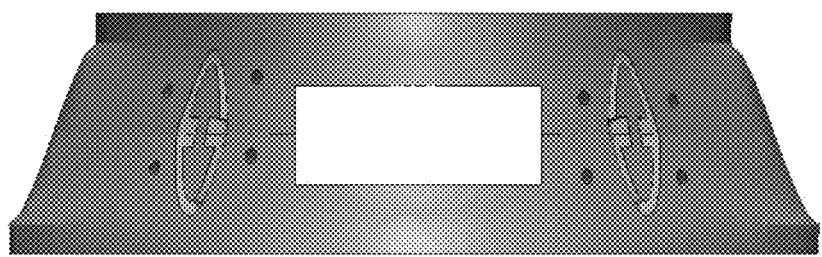
FIG. 2B is a front view of the reduction splint of FIG. 2A.
Figure 2C:
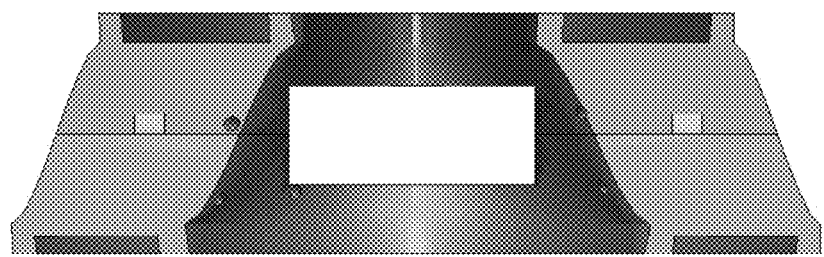
FIG. 2C is a rear view of the reduction splint of FIG. 2A.
Figure 2D:
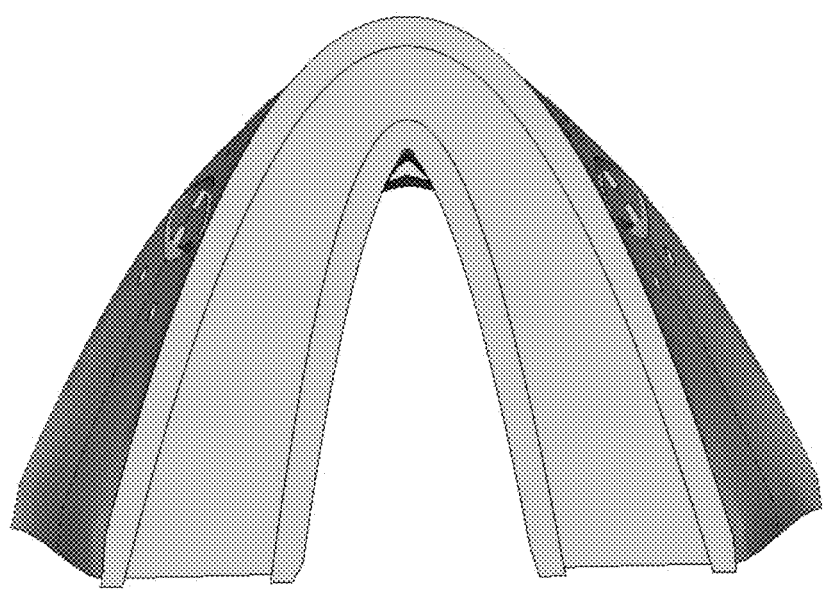
FIG. 2D is a top view of the reduction splint of FIG. 2A.
Figure 2E:
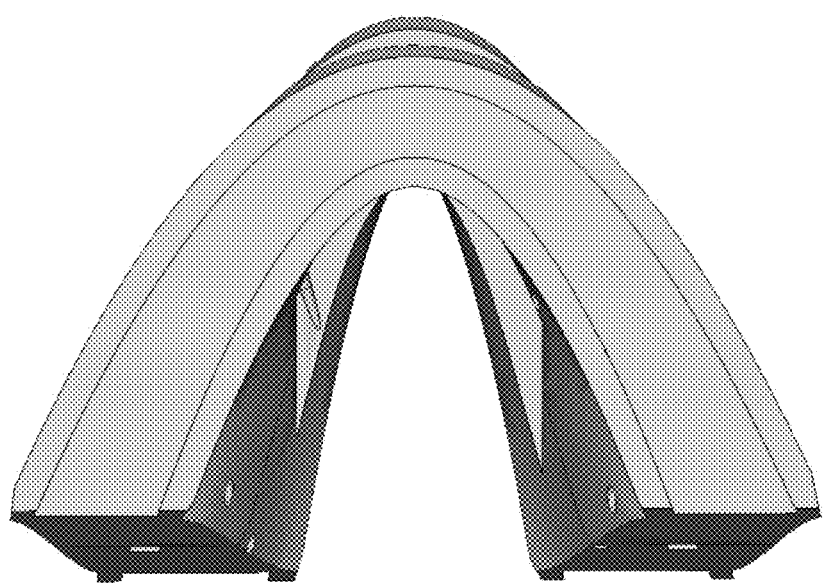
FIG. 2E is a bottom view of the reduction splint of FIG. 2A.

As an example, measurements were taken from a population of 50 adults, average age was 58±20 years. There were 25 males and 25 females. Table 1 contains the measures and their definitions (see also FIGS. 1A-1B).

TABLE 1

Measurements and definitions.

| | Measurement | Definition |
|---|---|---|
| Maxillary | Length | Midpoint of the frontal incisors to the posterior nasal spine |
| | Width | Distance between the left and right posterior points of the alveolar ridge |
| | Anterior thickness | Thickness at the front of the maxilla just superior to the incisors |
| | Lateral thickness | Thickness at the lateral side of the maxilla at most posterior molar |
| Mandible | Length | Midpoint of the frontal incisors to the plane formed from the posterior nasal spine and the left and right posterior points of the retro-molar fossa |
| | Width | Distance between the left and right points of the retro-molar fossa |
| | Anterior thickness | Thickness at the front of the mandible just inferior to the incisors |
| | Lateral thickness | Thickness at the lateral side of the mandible on most posterior molar |

Table 2 illustrates the central tendency for the data collected (H=height, L=length, W=width, T=thickness).

TABLE 2

Central tendency for the data collected.

| | | Incisor H | Man L | Man L | Man Lat T | Man Ant T | Max W | Max L | Max Ant T | Max Lat T |
|---|---|---|---|---|---|---|---|---|---|---|
| N | Valid | 50 | 50 | 50 | 50 | 50 | 50 | 50 | 50 | 50 |
| | Missing | 0 | 0 | 0 | 0 | 0 | 0 | 0 | 0 | 0 |
| Mean | | 18.81 | 39.80 | 65.34 | 12.55 | 7.24 | 45.06 | 50.41 | 7.60 | 14.93 |
| Median | | 18.36 | 39.10 | 65.90 | 12.57 | 7.34 | 45.44 | 50.98 | 7.39 | 14.90 |
| SD | | 3.02 | 4.67 | 4.95 | 2.35 | 1.34 | 3.53 | 4.82 | 1.35 | 2.27 |
| % ile | 33.33333333 | 17.53 | 37.01 | 64.26 | 11.37 | 6.42 | 42.75 | 48.77 | 6.95 | 13.84 |
| | 66.66666667 | 19.36 | 40.79 | 67.24 | 13.55 | 7.78 | 46.64 | 52.11 | 8.01 | 15.85 |

Sizes of the standardized reduction splints were determined from the averages and standard deviations of the measurements. These measurements provided the dimensions to construct the off-the-shelf splints for the appropriate size. The lower and upper jaw can be the same or different sizes as the lower and upper dimensions can be interpolated for the best fit. Once the space for the alveolar ridges have been constructed, an outer lip is created in order to ensure stability and fit. Anchoring tabs and pre-drilled holes can be created to assist in fixation.

The resulting splint, as depicted in FIGS. 2A-2E, is split in two parts (superior and inferior) to assist in ease of use. A tongue and groove ridge is created at the of the superior and inferior halves to assist in stability and proper alignment. This will become clearer as this specification continues.

The splint can be physically manufactured or fabricated according to the above-referenced dimensions via either 3D-printed or more traditional manufacturing processes such as injection molding.

In a particular non-limiting example, a medium upper and lower splint (as depicted in FIGS. 2A-2E) would have the following dimensions. The upper/superior half of the splint can have an upper length of about 50.5 mm, upper width of about 45 mm, anterior thickness of about 7.5 mm, and posterior lateral thickness of about 15 mm. The lower/inferior half of the splint can have a lower length of about 40 mm, upper width of about 65 mm, anterior thickness of a about 7.25 mm, and posterior lateral thickness of about 12.5 mm. When the halves are combined to form the resulting splint, the height of the splint can be about 18.5 mm.

The foregoing descriptions discuss a methodology behind sizing a reduction splint to accommodate a subset of individuals in a population, for example in sizes of small, medium, and large. More specific sizes may also be generated for individuals with longer jaws, resulting in a "medium-long" size, for example. The current invention contemplates any number of sizes and dimensions, though each size should be able to accommodate a plurality of individuals within a population. Virtual and physical fabrication of the reduction splint (i.e., formation of the maxillary splint, mandibular splint, evacuation aperture, etc.) is discussed in both International Patent Application No. PCT/US2015/017126 and U.S. Pat. No. 9,192,505, each of which is incorporated by reference in its entirety.

Example 2—Modeling and Printing of Reduction Splint

A "U-shape" of different sizes, e.g., small, medium, and large, is established from medical images obtained from population data. Sizes were determined from the mean and the standard deviations of the palate width, palate length and mandible width, maxillary and mandibular curvatures, posterior mandibular height, length and thickness. The total splint height can be about 2 cm, with the total internal groove height being about 1.5 cm, though other dimensions are contemplated by one of ordinary skill in the art. A rectangular hole of about 12-mm height and 20-mm width (or other suitable sizes) is created to accommodate a suctioning instrument (e.g., MEDI-VAC) and any potential vomiting from the patient.

A horizontal plane is created at the middle of the splint to split the splint in half or otherwise into two portions, an inferior portion and a superior portion. A U-shaped sketch is created on the inferior side of the superior portion (e.g., upper half) of the splint. The sketch creates an extruded surface (e.g., about 2 mm) that is Boolean subtracted from the inferior part of the splint. This creates the tongue and groove portion, which may be omitted or altered if needed. Apertures (e.g., eight approximately 1.5 mm-diameter apertures) are then placed in the superior and inferior portions of the splint (e.g., four in each half) to accommodate for wiring. Two or more ovular (or otherwise curved) tabs are also created on the front of the splint to allow for anchoring of the two halves together. Divots are placed in these oval tabs to allow for easy access to cut the wire if need be. These holes, tabs, divots, or similar modifications of the external surface may be altered or omitted as best suited for the intended use.

Once the model is created in virtual space, it is double-checked and smoothed to prevent any sharp edges from hurting the patient. The model is then exported and sent to a 3D printer, completed by other manufacturing device or process, or combination of processes. The splint may be fabricated from a single material or combination of materials as suited for the intended use. Once manufactured, the model is sanded to ensure a smooth surface.

Example 3—Modeling and Printing of Reduction Splint

Figure 3A:
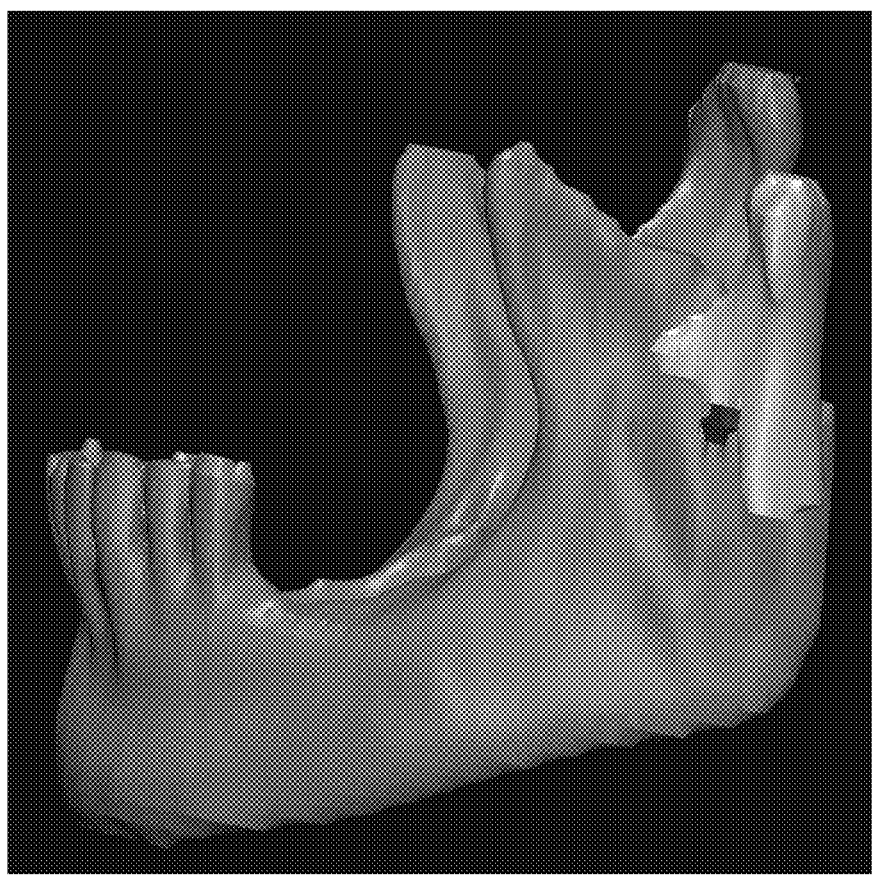
FIG. 3A is a 3D model/image/representation of a fractured jaw as seen in an image processing software program upon importation of the medical image into the software program.

Upon fabricating a jaw that is representative of a subset of the patient population, the representative jaw can be viewed on any suitable medical image processing software package, for example MIMICS by MATERIALISE. Within the image on the image processing software program, the bone structures of the maxilla and mandible are segmented and then tessellated into three-dimensional models, as can be seen in FIG. 3A showing a jaw fracture. The broken or fractured bones are realigned virtually with the jaw as a whole, in particular the mandible, realigned, and placed into a "normal", healthy or unfractured position.

Figure 3B:
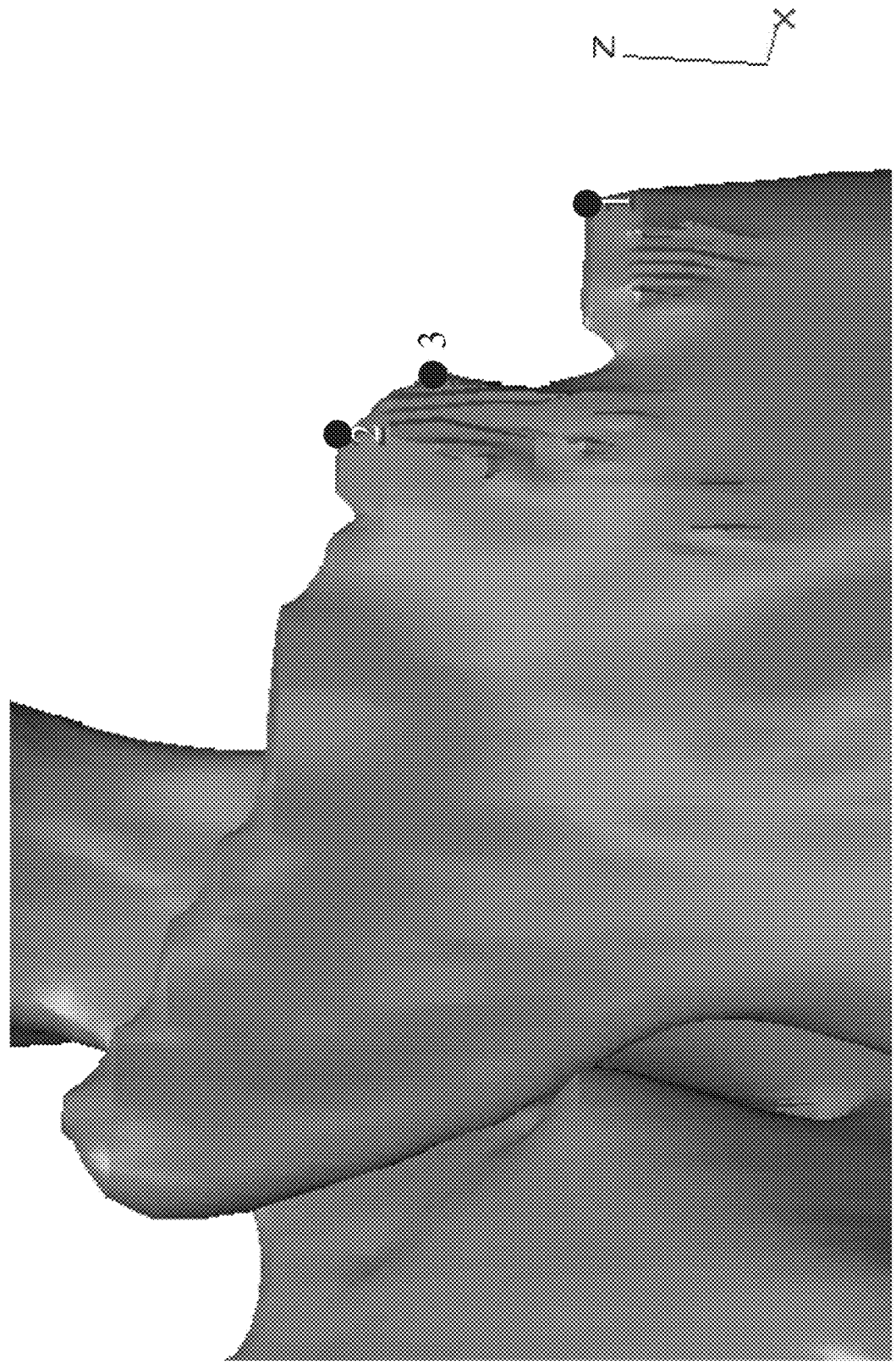
FIG. 3B(a) shows the multi-step process for point registration in order to realign or reassemble the jaw of FIG. 3A and the fractured shards thereof.
Figure 3B:
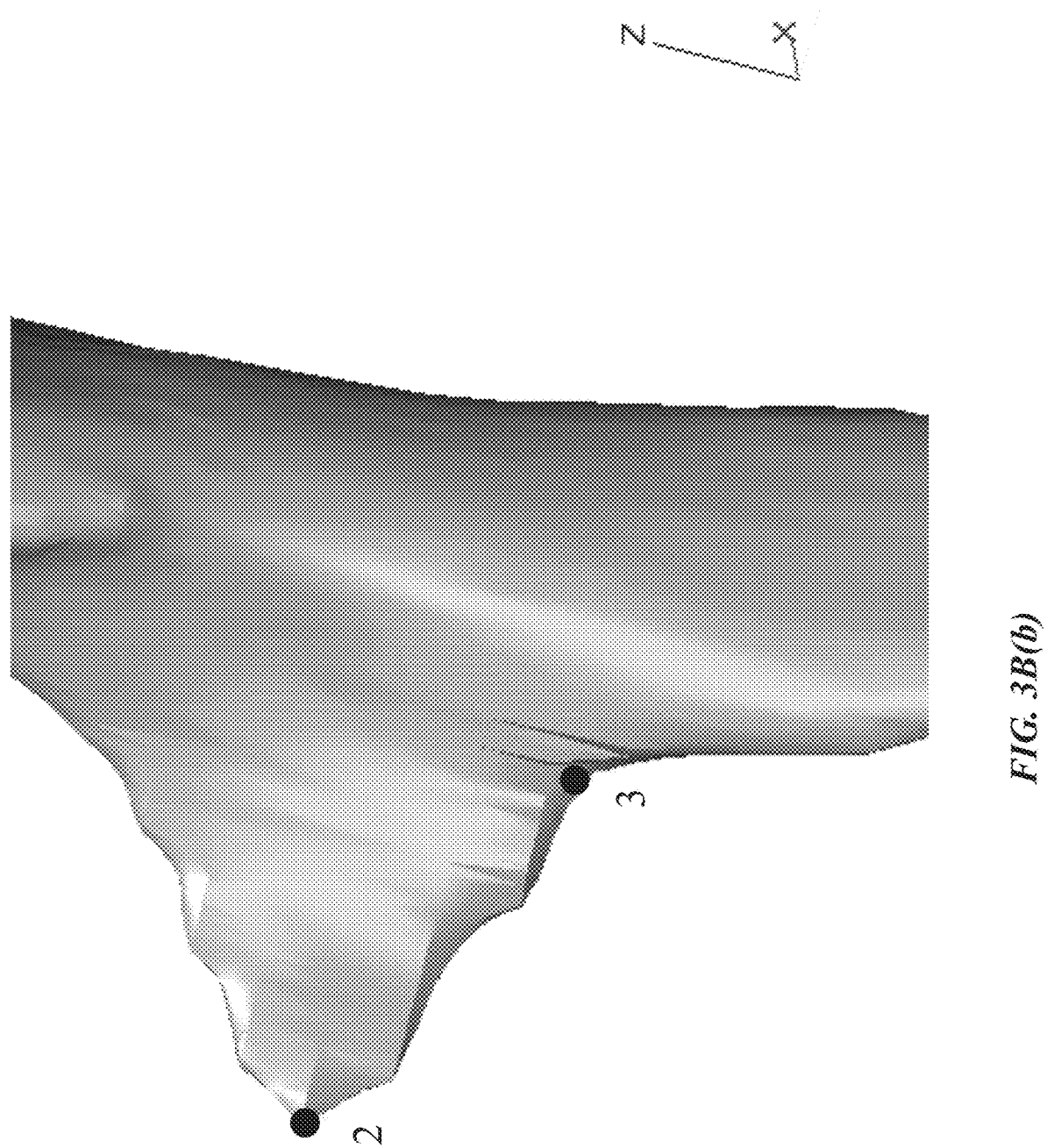
Figure 3B:
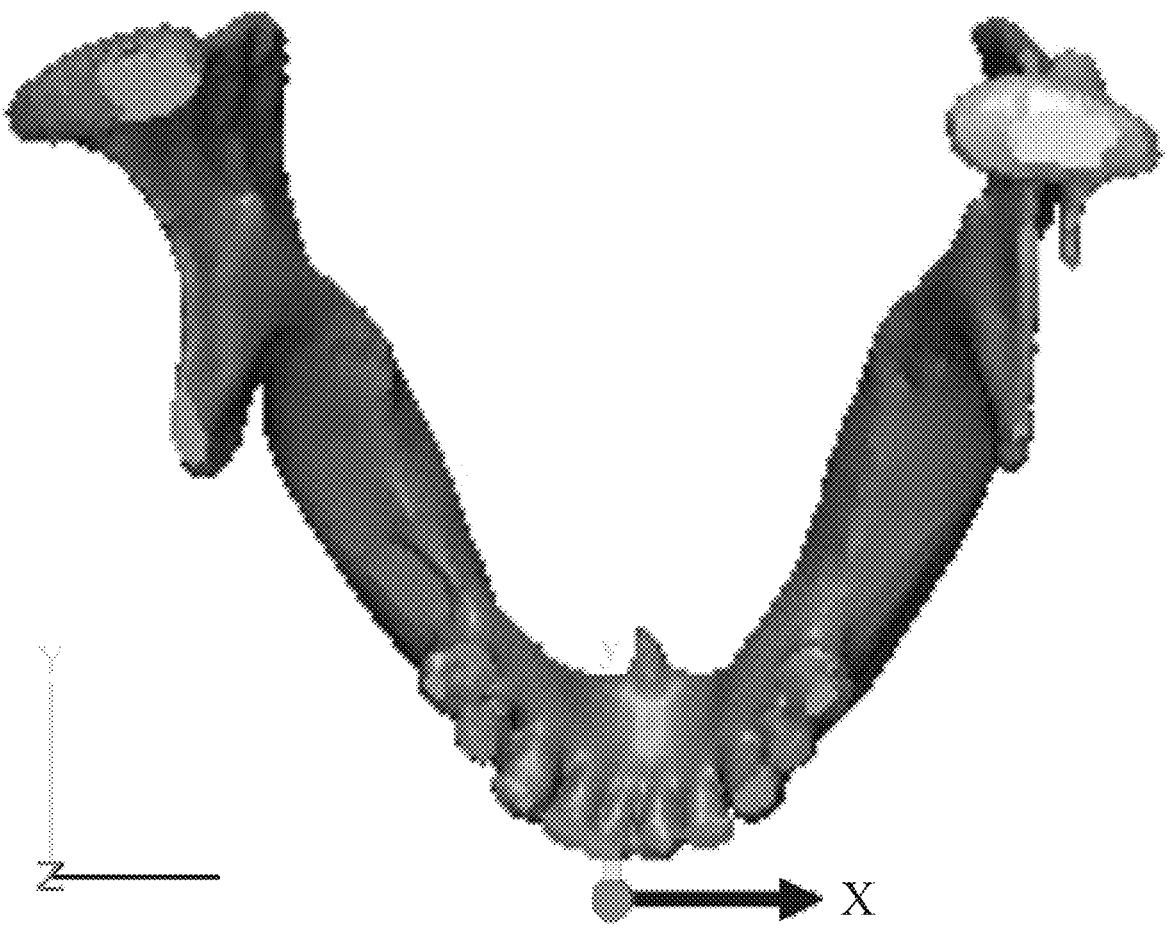

The fractured shards of the jaw can be realigned, for example, using point realignment or registration, which is shown in FIGS. 3B(a), 3B(b), and 3B(c), though any suitable methodology is contemplated herein. Point registration allows the fractured shards to be reassembled by placing a certain number of points on an initial surface (e.g., the jaw) (FIG. 3B(a)) and then placing corresponding points on the other surface (e.g., the jaw fragment) (FIG. 3B(b)) to which the initial surface is to be matched. A "best fit" can then be computed using those points to assemble the parts and thus realign the fractured shards in a normal or healthy position (FIG. 3B(c)).

Figure 3C:
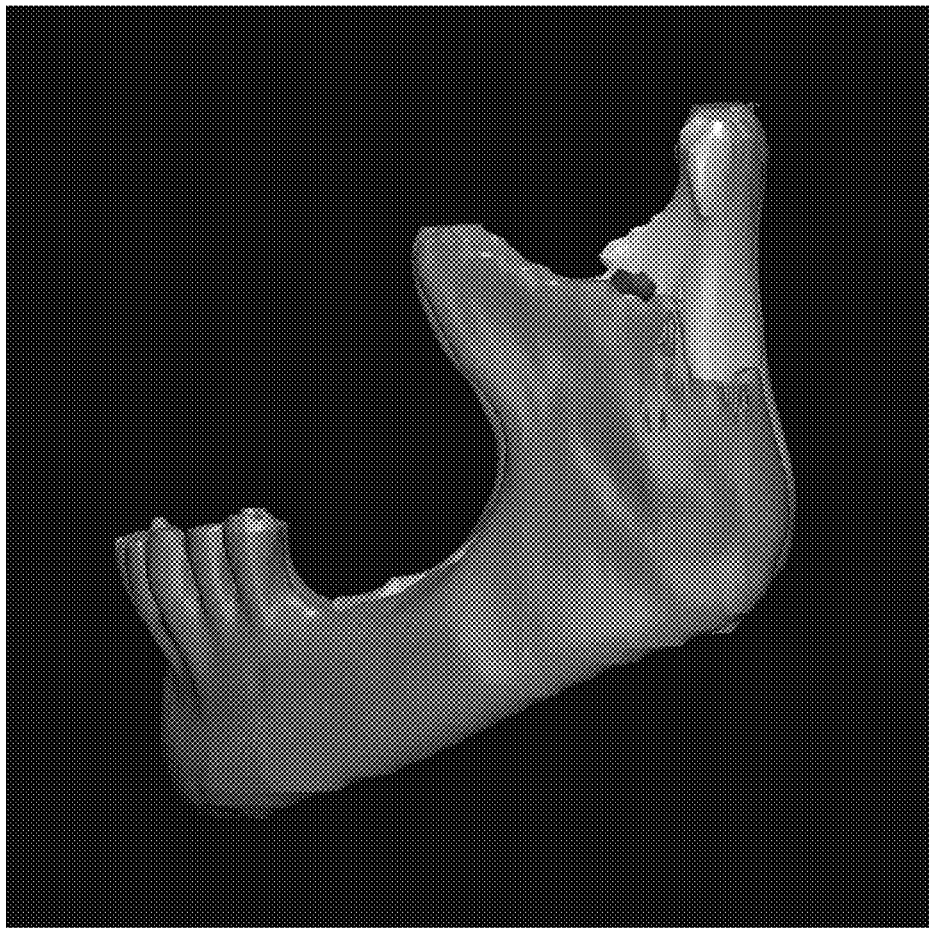
FIG. 3C is a 3D model/image/representation of a realigned jaw, corrected from the fractured jaw of FIG. 3A and resulting from the point realignment of FIGS. 3B(a), 3B(b), and 3B(c).
Figure 3D:
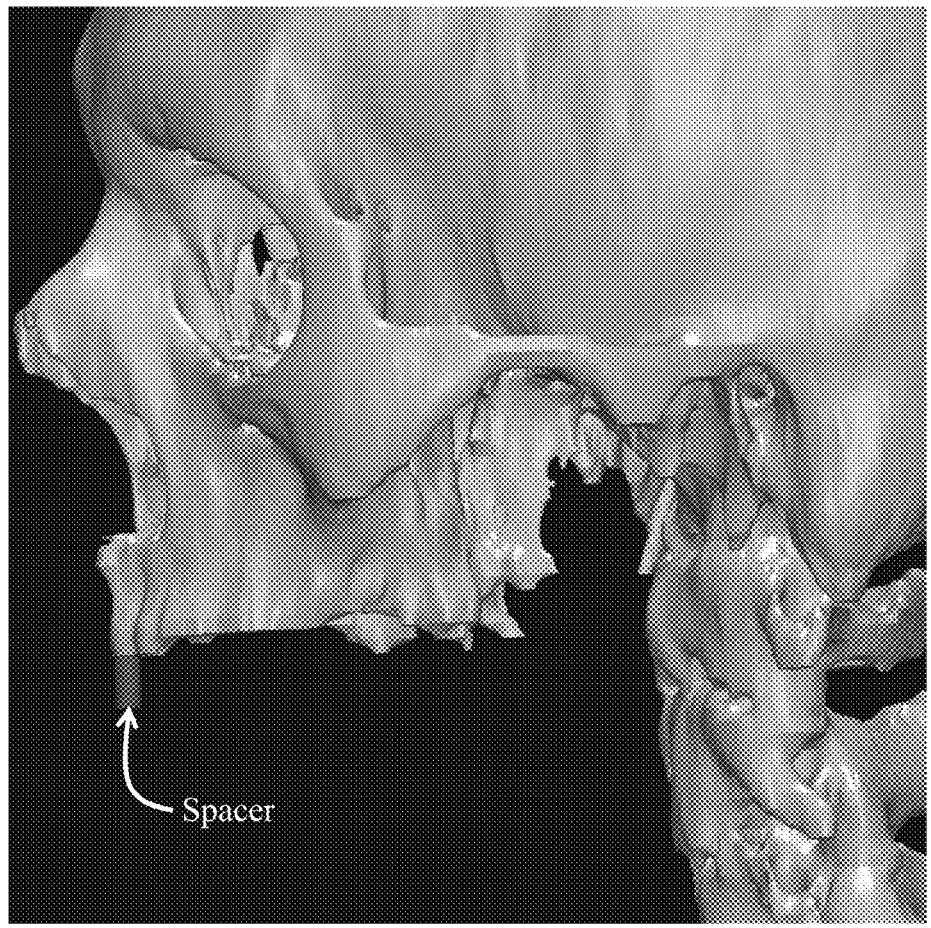
FIG. 3D depicts a spacer that may be used for repaired jaw alignment. In this particular case, maxillary teeth are absent, and as such, the spacer extends from the maxilla.

Regardless of the methodology used, the fractured shards are realigned into the normal position, as can be seen in FIG. 3C. At this point, if a situation exists such that the maxilla or mandible would be over rotated if the anterior edges of the maxilla and mandible were approximated, a spacer (shown in FIG. 3D) can be positioned. For example, FIG. 3D shows a lack of maxillary teeth, resulting in the spacer being used to represent the maxillary teeth so that the mandible does not over rotate and thus lead to non-anatomic healing. In other words, the spacer is used to maintain the spacing that healthy dentition would otherwise occupy. It is contemplated herein that this spacer can be positioned on the mandible as well if needed.

Figure 3E:
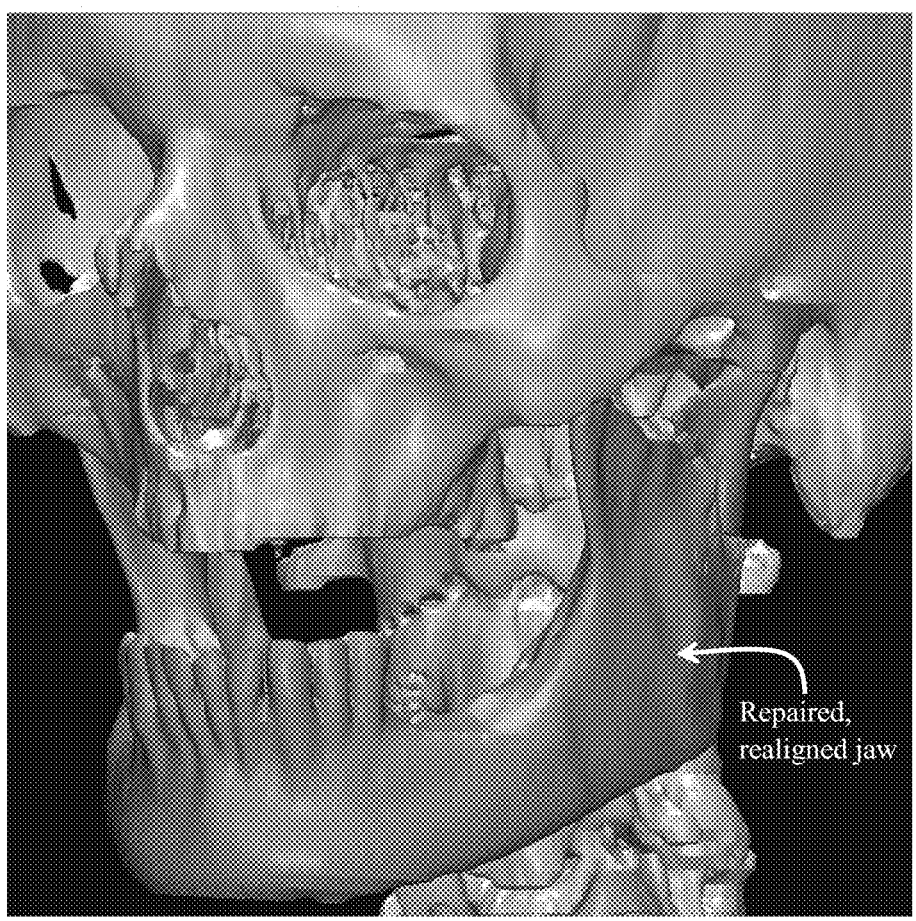
FIG. 3E depicts a realigned, repaired jaw from FIGS. 3A-3D.
Figure 3F:
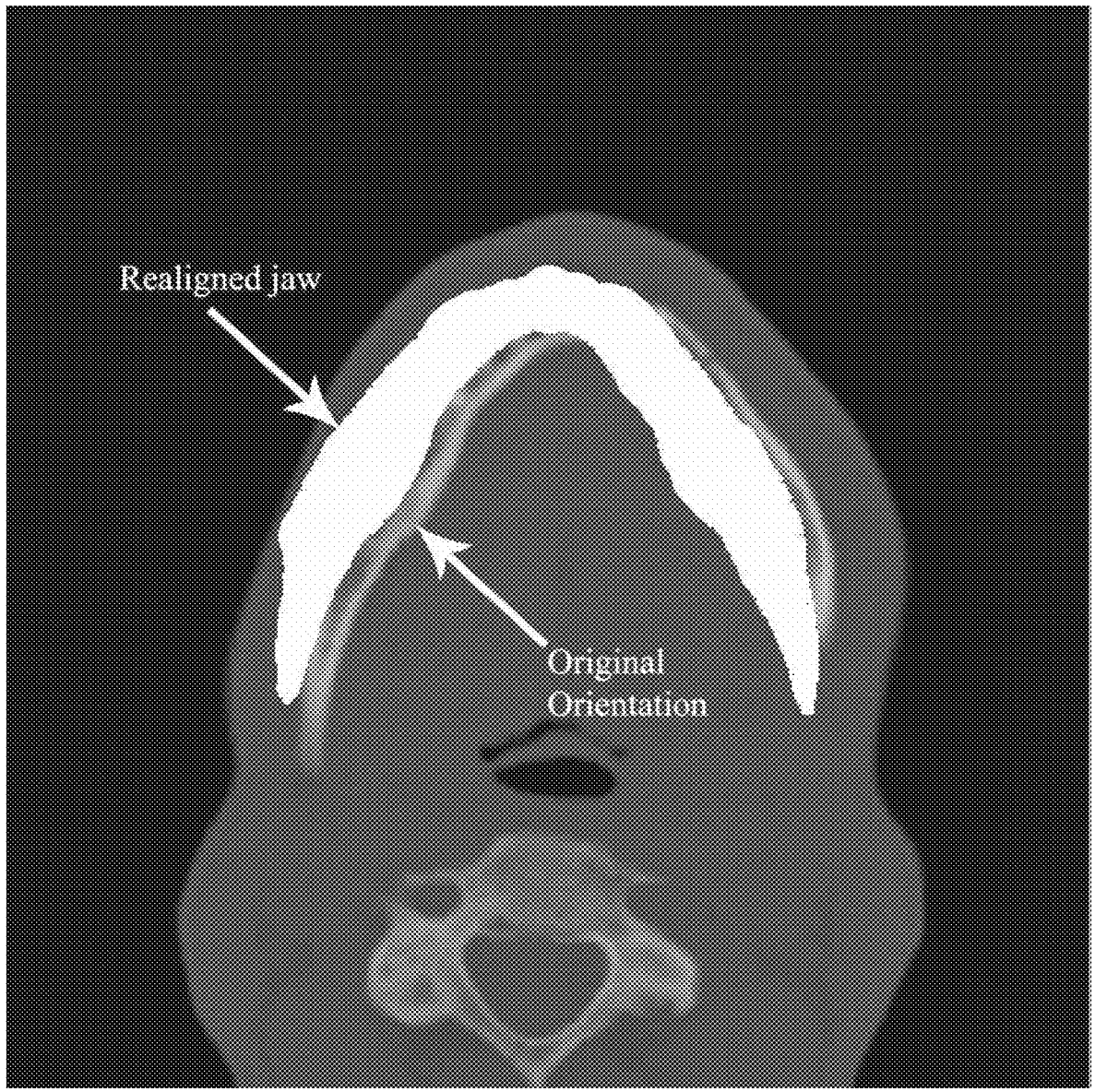
FIG. 3F is a CT image of the realigned jaw compared to the original fractured jaw from FIG. 3A.

Once the fractured shards of the jaw are realigned, as seen in FIG. 3C, and any spacing issues are resolved (see FIG. 3D), the representative jaw is realigned and fixed, as in FIG. 3E, if necessary. FIG. 3F shows a comparison of the realigned jaw to the underlying original position of the dentition. The jaw (and resulting splint) should be realigned, however, in order to provide proper healing and reduction of the fractures.

Figure 4A:
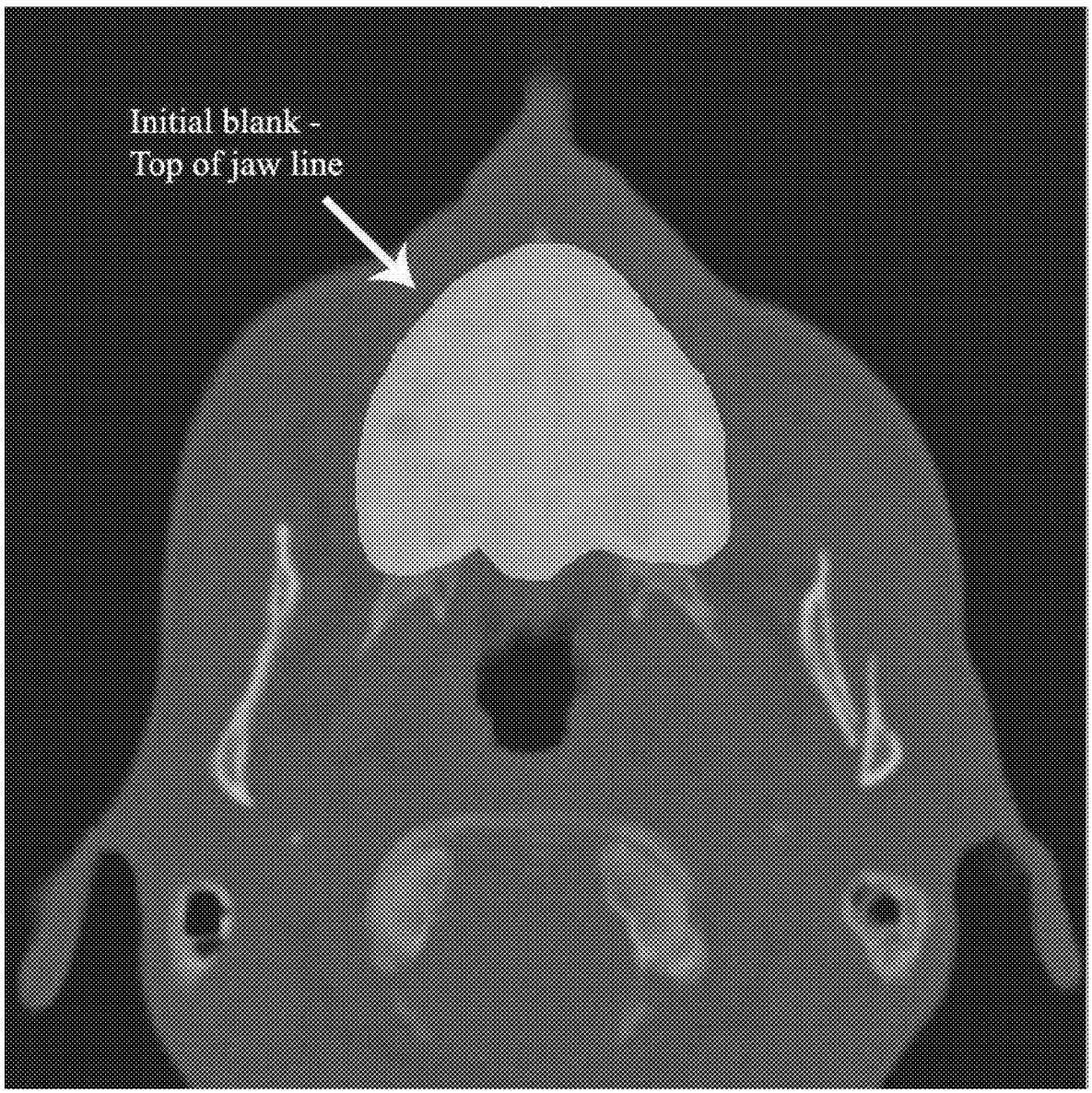
FIG. 4A depicts an initial blank creation from the U-shape that follows the top of the jaw line.
Figure 4B:
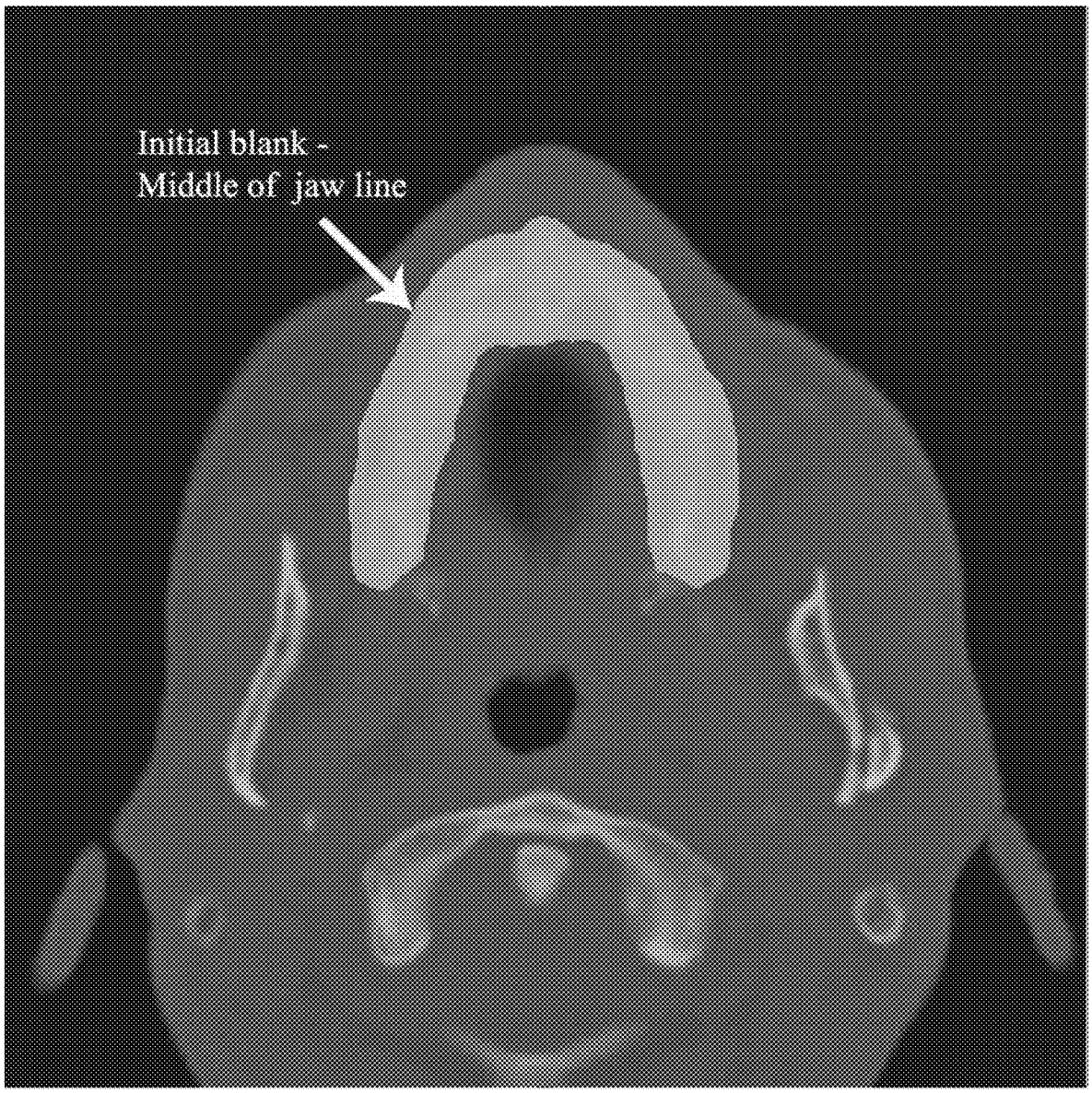
FIG. 4B depicts an initial blank creation from the U-shape that follows the middle of the jaw line.
Figure 4C:
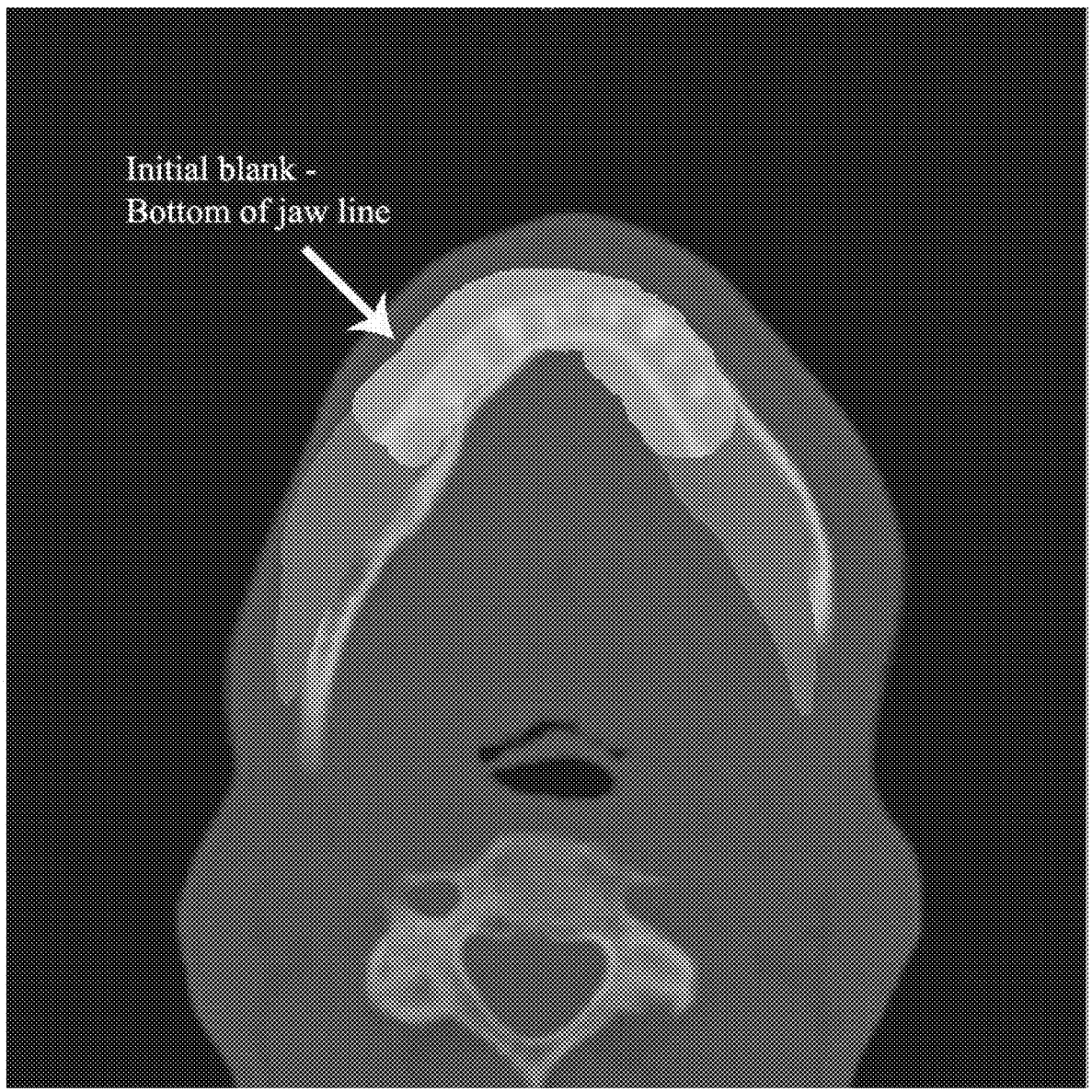
FIG. 4C depicts an initial blank creation from the U-shape that follows the lower portion of the jaw line.
Figure 4D:
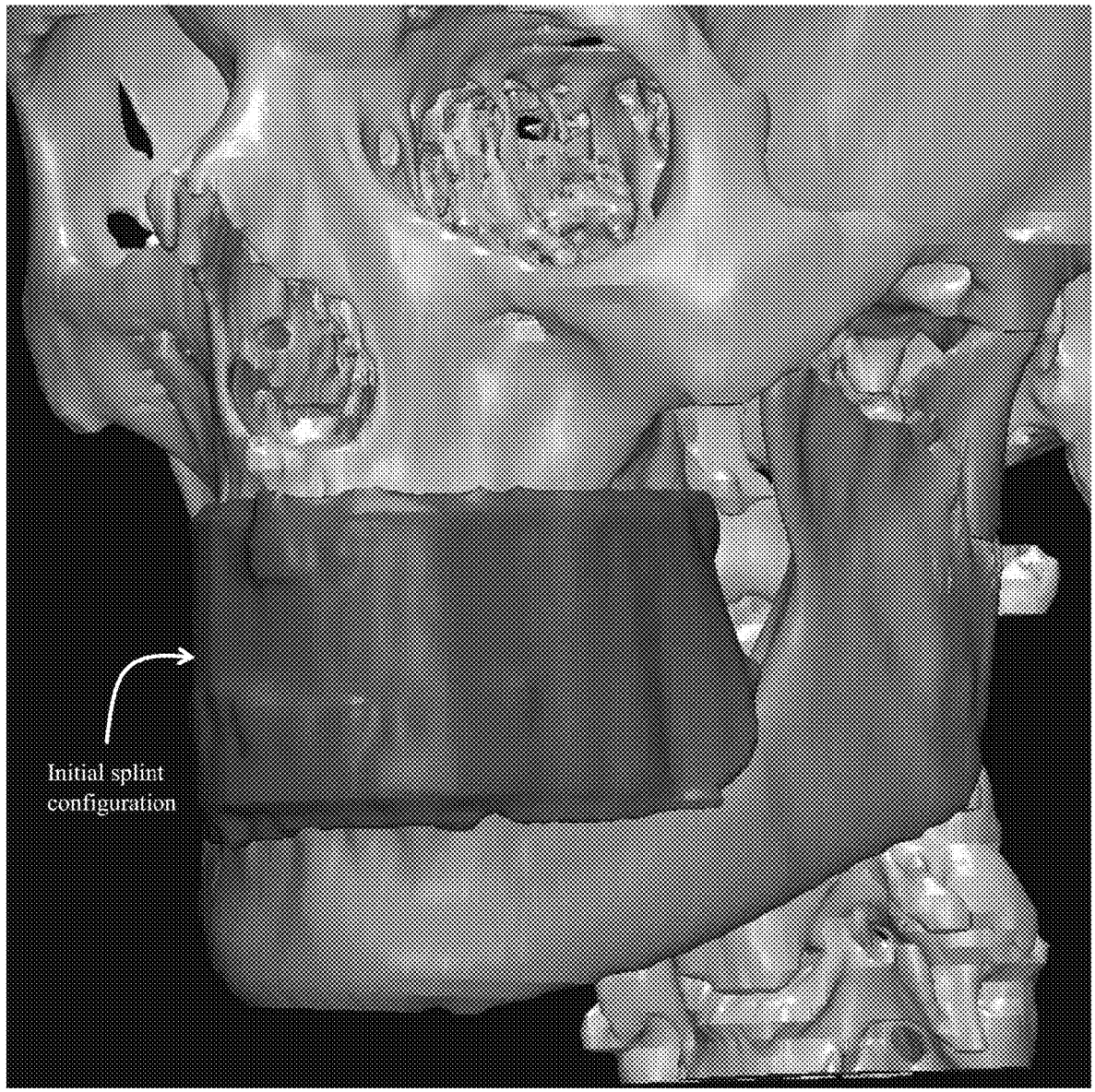
FIG. 4D is a 3D model/image/representation of the blank (initial splint configuration) resulting from interpolation of FIGS. 4A-4C.

At this point, a "blank" or initial splint configuration can be created on the image processing software program. Using the image of the representative jaw, various portions of the splint itself can begin taking form. The upper palate is lined, forming the uppermost portion of the splint, including the palate, as shown in FIG. 4A. A "U-shape" can then be drawn or illustrated along the upper (maxillary) jaw/dentition (FIG. 4B) and also along the lower (mandibular) jaw/dentition (FIG. 4C). These "U-shapes" follow the jaw line of the representative jaw. The distance between the results of FIGS. 4A-4C are then interpolated within the software program to create the general size of the blank or initial splint. The interpolation can be indicated in any way, such as by coloring in the distance as a solid, as can be seen in darker gray in FIG. 3D. Once this initial model is made, the stereolithic files (STL) can be imported into any suitable design software package, such as 3-MATIC by MATERIALISE.

Figure 5:
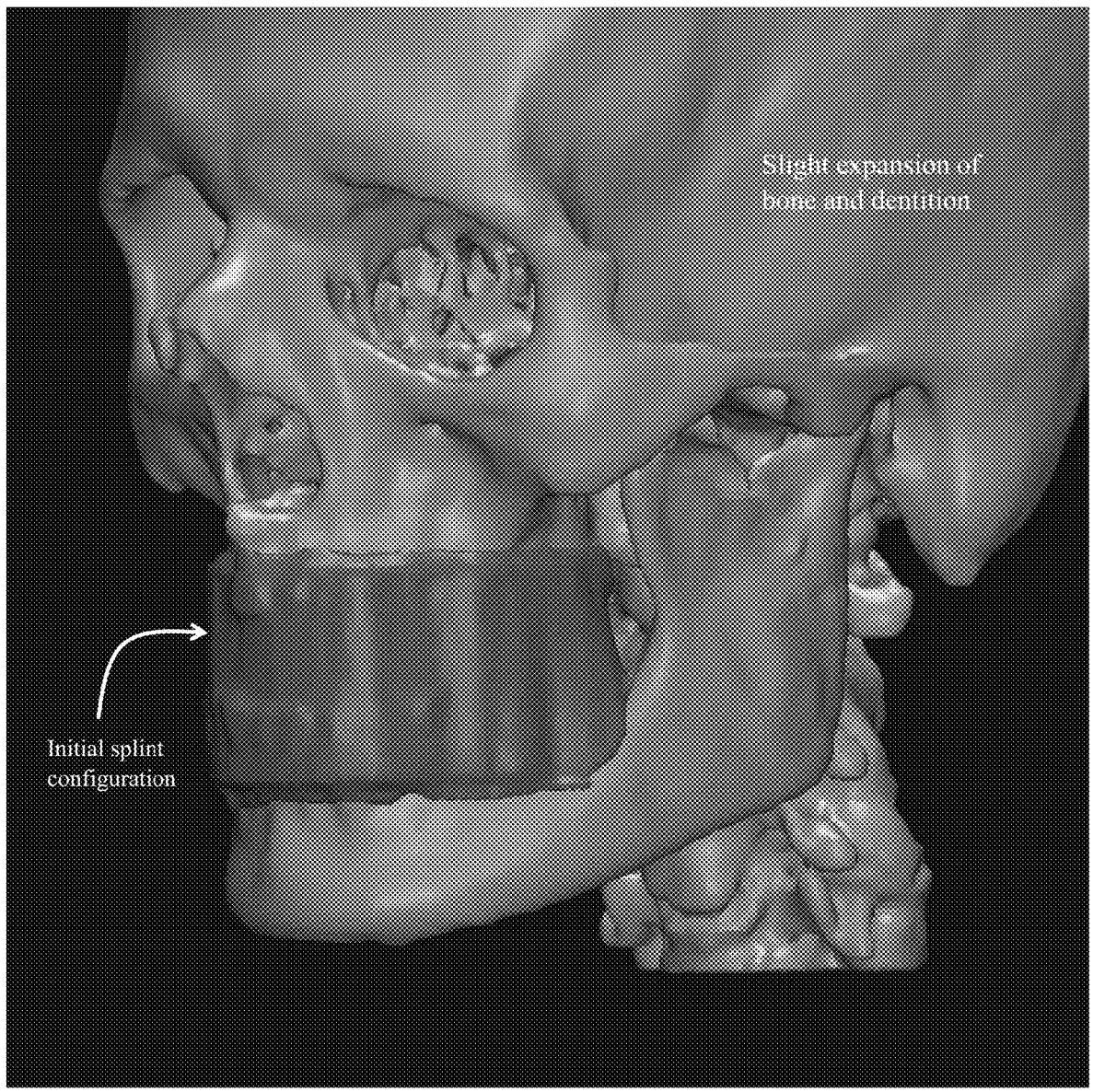
FIG. 5 depicts expansion of the dentition and bone to create space between the blank and the dentition/bone.

From there, the boney and dental three-dimensional (3D) anatomy can be wrapped with a 1-mm detail parameter and/or a "protect thin walls" parameter (e.g., setting that slightly expands the bone, for example 0.5-0.8 mm from its original thickness) to de-feature and slightly expand the bone, as seen in FIG. 5, which, in turn, slightly expands the splint to account for variability and for the gums, and so that the dentition can fit within the splint comfortably but snugly. The purpose of this expansion can be seen most clearly in FIG. 14E, where the splint covers the outside of the dentition. The expansion typically is relatively small, for example between about 1.24 mm and about 2 mm.

Figure 6A:
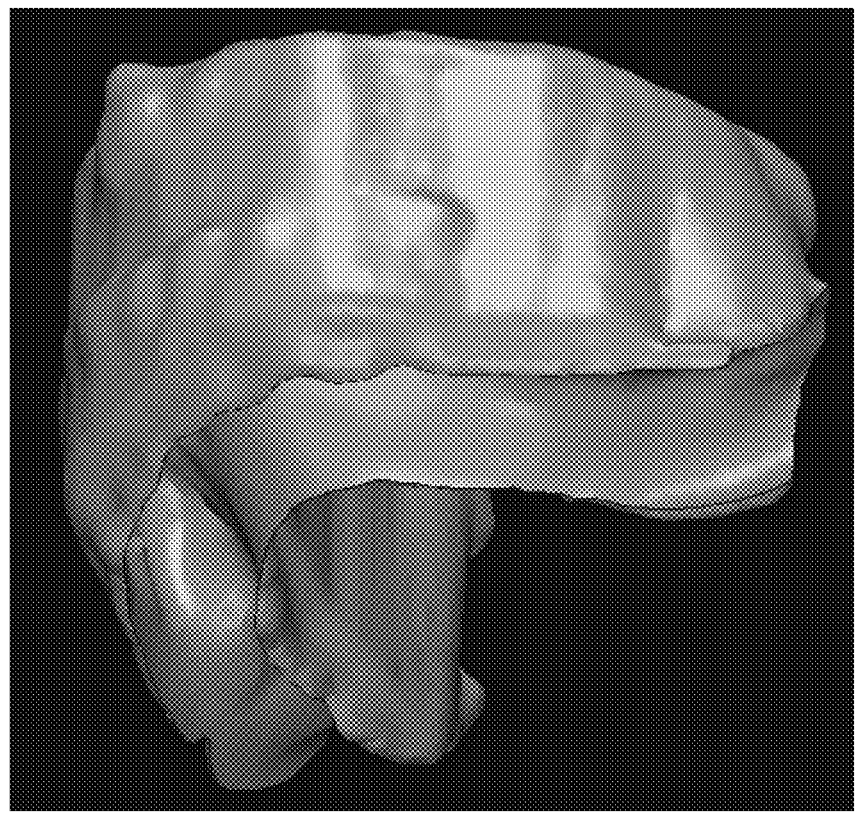
FIG. 6A is a lower perspective view of the blank (initial splint configuration) upon removal of the bone and dentition on the image processing software program.
Figure 6B:
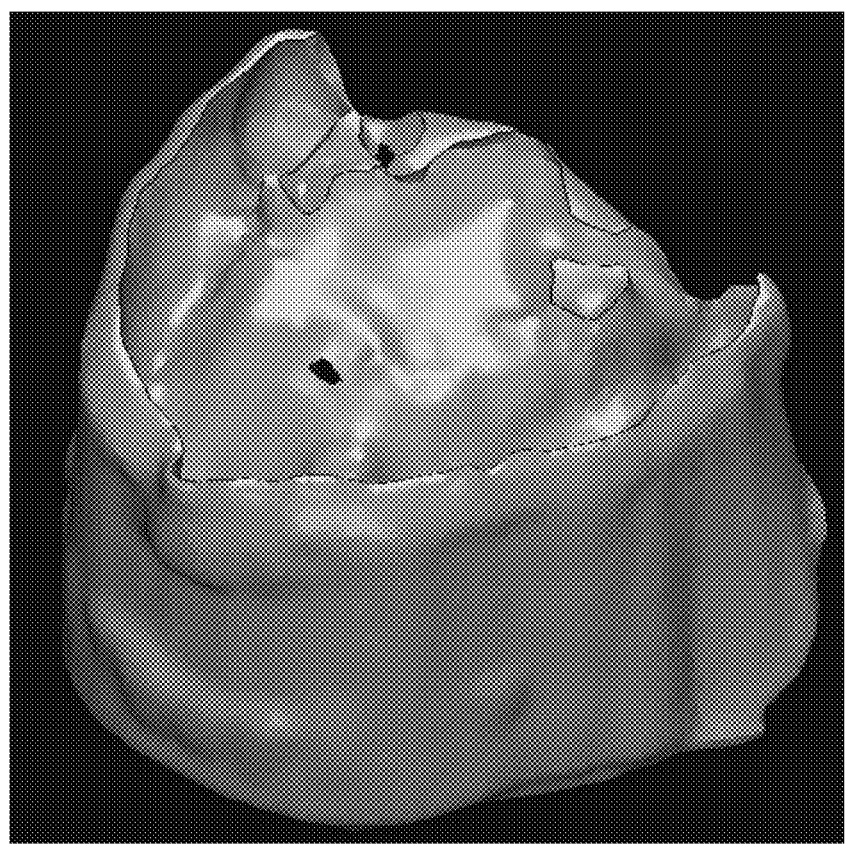
FIG. 6B is an upper perspective view of the blank (initial splint configuration) of FIG. 6A.

Using a Boolean subtraction or other suitable methodology, the bone and any dentition is subtracted from the splint, leaving only an image of the initial splint configuration, as can be seen in FIGS. 6A-6B. The distances of the splint can then be checked and altered to ensure that the lip and tongue frenula are not impacted.

Figure 7:
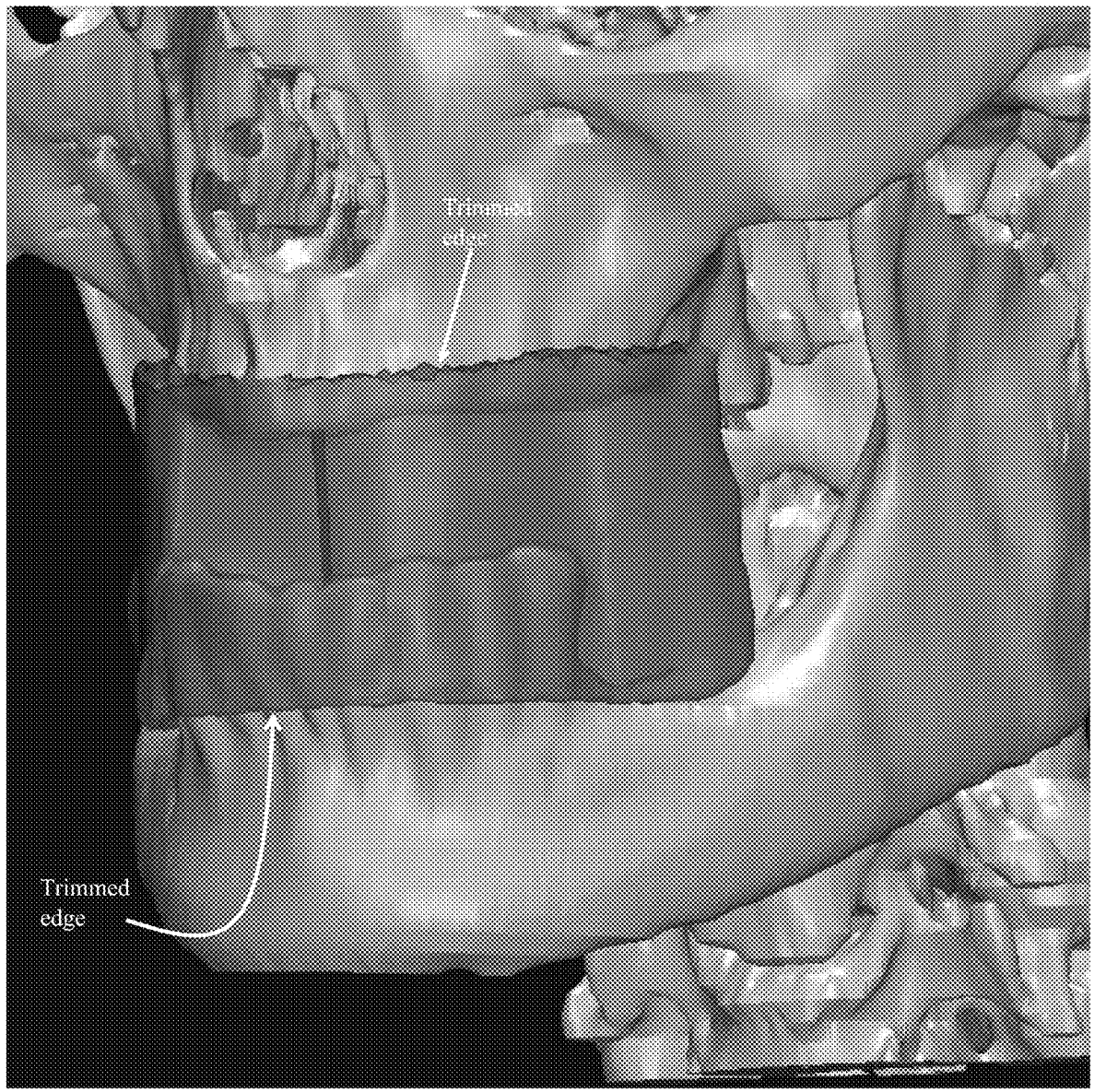
FIG. 7 depicts the initial splint configuration upon trimming for better fit on a subject or patient.

The top and/or bottom edges of the initial splint configuration may be trimmed, as the splint (FIGS. 6A-6B) formed from the interpolation of FIGS. 3A-3C may be oversized or include an excessive amount of the oral cavity. As such, it can be trimmed for better fit, as seen in FIG. 7.

At this point, i.e., upon creation of the image of the initial splint configuration (optionally trimmed for fit, if needed) by itself, the following steps do not necessarily need to be performed in the order presented herein. Any order may be used, as determined by one of ordinary skill in the art, to form the resulting oral splint.

Figure 8A:
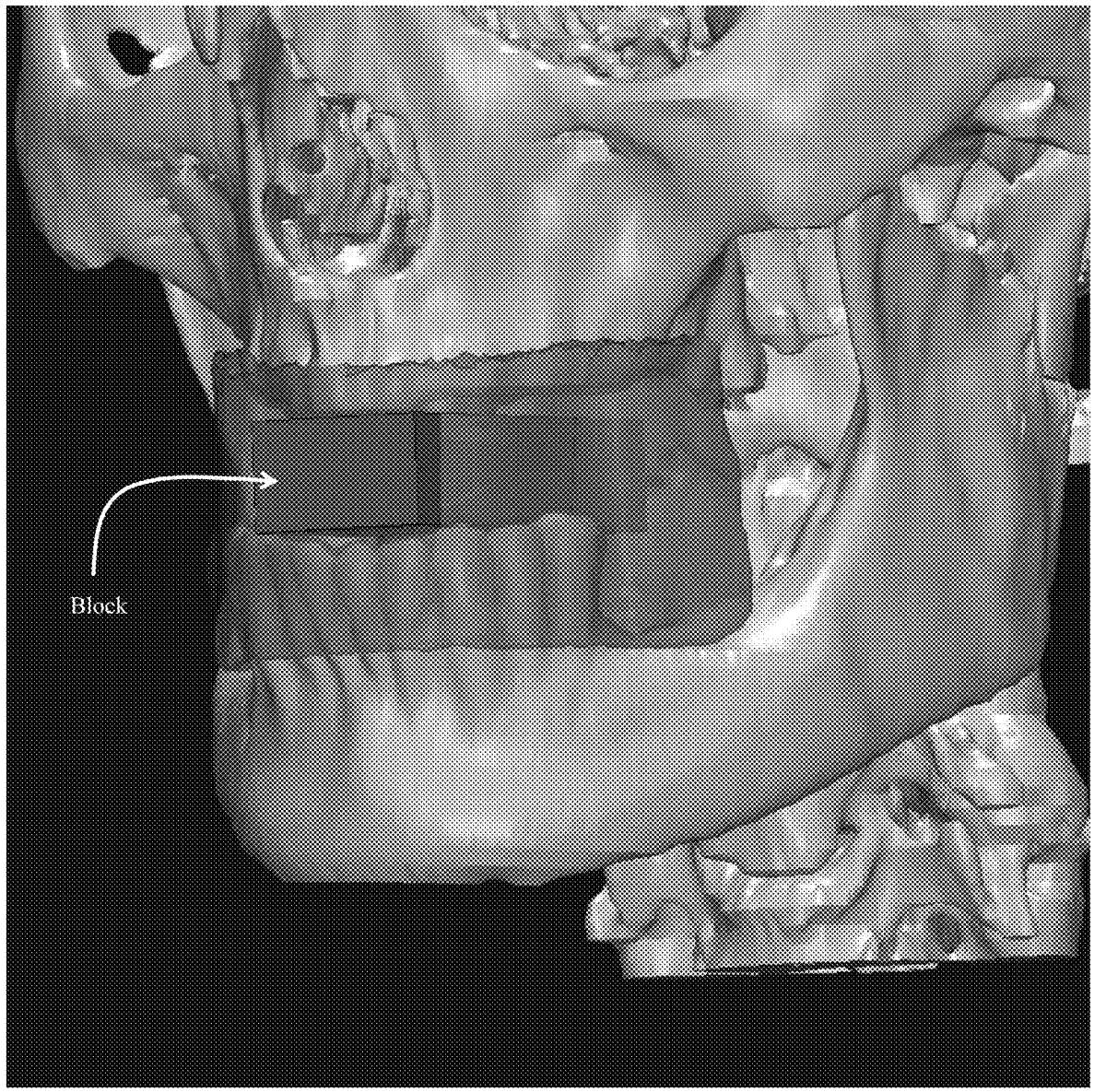
FIG. 8A depicts a rectangular block inserted into the anterior portion/end of the initial splint configuration. Although a rectangular shape is shown herein, any suitable shape (e.g., circular/cylindrical, triangular, asymmetrical or amorphous, etc.) is contemplated herein by the current invention.
Figure 8B:
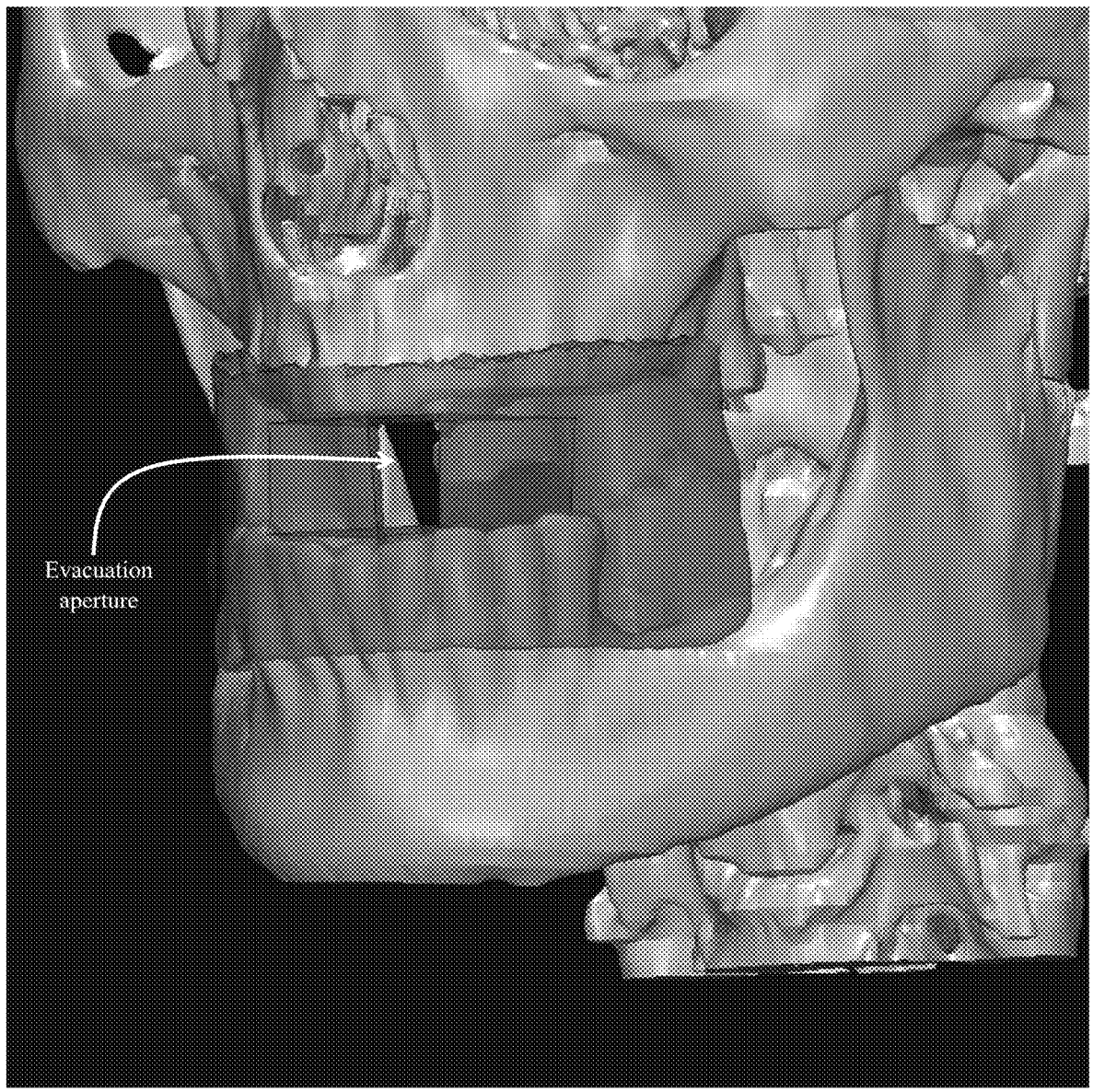
FIG. 8B depicts creation of the evacuation aperture via removal of the block of FIG. 8A.

FIGS. 8A-8B depict formation of an evacuation aperture within an anterior portion/end of the initial splint on the image processing software program. A rectangular block is inserted through the anterior end of the initial splint. Any shape of this block is contemplated herein. When the block is removed, an aperture is formed, as in FIG. 8B. The aperture can be of any suitable size, for example having a 12-mm height and a 20-mm width. The aperture is formed in the anterior portion of the splint to accommodate the suctioning instrumentation or similar device that allows evacuation of oral or gastric contents from the patient as needed, thus preventing aspiration. It is contemplated herein that the aperture can be of any suitable shape and size or may be removed from the design entirely, depending on the needs of the patient.

Figure 9A:
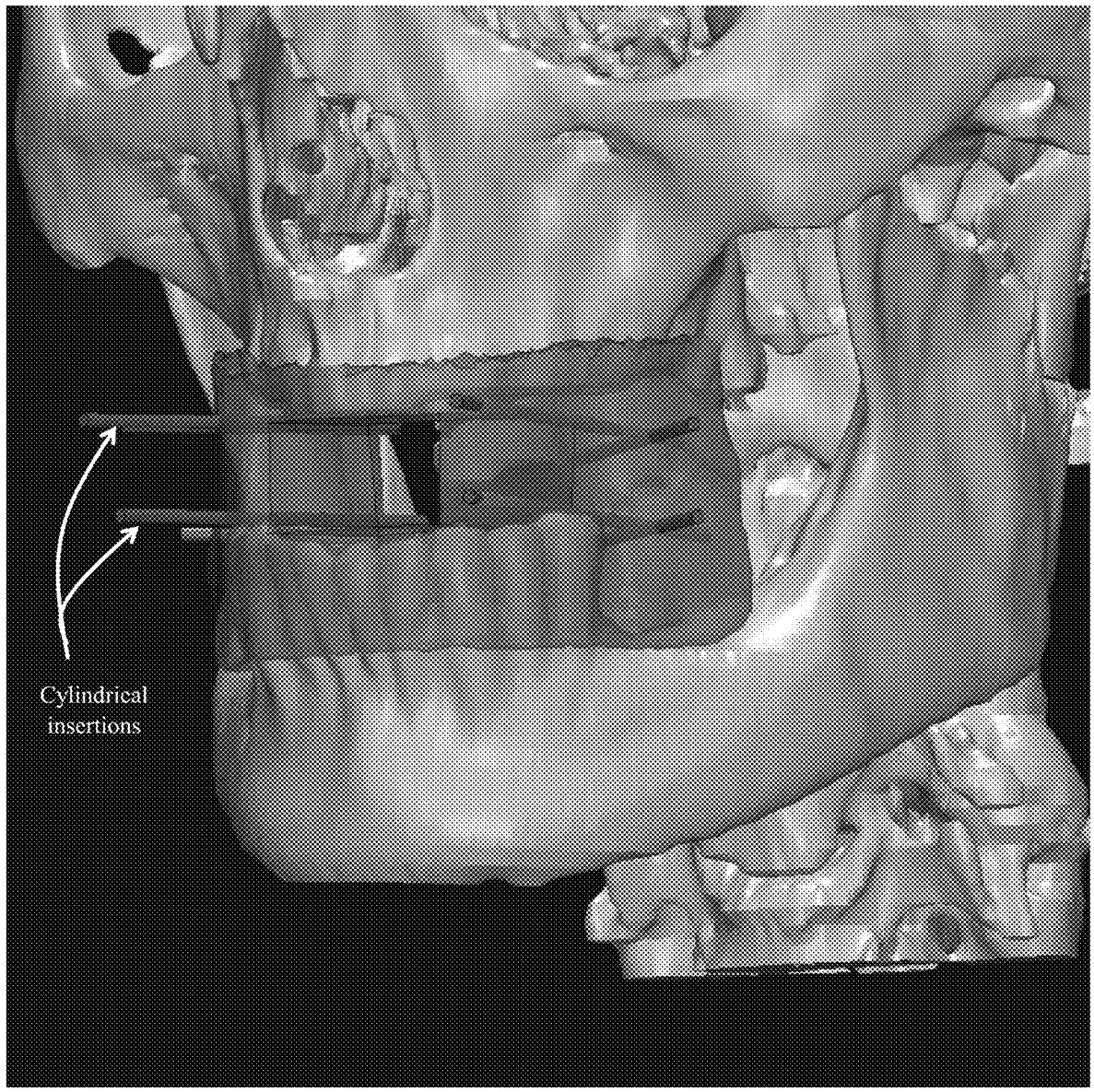
FIG. 9A depicts cylindrical insertions inserted into an anterior side of the initial splint configuration. Although a cylindrical shape is shown herein, any suitable shape (e.g., rectangular, triangular, asymmetrical or amorphous, etc.) is contemplated herein by the current invention.
Figure 9B:
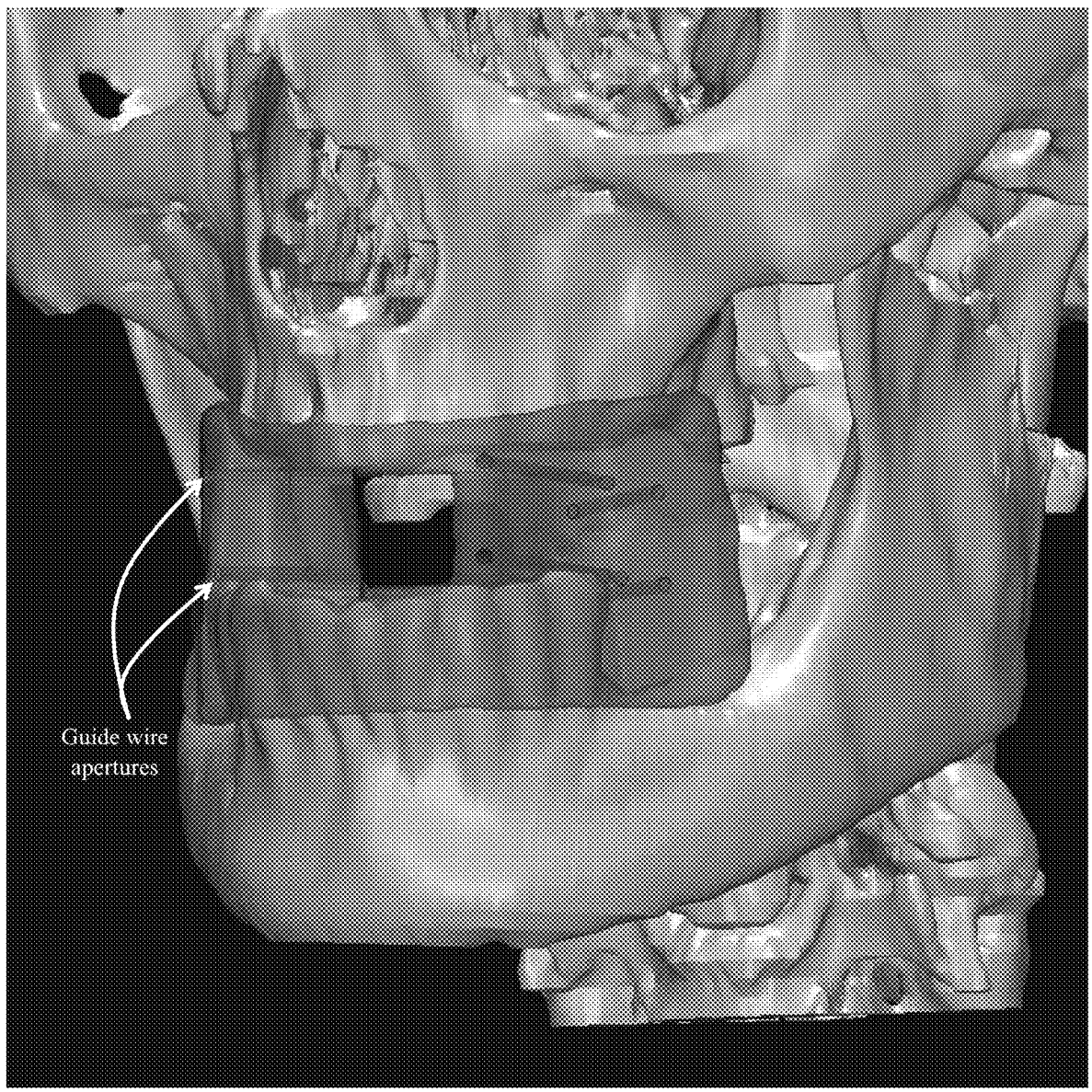
FIG. 9B depicts creation of the guide wire apertures via removal of the insertions of FIG. 9A.

FIGS. 9A-9B depict formation of guide wire apertures within an interior portion of the initial splint on the image processing software program. Cylindrical blocks are inserted through the anterior portion of the initial splint. When the cylindrical blocks are removed, a plurality of small apertures are formed, as in FIG. 9B. It is contemplated herein that there can be any number (e.g., eight) of apertures at any suitable size (e.g., 1.5 mm diameter) and with any suitable shape. Each aperture in the upper half of the initial splint, however, should have a corresponding aperture in the lower half of the initial splint, or vice versa. For example, there may be four (4) apertures in the upper half of the initial splint, and four (4) corresponding apertures in the lower half of the initial splint. These smaller apertures accommodate for wiring. These apertures would be used during installation of each of the maxillary and mandibular splints in order to secure the maxillary splint to the maxilla and secure the mandibular splint to the mandible. This will become clearer as this specification continues.

Figure 10A:
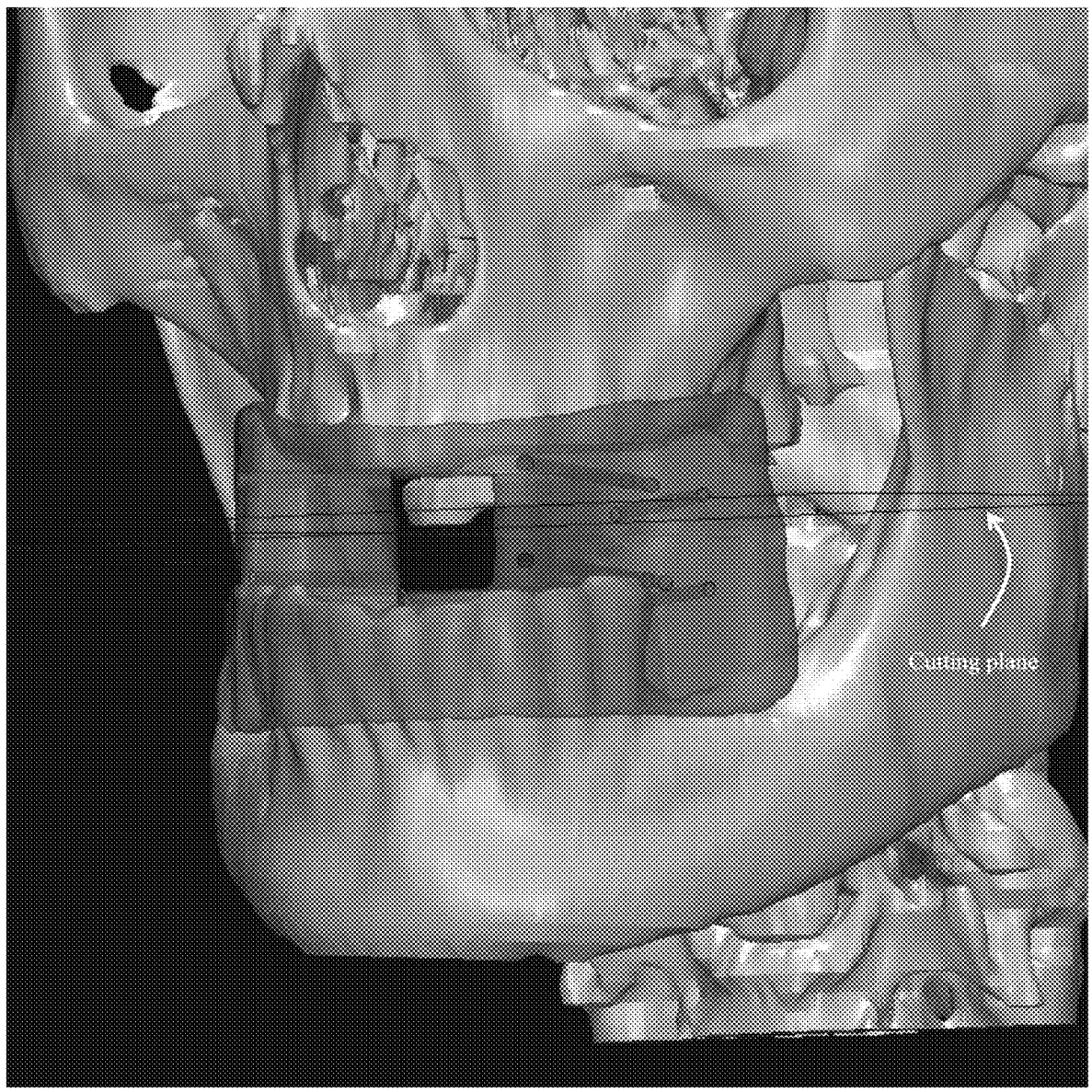
FIG. 10A depicts creation of a cutting plane for splitting the initial splint configuration into an upper (ultimately, maxillary) splint and a lower (ultimately, mandibular) splint.
Figure 10B:
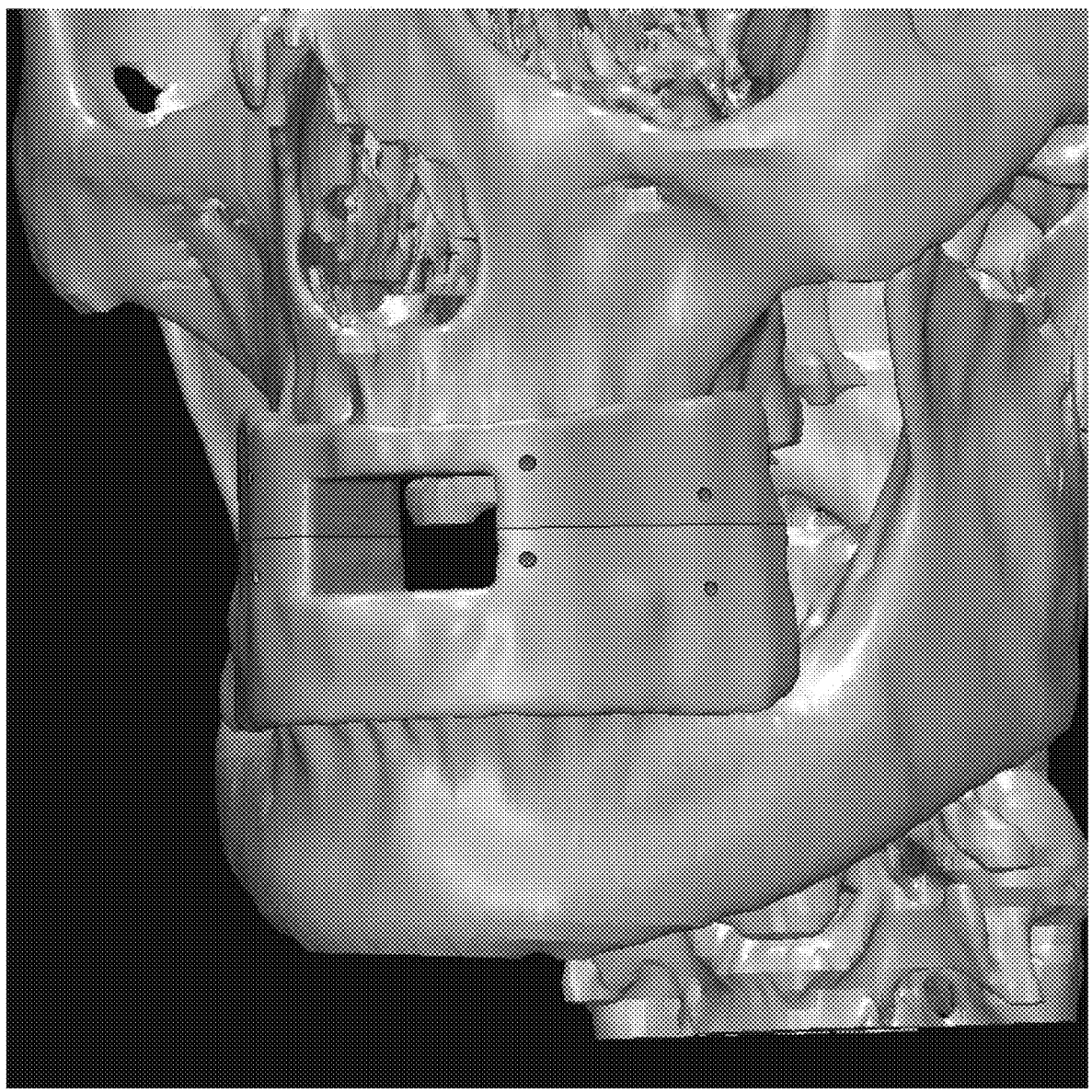
FIG. 10B depicts the splint upon being split by the plane of FIG. 10A.

FIGS. 10A-10B depict splitting of the initial splint into an upper portion (forming the maxillary splint) and a lower portion (forming the mandibular splint). This can be accomplished in any suitable manner. For example, as can be seen in FIG. 10A, an anterior-posterior (horizontal) plane is created somewhere along the midsection of the initial splint to slice the splint into an upper/superior portion, which becomes the maxillary splint, and a lower/inferior portion, which becomes the mandibular splint.

Figure 10C:
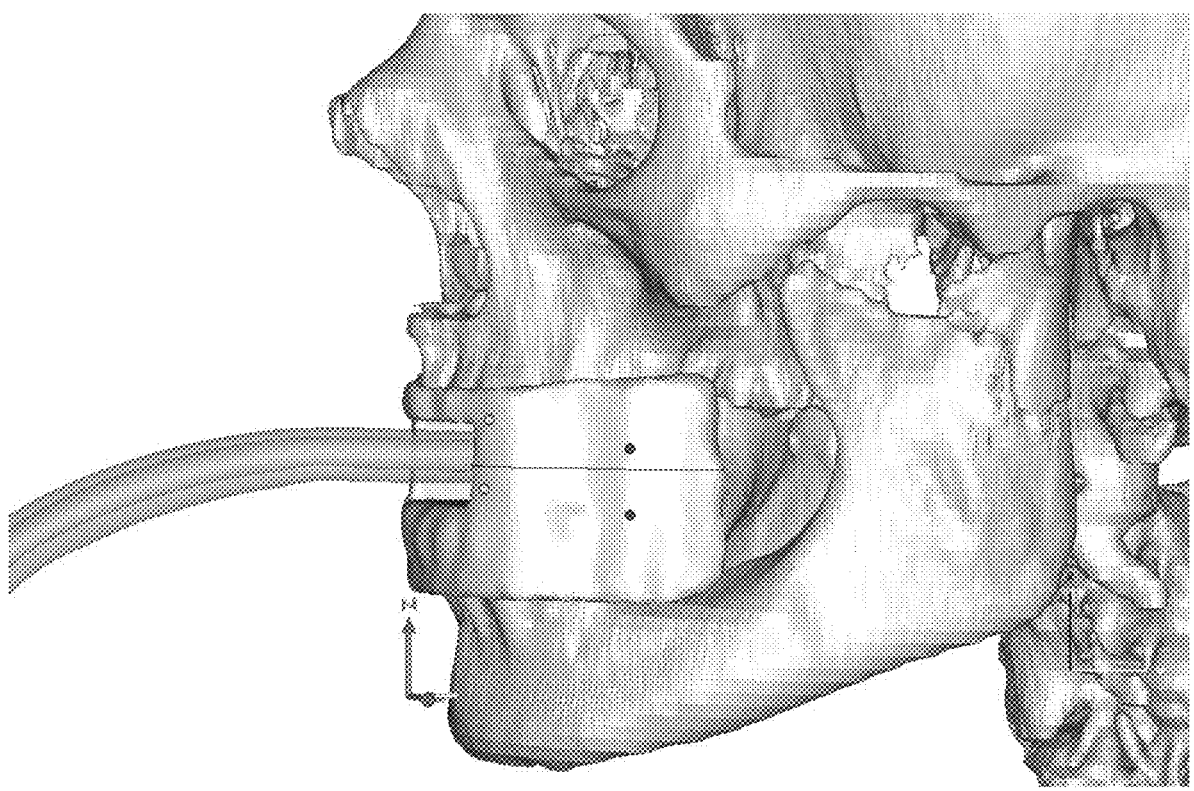
FIG. 10C depicts the split splint with suctioning instrumentation positioned through the evacuation aperture formed in FIG. 9B.

The location of where this plane is created along the midsection of the splint is determined by an average of the number and size of the teeth of the patient population (or subset thereof) along the maxilla and mandible. For example, if the upper teeth and lower teeth are all present and similarly sized, the plane can be created substantially in the middle of the midsection to create two (2) halves. However, if, for example, upper/maxillary teeth are missing, then the plane would be created closer to the upper gum line. FIGS. 10B-10C show this particular example, where the upper portion/maxillary splint can be seen to be shorter in height vertically than the lower portion/mandibular splint. In this particular case, a majority of his/her upper/maxillary teeth was missing. Based on this concept, one of ordinary skill in the art would be able to determine different locations of the plane for slicing or splitting the splint into the upper and lower portions.

FIG. 10B shows the splint after having been split into its upper and lower portions, for example by the anterior-posterior plane of FIG. 10A. FIG. 10C shows the split splint with suctioning instrumentation inserted through the evacuation aperture formed in FIG. 9B.

Figure 11A:
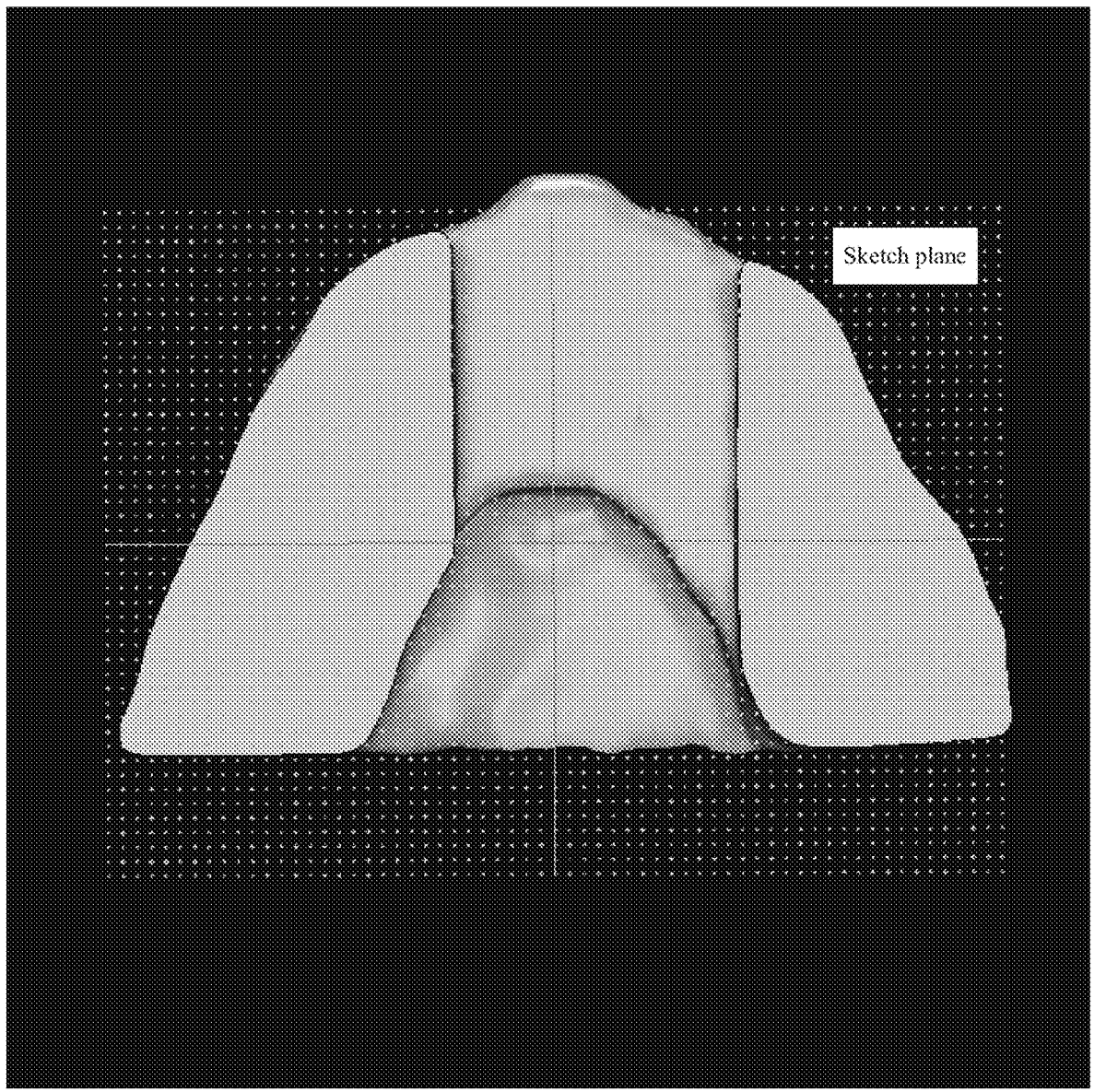
FIG. 11A depicts a sketch plane for creation of structures on the upper and lower splints that facilitate stability and securement of the upper and lower splints when coupled together.

The upper portion of the splint, which becomes the maxillary splint, has a superior/upper side/surface and an inferior/lower side/surface; similarly, the lower portion of the splint, which becomes the mandibular splint, also has a superior/upper side/surface and an inferior/lower side/surface. Structures for stabilizing the upper portion of the splint and the lower portion of the splint together when the splint is "closed" (i.e., when the inferior surface of the upper splint is contacting the superior surface of the lower splint) may be positioned on the inferior surface of the upper splint and the superior surface of the lower splint, respectively. FIG. 11A shows a sketch plane on the inferior surface of the upper splint. The sketch plane is used for drawing out the structure(s) to be placed on the inferior surface of the upper splint, where the structure(s) facilitates stability and securement of the upper and lower splints when coupled together. It can be appreciated that this sketch plane can be used with any surface/side of any of portion of the splint to draw any structure needed.

Figure 11B:
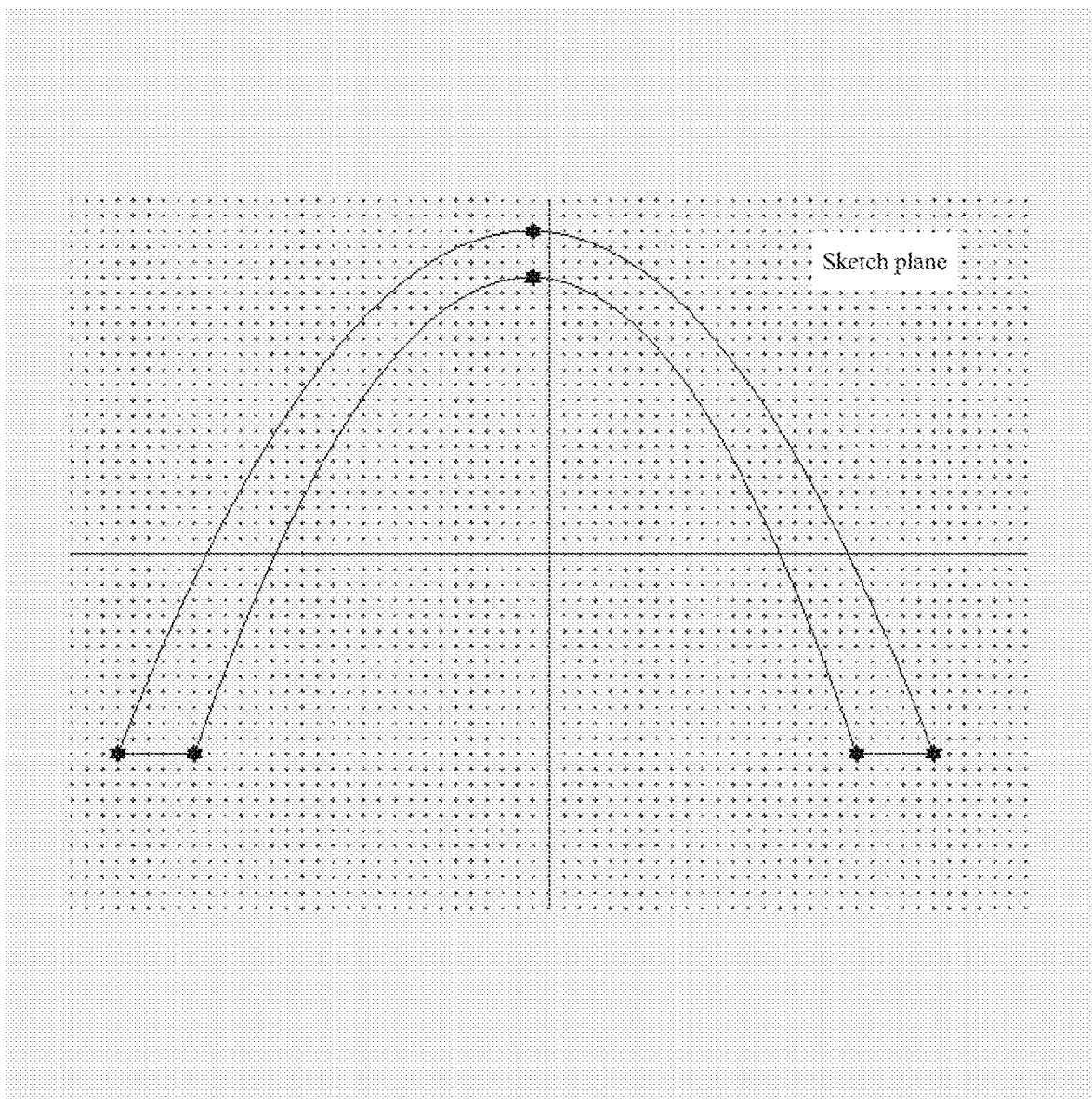
FIG. 11B depicts a drawing of a tongue-and-groove mechanism on the sketch plane of FIG. 11A.
Figure 11C:
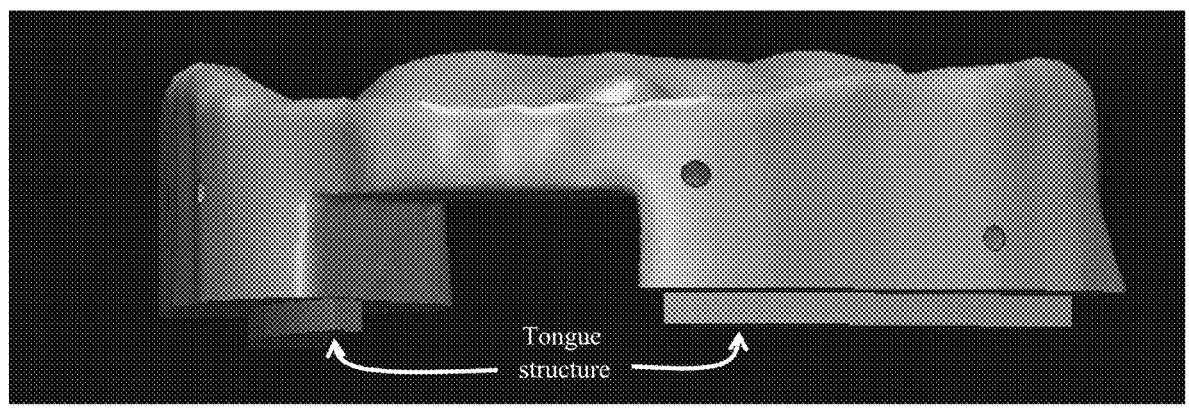
FIG. 11C depicts formation and extrusion of a tongue structure along the upper splint, based on the drawing of FIG. 11B. It is contemplated herein that the tongue structure can be positioned on either the upper splint or the lower splint.

An exemplary mechanism for stabilizing the upper and lower portions of the splint when contacting each other is a tongue-and-groove fitting, which is described herein, though any suitable mechanism is contemplated by the current invention. FIG. 11B shows a U-shaped drawing of the tongue portion of the fitting on the sketch plane of FIG. 11A, resulting in the tongue portion being disposed on the inferior surface of the upper splint, as seen in FIG. 11C. It can be appreciated that the sketch plane and U-shaped drawing could have been positioned on the superior surface of the lower splint, rather than on the inferior surface of the upper splint as in FIGS. 11A-11C; this would result in the tongue portion being disposed on the superior surface of the lower splint. The U-shaped sketch creates an extruded surface (e.g., 2 mm in height), as can be seen in FIG. 11C (and also FIG. 13B where the extruded surface is seen on the superior surface of the lower splint).

Figure 11D:
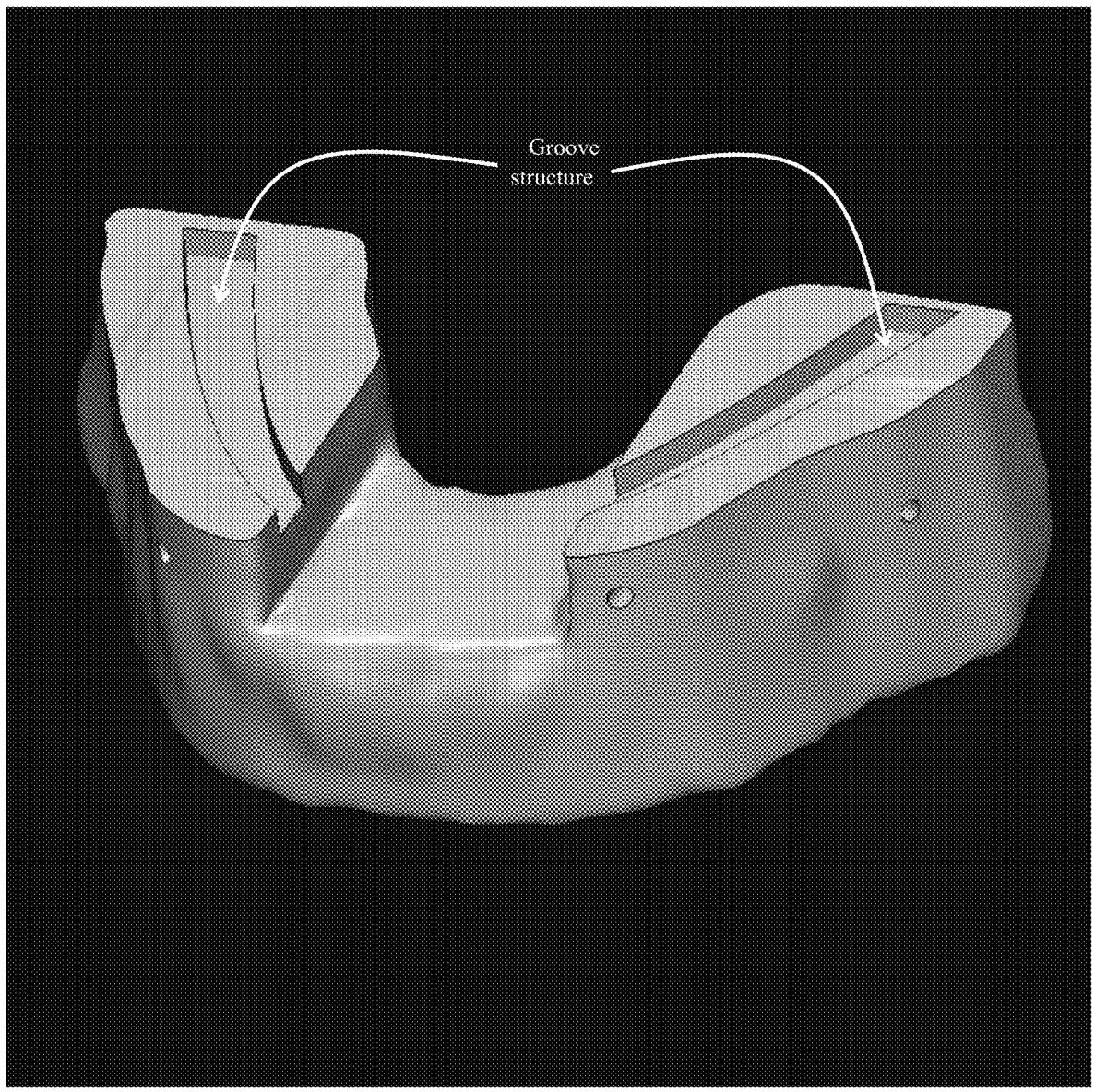
FIG. 11D depicts subtraction and formation of a matching groove structure along the lower splint, positioned opposite from the tongue structure of FIG. 11C. It is contemplated herein that the groove structure can be positioned on either the upper splint or the lower splint, just opposite from where the tongue structure was formed.

In either case, this extruded surface (i.e., tongue portion) is then Boolean or otherwise subtracted from the opposite surface on the opposite portion of the splint. For example, if the extruded surface is created on the inferior surface of the upper (maxillary) portion of the splint, as can be seen in FIG. 11C, then that extruded surface would be subtracted from the superior surface of the lower (mandibular) portion of the splint, as can be seen in FIG. 11D. On the other hand, if the extruded surface is created on the superior surface of the lower (mandibular) portion of the splint (see FIGS. 13B-13C), then that extruded surface would be subtracted from the inferior surface of the upper (maxillary) portion of the splint (see FIGS. 13D-13E). In either case, though, the extruded surface forms the tongue portion of the fitting, and the opposing subtraction forms the groove portion of the fitting, thus creating a tongue-and-groove fitting/mechanism between the upper and lower splints.

FIGS. 12A-12E depict fabrication of projections on the anterior face/surface of the upper and lower splints, where the projections facilitate the upper and lower splints being secured to one another stably. FIG. 12F depicts use of an example of these securement projections by lassoing or wrapping with intersplint wires. This will become clearer as this specification continues.

Figure 12A:
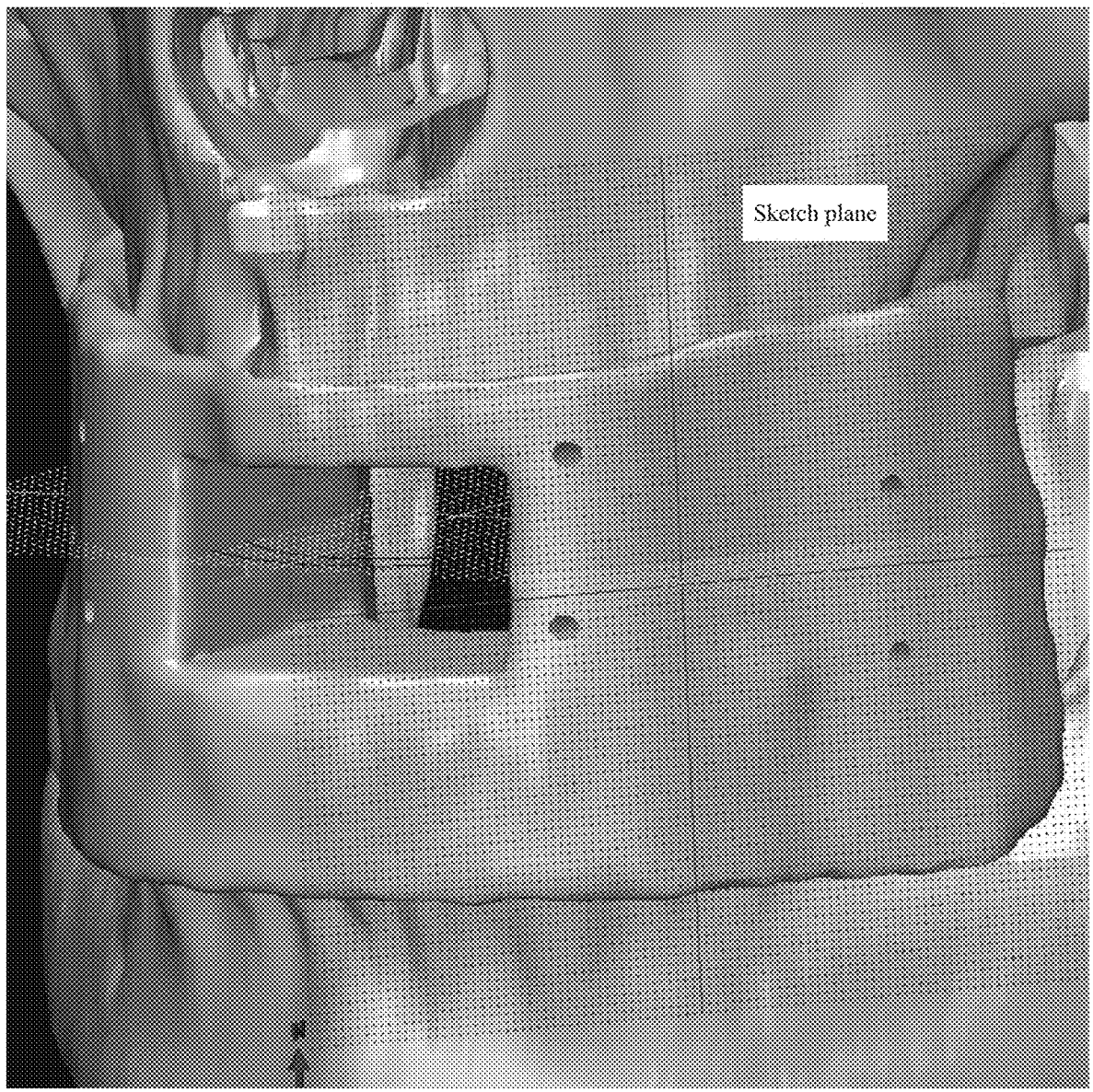
FIG. 12A depicts a sketch plane for creation of structures on the upper and lower splints that facilitate stability and securement of the upper and lower splints when coupled together.

FIG. 12A shows a sketch plane on the anterior surface of the splint. The sketch plane is used for drawing out the structure(s) to be placed on the anterior surface of the splint, where the structure(s) facilitates securement of the upper and lower splints when coupled together. It can be appreciated that this sketch plane can be used with any surface/side of any of portion of the splint to draw any structure needed. These structures typically are projections can be positioned on each of the upper (maxillary) and lower (mandibular) splints along the anterior surface of the splints. For example, a projection (e.g., a stud) can be positioned on each side of the evacuation aperture that was created in FIGS. 9A-9B. In this case, the projection can be any shape or form on the maxillary splint on each side of the evacuation aperture and also on the mandibular splint on each side of the evacuation aperture. The projections on each side of the evacuation aperture should align with each other from the maxillary splint to the mandibular splint, so that intersplint wires can be lassoed or tied around them to secure the maxillary and mandibular splints together.

Figure 12B:
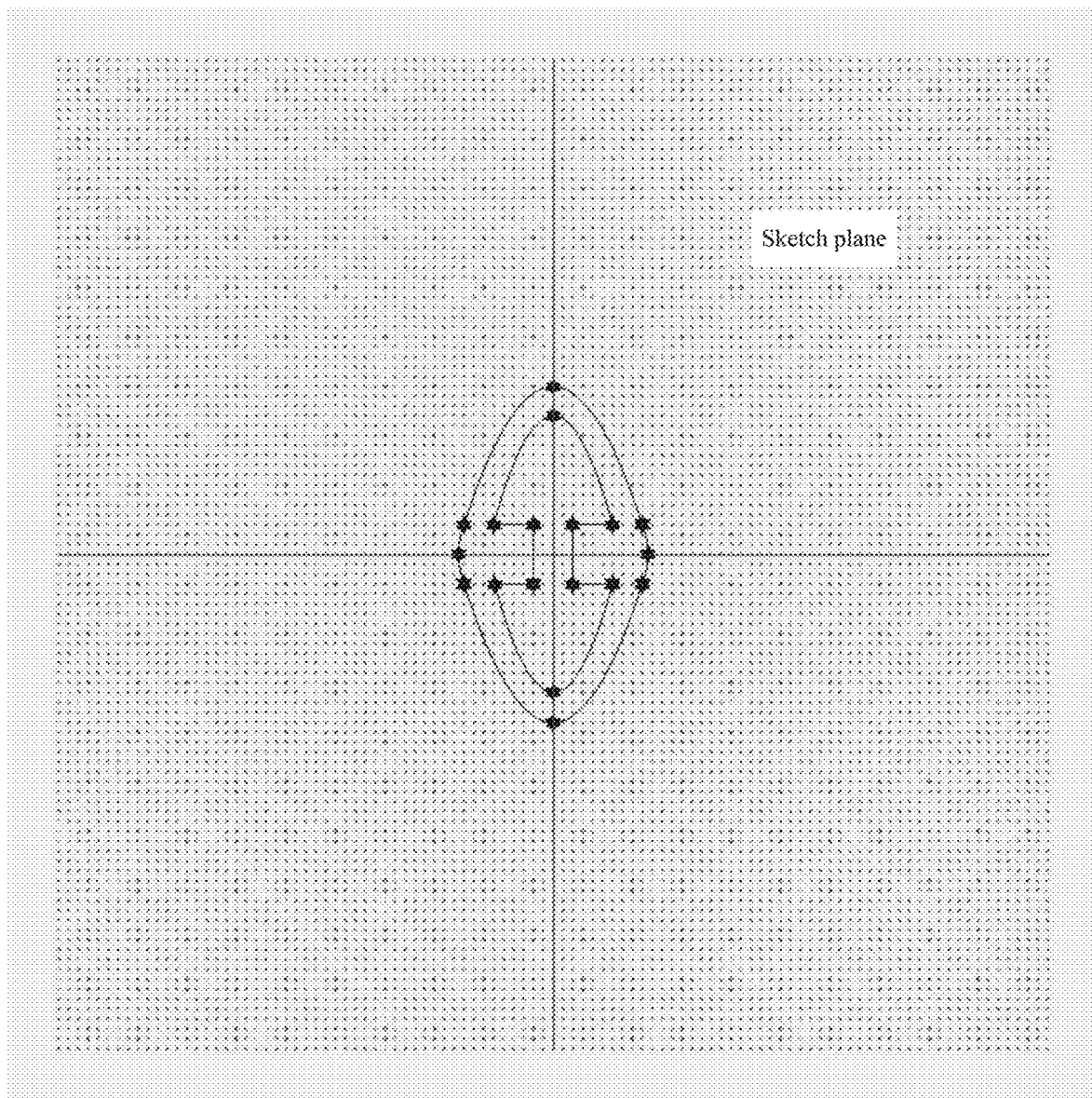
FIG. 12B depicts a drawing of an oval-shaped projection on the sketch plane of FIG. 12A. Although an oval-shaped projection is shown herein, any suitable shape or structure (e.g., studs, rectangular, etc.) is contemplated herein by the current invention, as long the structure(s) positioned on the upper and lower splints facilitates stability and securement of the upper and lower splints when coupled together.
Figure 12C:
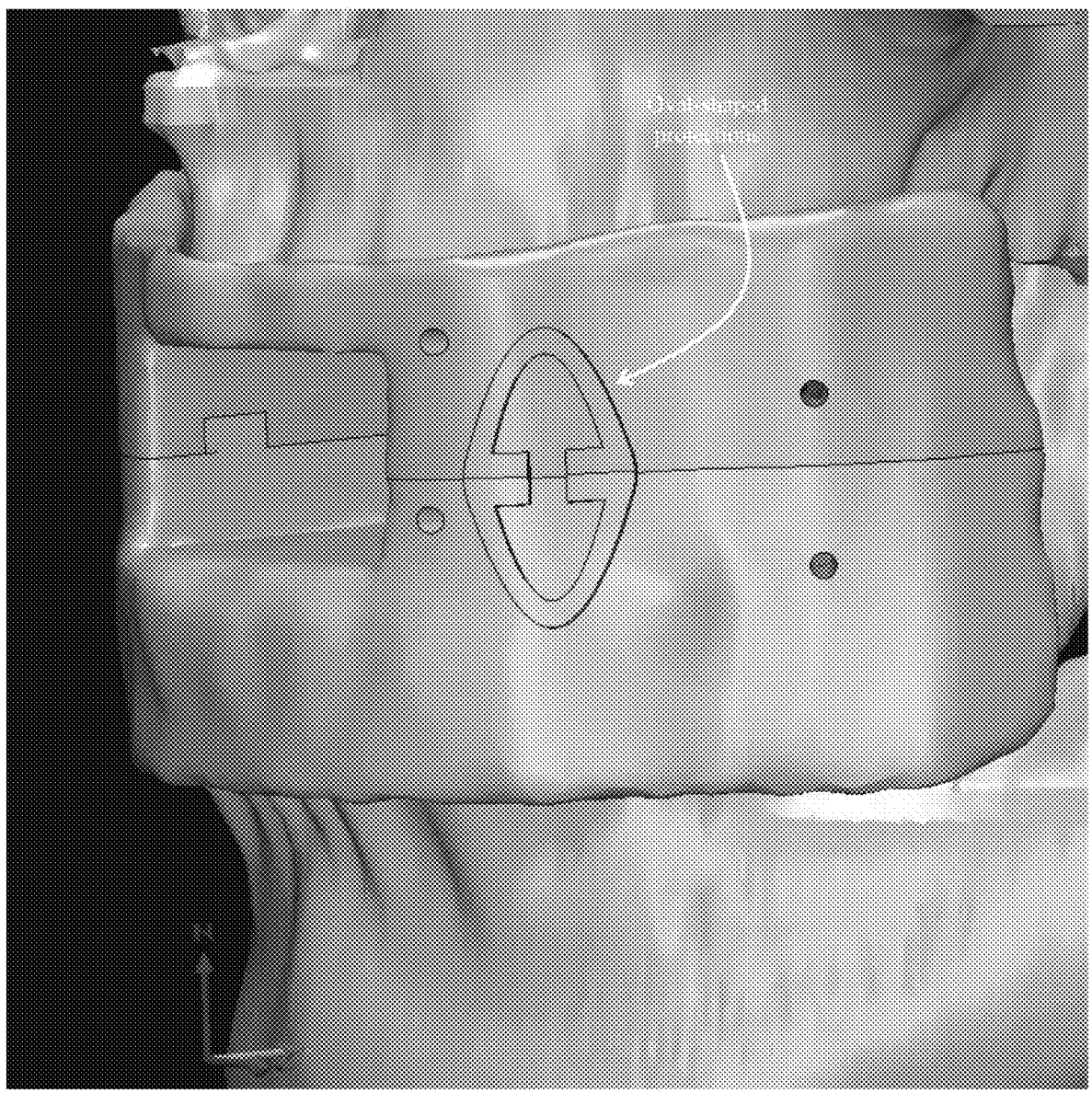
FIG. 12C depicts formation and extrusion of the oval-shaped projection on the upper and lower splints, based on the drawing of FIG. 12B, where an upper/superior portion of the oval-shaped projection is positioned on the upper splint and a lower/inferior portion of the oval-shaped projection is positioned on the lower splint.
Figure 12D:
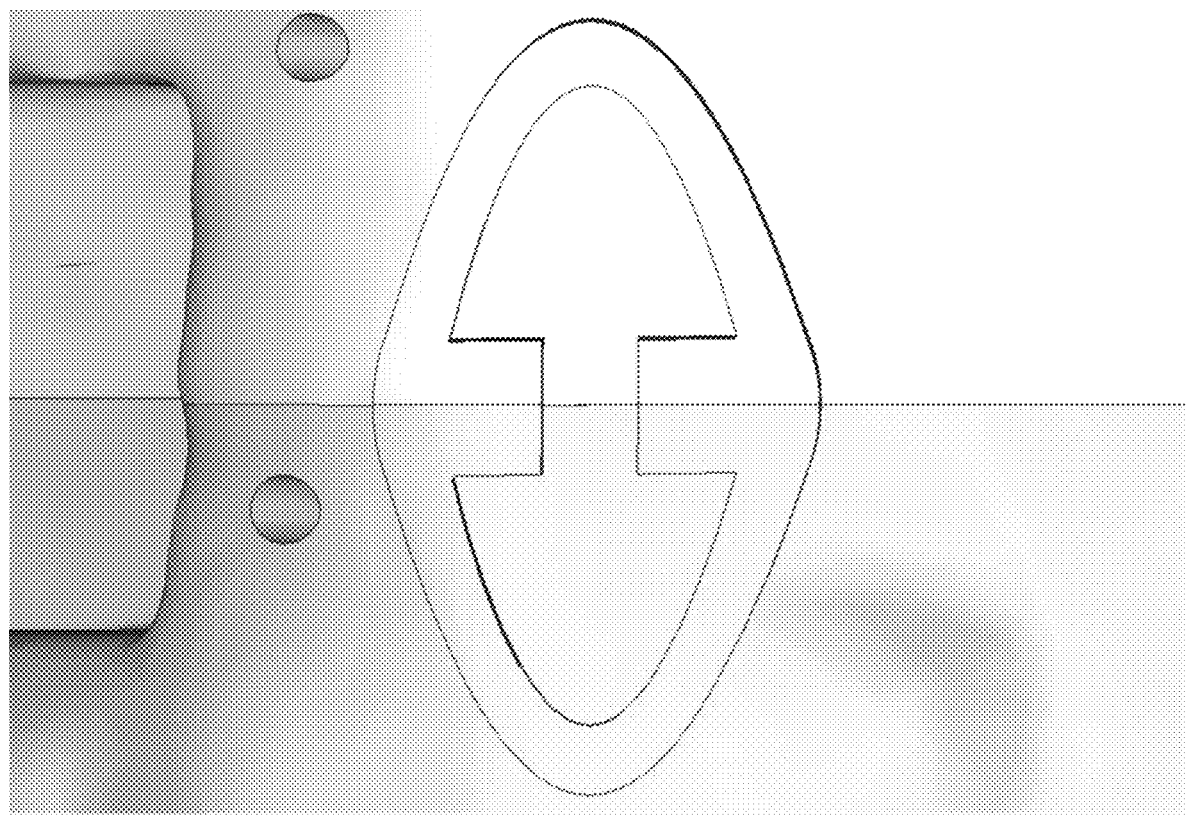
FIG. 12D is a close-up view of the projection of FIG. 12C. Typically, the projection is mirrored on the opposite side of the splint as well.
Figure 12E:
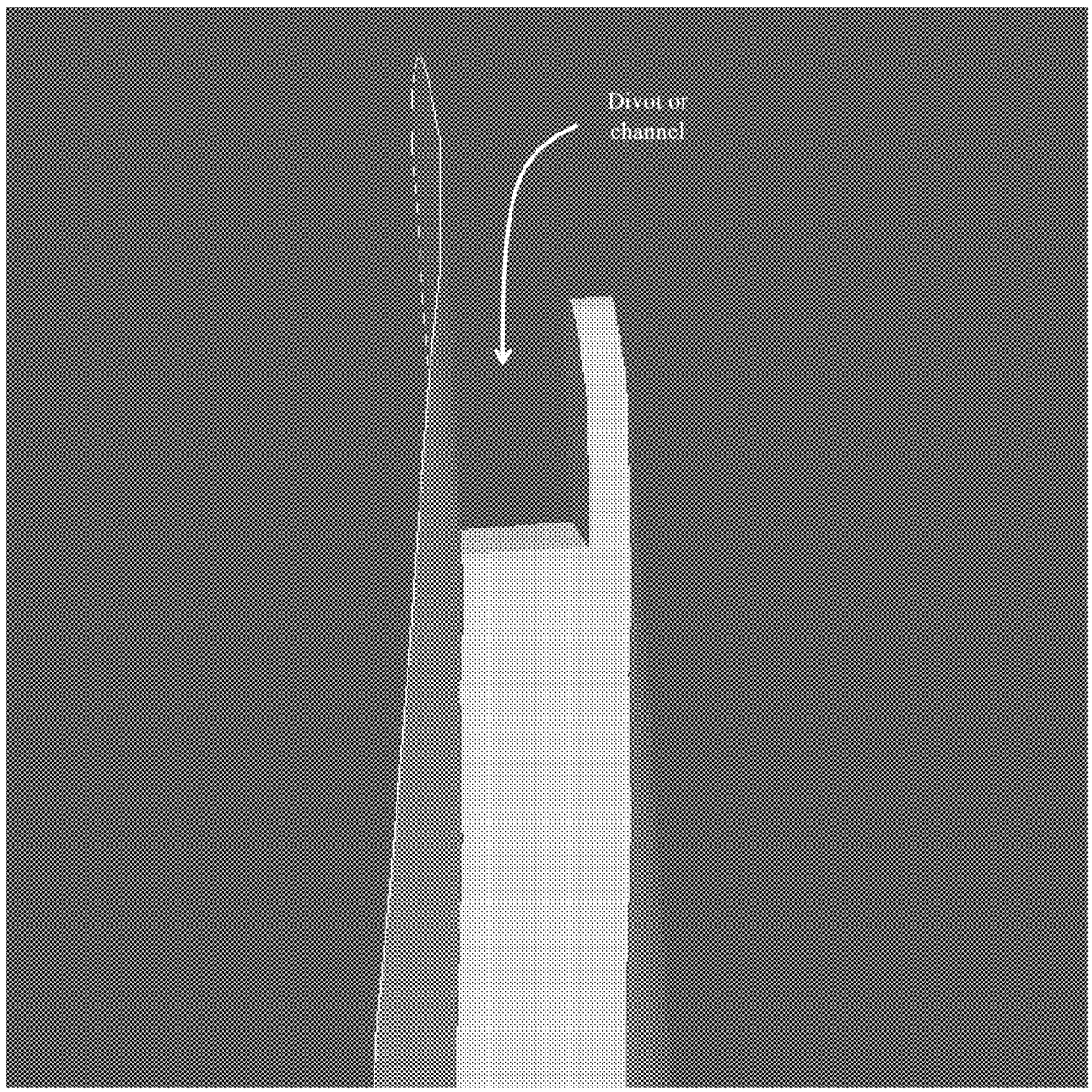
FIG. 12E is a side view of the projection of FIG. 12D showing a divot formed therein to accommodate intersplint wires. The divot is formed by removing sections of the superior and inferior projections to create the lip or divot for wiring.
Figure 12F:
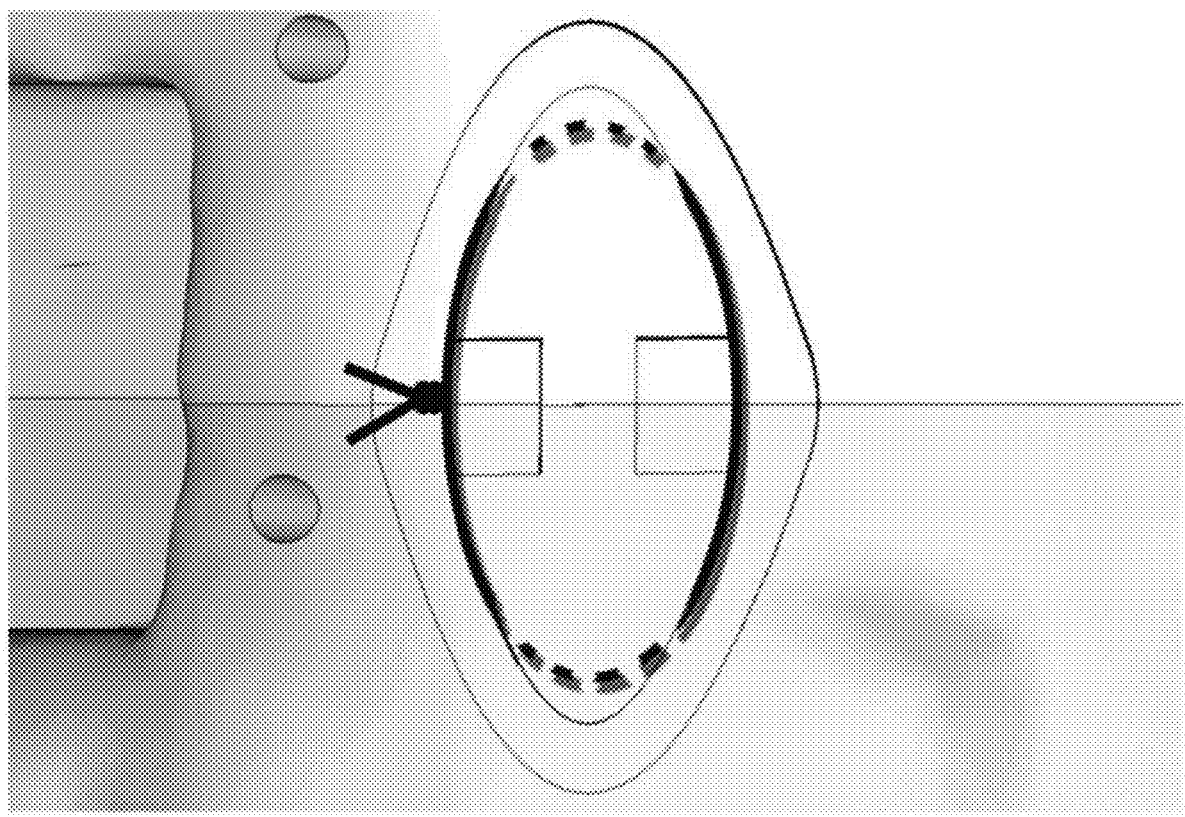
FIG. 12F depicts the projection and divots of FIGS. 12D-12E lassoed with an intersplint wire loop to secure the maxillary splint to the mandibular splint.

As an example of these projections, seen in FIGS. 12B-12F, two recessed ovular protrusions are created on the anterior surface of the splint to allow for anchoring of the upper and lower splints together (FIG. 12F). FIG. 12B shows an oval-shaped drawing of the projection on the sketch plane of FIG. 12A, resulting in the projection being disposed on the anterior surface of the upper and lower splints, as seen in FIG. 12C. It can be appreciated that the sketch plane and drawing can have any suitable shape or size. The oval-shaped sketch creates an extruded surface, as can be seen in FIGS. 12C-12E.

FIG. 12E depicts creation of a divot or recess within the projection to accommodate wiring. The divot or recess is formed by removing sections of the upper and lower projections to create the lip for confining or holding the intersplint wiring. As such, when wiring is lassoed or wrapped around the projection as in FIG. 12F, the upper and lower splints can be held together firmly. The channels of FIG. 12E also permit easy access to cut the intersplint wires, if needed, in order to separate the upper and lower splints from each other.

Figure 13A:
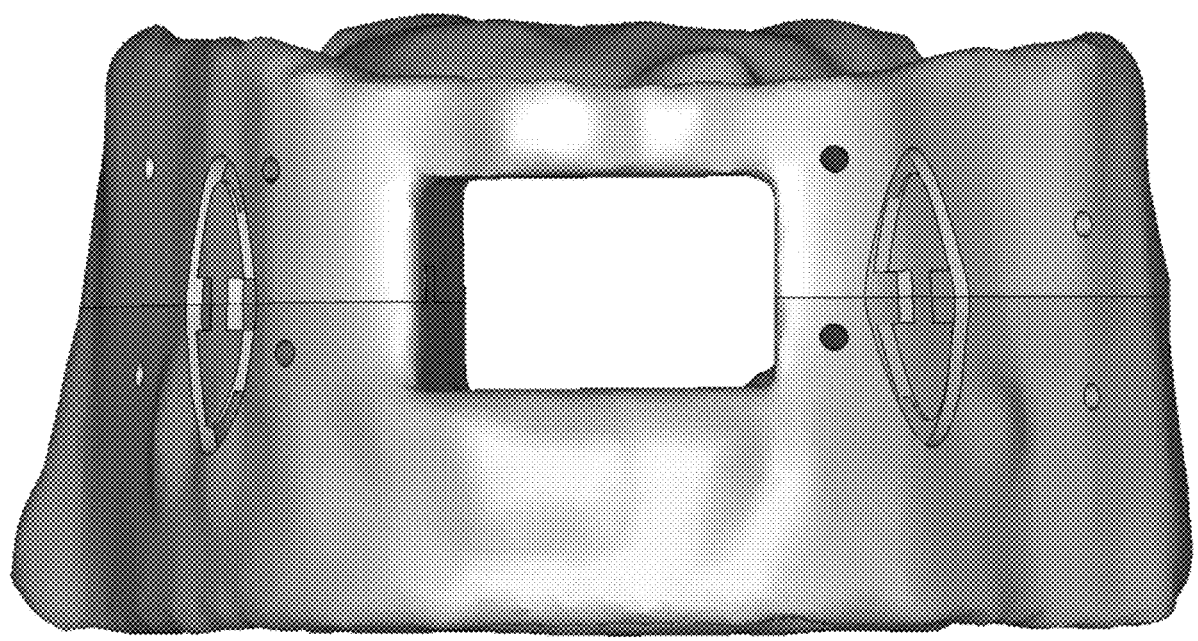
FIG. 13A is an elevated front view of an assembled oral splint according to an embodiment of the current invention.
Figure 13B:
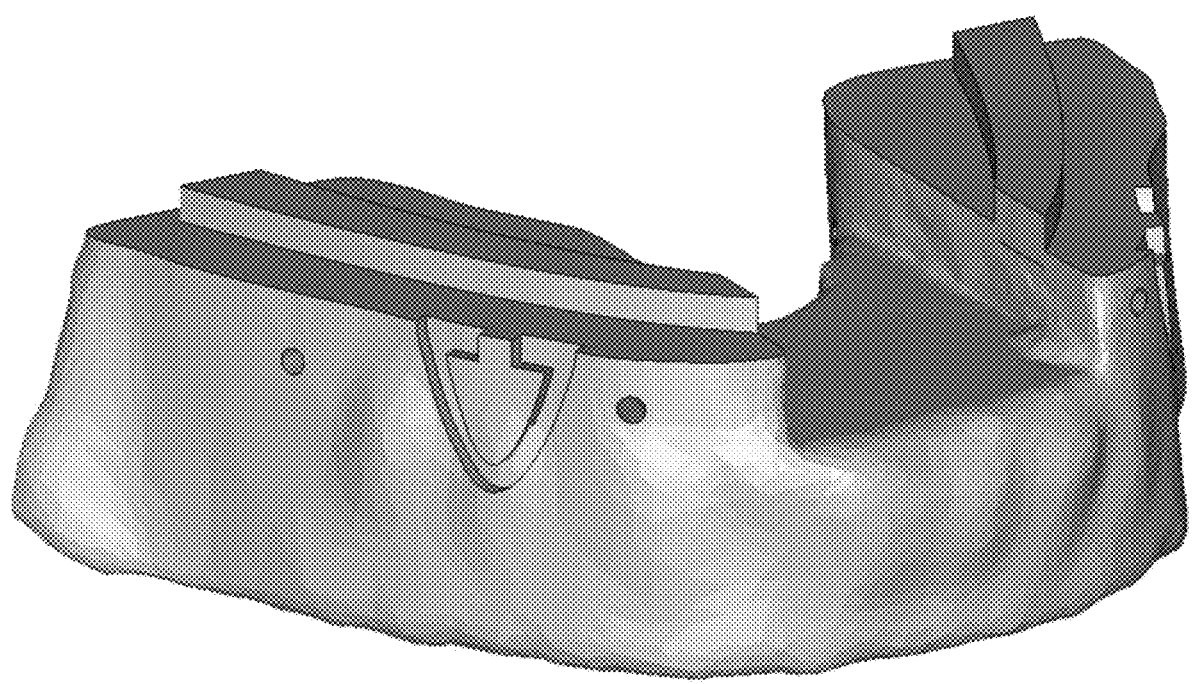
FIG. 13B is a perspective superior view of a mandibular splint of the oral splint of FIG. 13A. It should be noted that the tongue structure is positioned on the mandibular splint in this figure, rather than on the maxillary splint as in FIG. 11C.
Figure 13C:
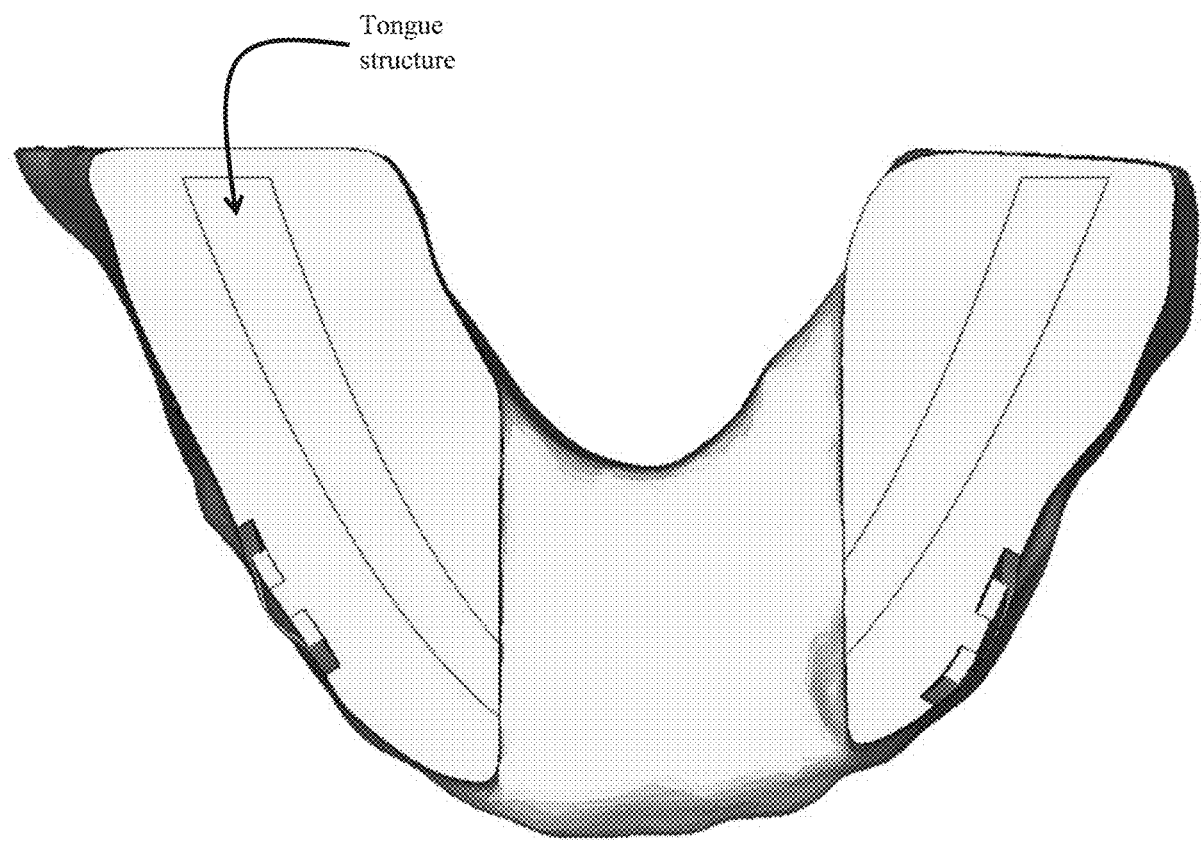
FIG. 13C is a top superior view of the mandibular splint of FIG. 13B.
Figure 13D:
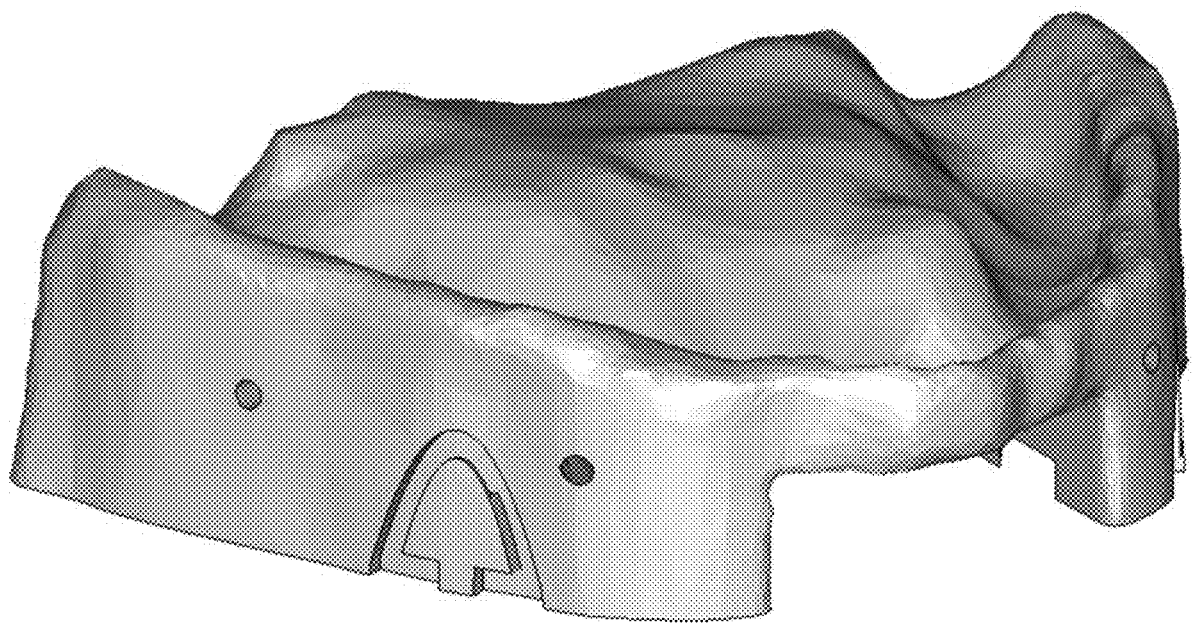
FIG. 13D is a perspective superior view of a maxillary splint of the oral splint of FIG. 13A. It should be noted that the groove structure is positioned on the maxillary splint in this figure (seen by the absence of the tongue structure), rather than on the mandibular splint as in FIG. 11D.
Figure 13E:
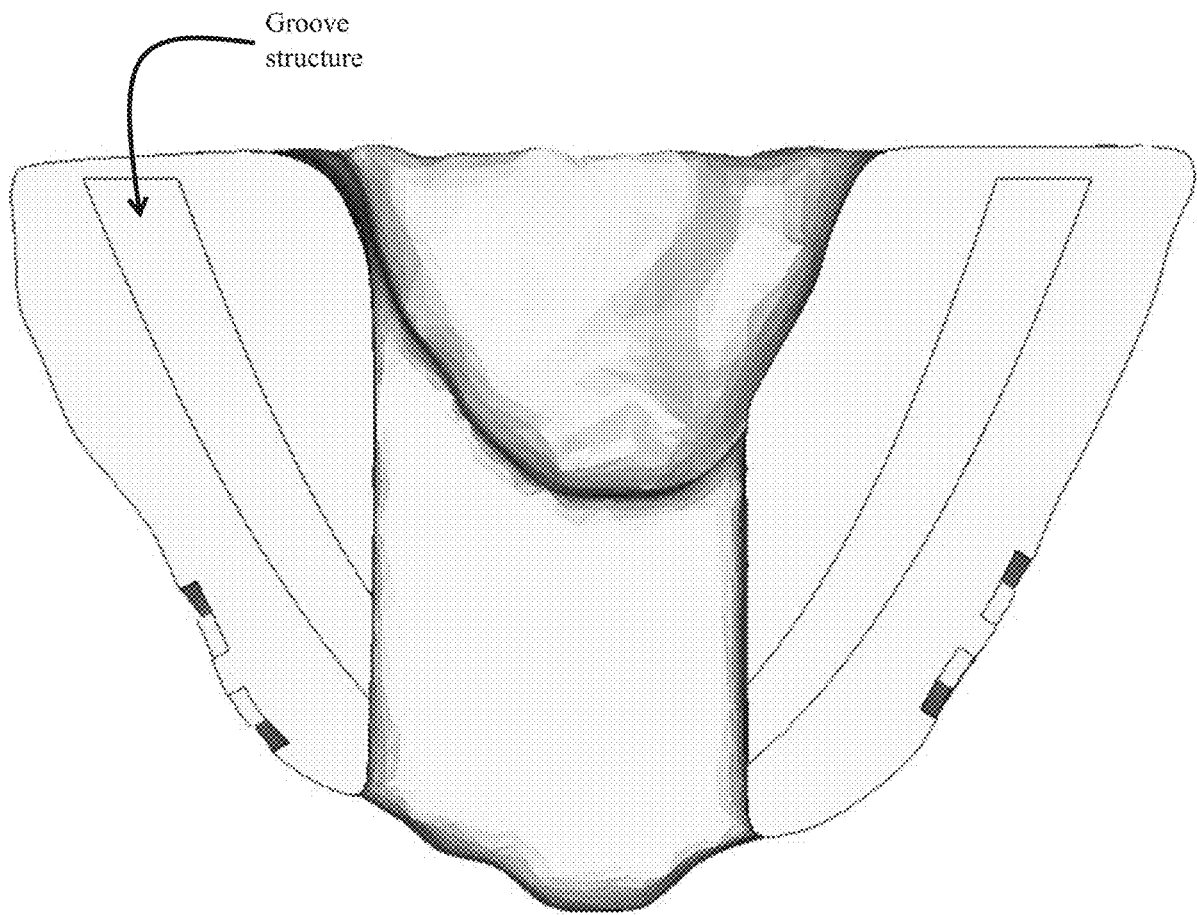
FIG. 13E is a bottom inferior view of the maxillary splint of FIG. 13D.

FIGS. 13A-13E are various views of the resulting virtual image of the splint. FIG. 13A depicts the maxillary and mandibular splint in a closed position. FIGS. 13B-13C depict the mandibular splint with tongue portion disposed thereon, and FIGS. 13D-13E depict the maxillary splint with corresponding groove portion disposed therein.

FIGS. 14A-14E are various views of the splint image in application on a human jaw, both in an exterior view and in a semi-transparent view so that the splint can be seen in comparison to the jaw.

Figure 15:
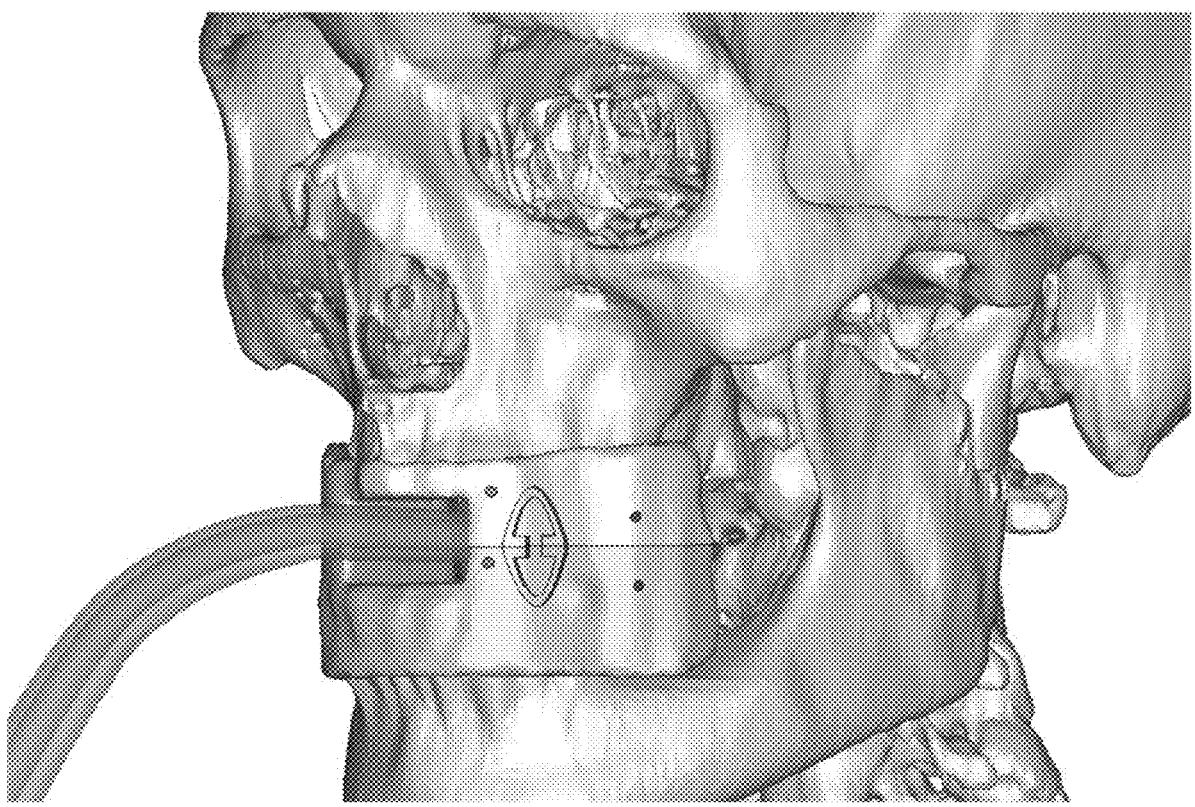
FIG. 15 is a perspective view of an application of an oral splint—resulting from an exemplary methodology according to an embodiment of the current invention—on a human jaw with suctioning instrumentation inserted through the evacuation aperture.

FIG. 15 depicts application of the oral splint, resulting from the methodology described herein, on a human jaw with suctioning instrumentation inserted through the evacuation aperture.

Figure 16A:
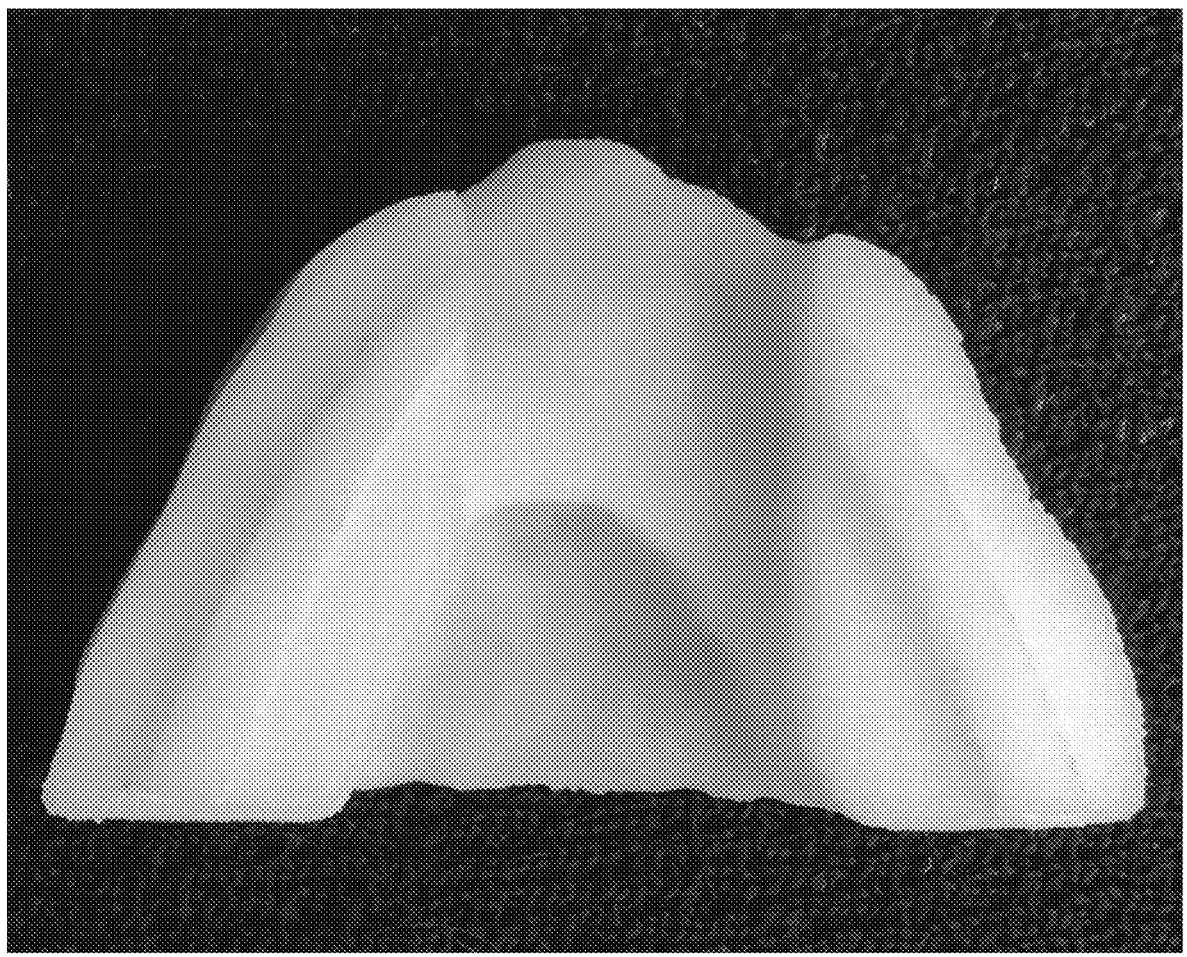
FIG. 16A is a superior view of an exemplary mandibular splint resulting from an embodiment of the novel technique used to fabricate the oral splint.
Figure 16B:
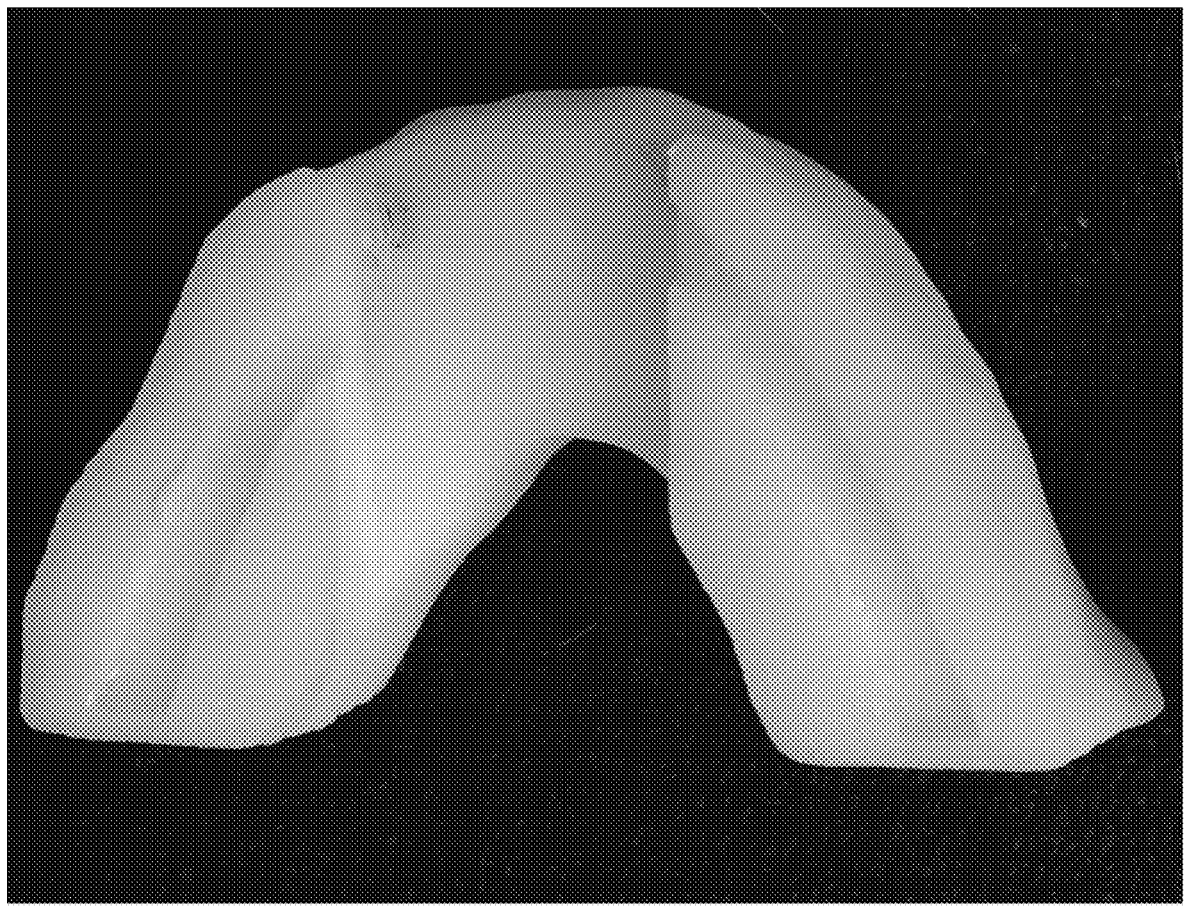
FIG. 16B is an inferior view of an exemplary maxillary splint resulting from an embodiment of the novel technique used to fabricate the oral splint.

Once the resulting splint model (including the maxillary and mandibular splints, tongue and groove fittings/mechanisms, any apertures and/or projections, etc.) is created in virtual space (i.e., on the image processing software), the image can be double-checked and smoothed to prevent any sharp edges from hurting the end-patient. The model can then be exported and sent to a 3D printer for printing into a physical apparatus, seen in FIGS. 16A-16B, for use by the patient. Once printed, the splint can be sanded to ensure a smooth surface.

Selection of Standardized Reduction Splint for Edentulous Patients

The posterior transverse width of the mandible and maxilla are obtained clinically or radiographically. On the mandible, the measurement is specifically the distance from the posterior body segment of the mandible anterior to the ramus on the left to the posterior body segment of the mandible anterior to the ramus on the right. On the maxilla, the measurement is specifically the distance from the left posterior edge of the alveolus to the right posterior edge of the alveolus.

The anterior-posterior length of the mandible and maxilla are obtained clinically or radiographically. On the mandible, the measurement is specifically the distance from the midline anterior-most aspect of the alveolus to the line marking posterior transverse width, described above. On the maxilla, the measurement is specifically the distance from the midline anterior-most aspect of the alveolus to the line marking posterior transverse width, described above.

The posterior transverse width of the mandible and anterior-posterior length of the mandible are combined to give the recommended size splint, according to the sizing rubric. A practitioner may select an alternate splint size, depending on clinical and operative conditions.

The posterior transverse width of the maxilla and anterior posterior length of the maxilla are combined to give the recommended size splint, according to the sizing rubric. A practitioner may select an alternate splint size, depending on clinical and operative conditions.

These methodologies and measurements described above can also be used on an individual during fabrication of the splint itself, specifically formulation of the sizes of the splint. These measurements would be taken on a population, with the resulting data being used to formulate sizing that would accommodate a range of individuals within the population.

Use of Standardized Reduction Splint for Edentulous Patients

Once the correct maxillary and mandibular splint size has been selected, the reduction splint is taken to the operating room with the patient. It is sterilized in a conventional manner, for example with chlorhexidine or betadine in the standard fashion, and then placed in the operative field. The patient is prepped and draped as known in the art. The necessary surgical exposure of the fractures is obtained, and the pyriform aperture of the patient is exposed using methodologies known in the art. The maxillary and mandibular splints are applied in anatomic position to evaluate fit and finalize decisions regarding operative incisions and exposure.

Figure 14A:
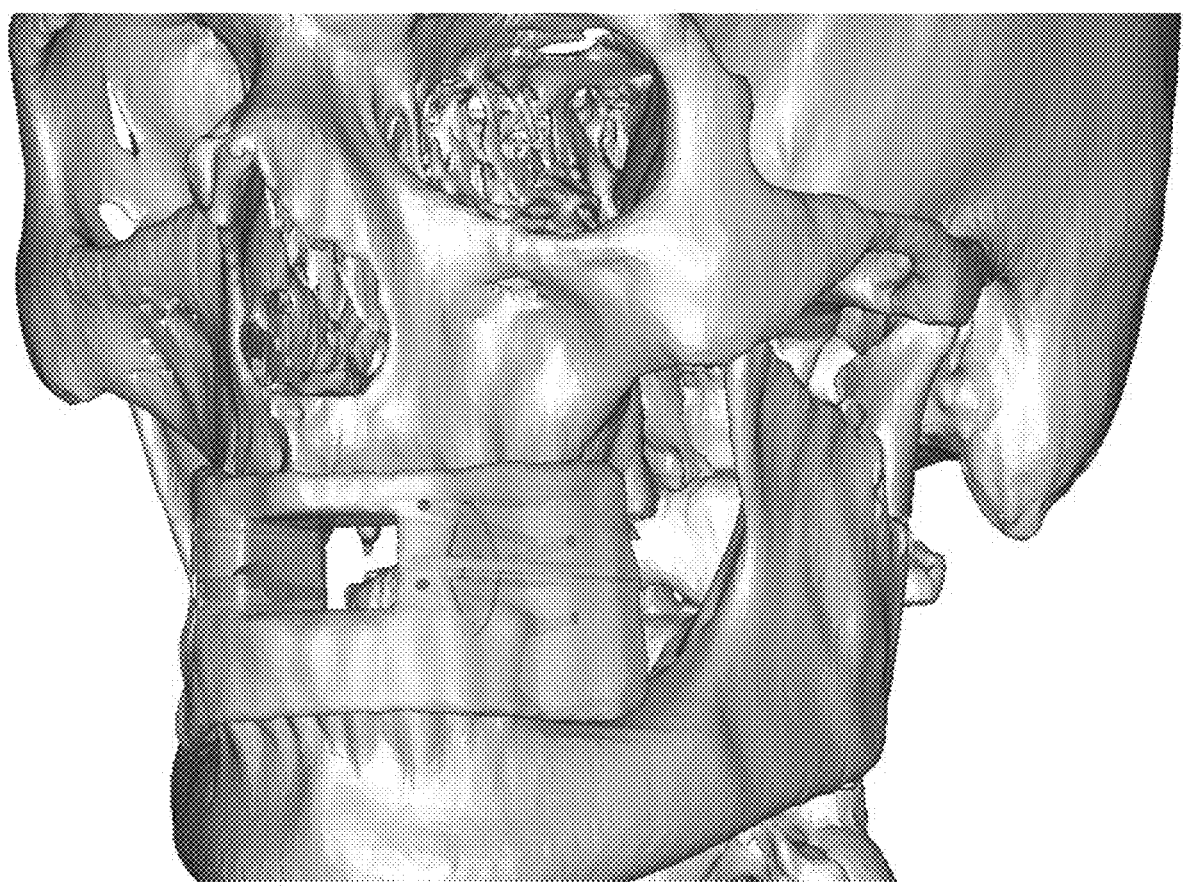
FIG. 14A is a perspective view of an application of an oral splint—resulting from an exemplary methodology according to an embodiment of the current invention—on a human jaw.
Figure 14B:
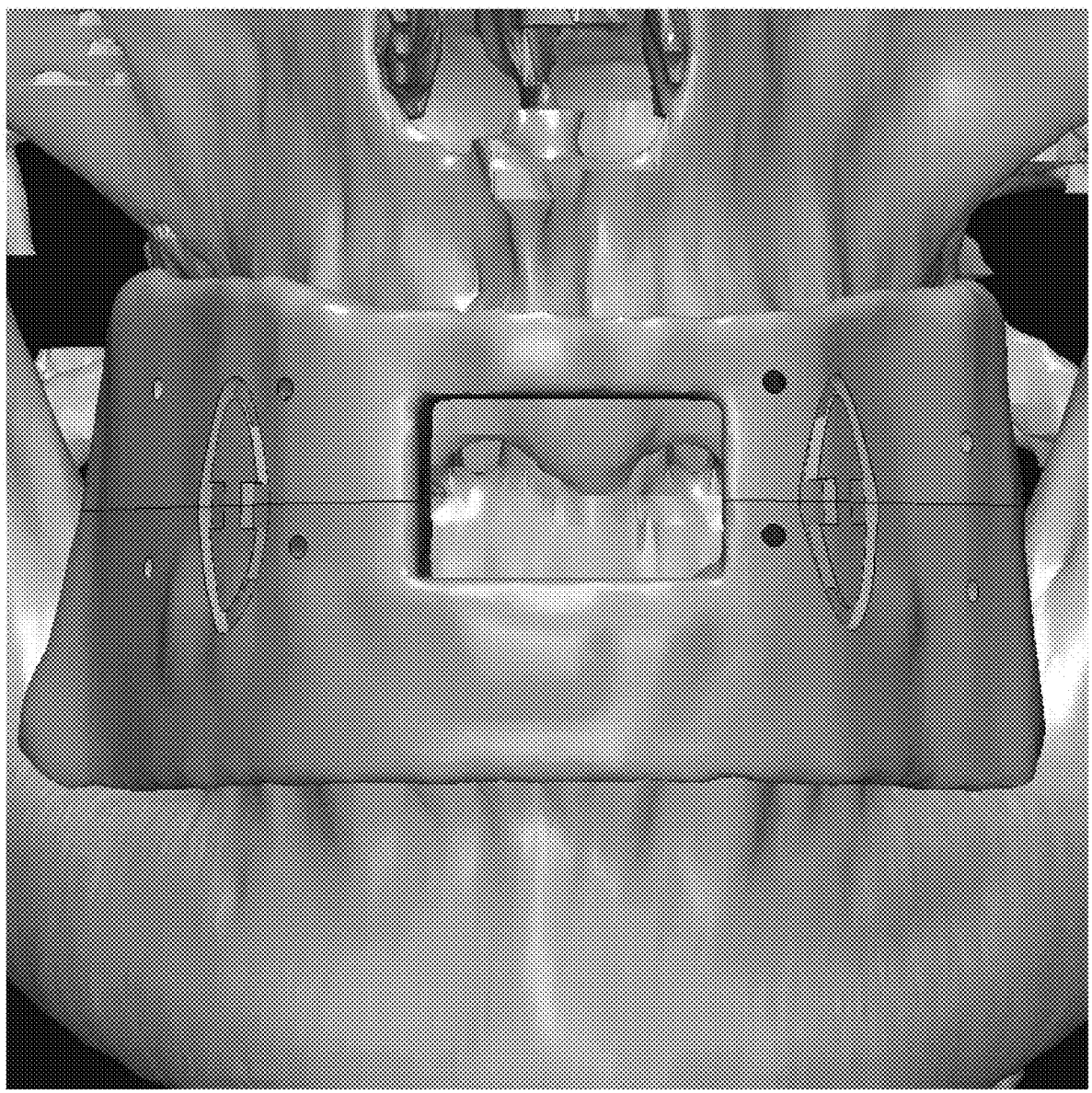
FIG. 14B is a close-up front view of the oral splint of FIG. 14A.
Figure 14C:
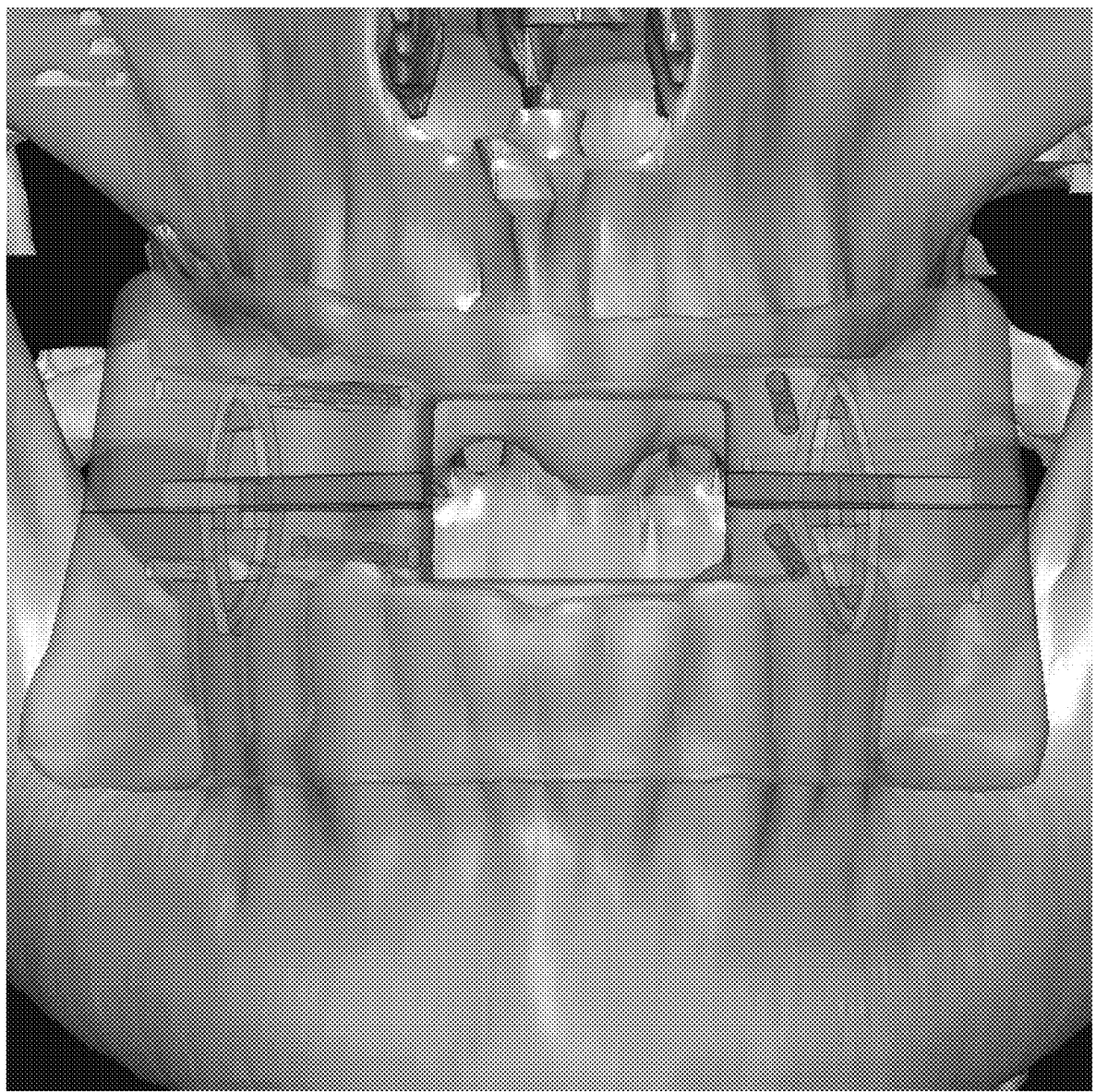
FIG. 14C depicts transparency within the view of FIG. 14B.
Figure 14D:
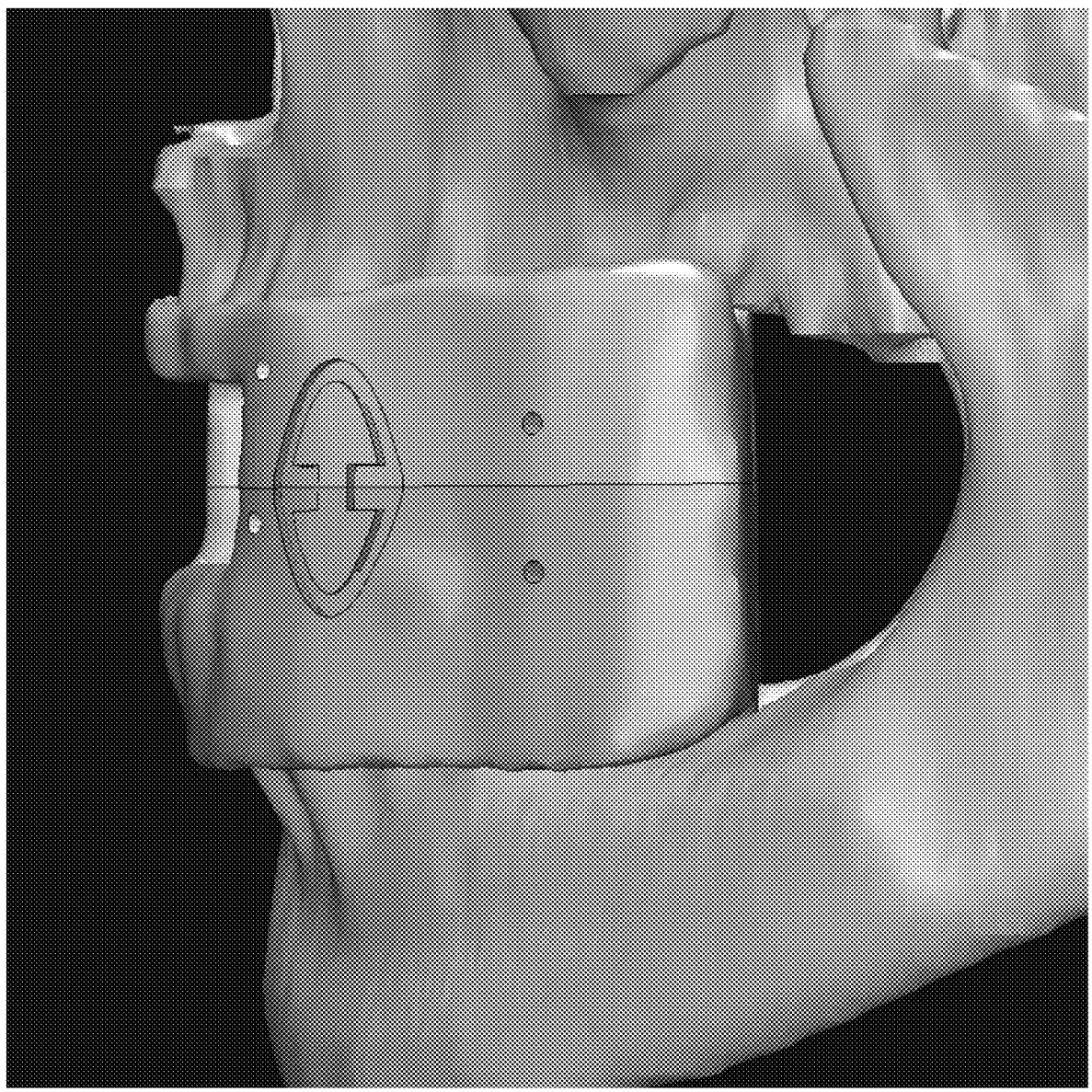
FIG. 14D is a close-up side view of the oral splint of FIG. 14A.
Figure 14E:
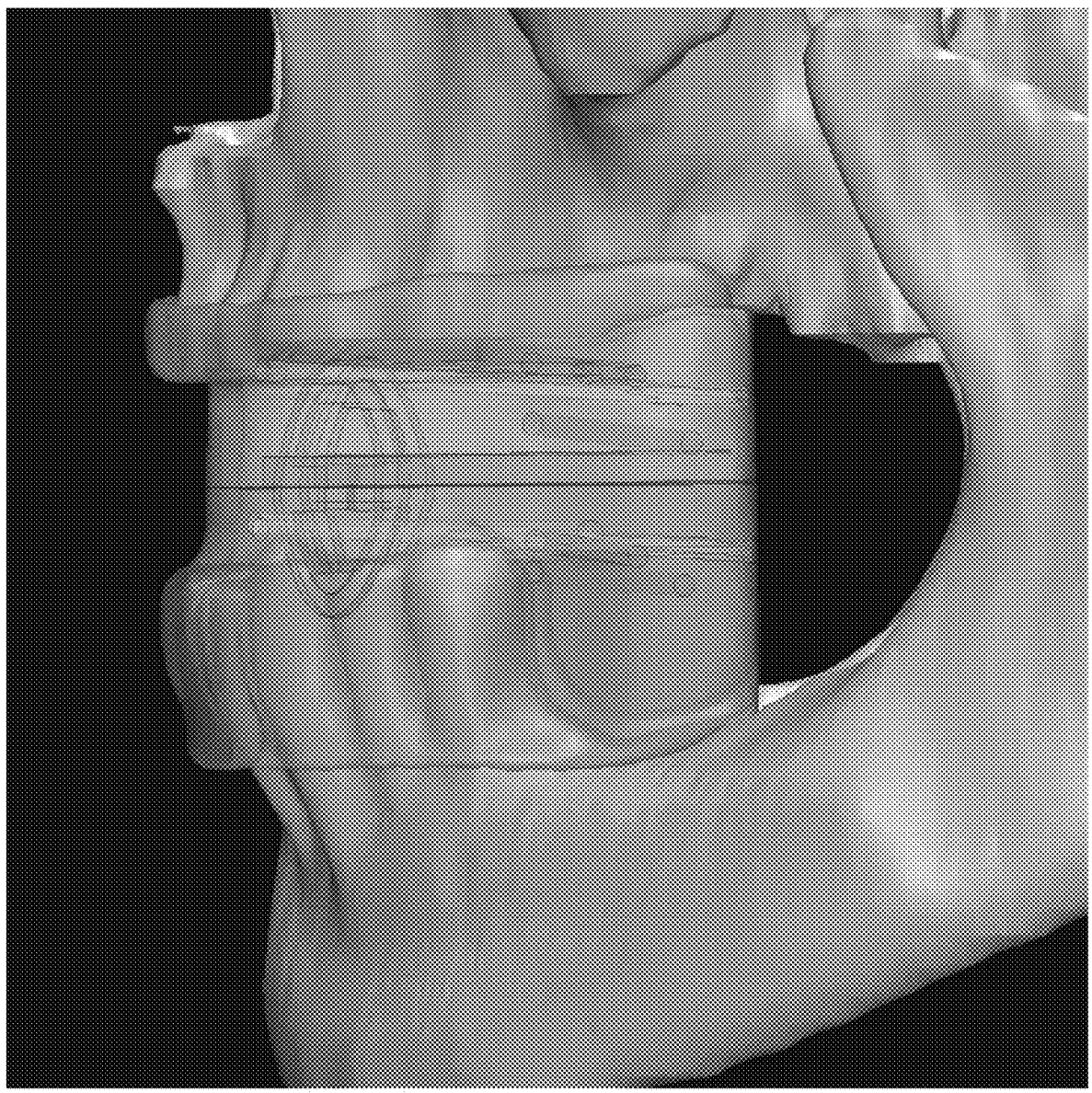
FIG. 14E depicts transparency within the view of FIG. 14D.

As the alveolar ridge and dentition are positioned with the splint into their reduced fracture position, as seen in FIG. 14A, the associated maxillary and/or mandibular fractures can reduce as well, depending on the location and severity of the fractures. To perform this, the maxillary or mandibular splint can be applied/secured first, and the remaining splint can be applied/secured second. The intersplint wires can then be placed.

The maxillary splint may be secured to the patient's maxilla by a pyriform drop wire technique, transpalatal-pyriform wire, or similar suitable technique, optionally using the guide wire apertures previously described and seen in FIGS. 9A-9B. A 24-gauge wire can be utilized for either technique, though it can be appreciated that any suitable mechanism can be used. The splint may be removed for initial wire placement to assist with visualization, and subsequently reapplied before tying the wires.

For placing a pyriform drop wire, a 1-mm drill hole can be made approximately 4-5 mm laterally to the inferolateral aspect of the pyriform aperture. The wire is then fed through the drill hole and out the pyriform aperture. The medial wire end is then placed through the anterior opening of the splint and then through the anterior ipsilateral splint hole (passed posterior to anterior), exiting anteriorly from the splint hole. This technique is then repeated on the contralateral side. The medial wire end, now through the splint hole, and the remaining free lateral pyriform wire end are then tied in a conventional manner. The contralateral wires are then similarly tied as well.

Instead of a pyriform drop wire, a transpalatal-pyriform wire may be placed to secure the maxillary splint. For the transpalatal-pyriform wire, a standard awl is used. The awl is placed with steady, firm pressure to the left or right anterior palate, aiming at the base of the ipsilateral pyriform aperture. Once the awl passes through the anterior palate and into the pyriform aperture, the wire is inserted into the awl's terminal hole, and the awl is retracted into the mouth, pulling the wire with it. The same procedure is repeated on the contralateral side. The splint it positioned anatomically, and then the wires are tied over the splint, tightly securing it to the maxilla.

It can be appreciated by one of ordinary skill in the art that the current invention contemplates other suitable methodologies of securing the maxillary splint to the maxilla as well, as would be known in the art.

To secure the mandibular splint to the patient's mandible, optionally using the guide wire apertures previously described and seen in FIGS. 9A-9B, an awl can be used in a conventional manner to position four circummandibular wires, one anterior and one posterior on each side. The lingual wire end of each circummandibular wire is then fed from posterior to anterior through the corresponding mandibular splint holes. The splint is positioned anatomically, and the lingual and buccal wire ends of each circummandibular wire are then tied in a conventional manner, thus securing the splint tightly to the mandible.

It can be appreciated by one of ordinary skill in the art that the current invention contemplates other suitable methodologies of securing the mandibular splint to the mandible as well, as would be known in the art.

With both the maxillary splint and the mandibular splint secured to the maxilla and mandible, respectively, the maxillary and mandibular splints can be secured to one another, for example by intersplint wires tied around the projections on the anterior surface of the splint, as previously described and seen in FIGS. 12A-12F. Standard 24-gauge or similar wire loops can be utilized. The recessed, oval-shaped projections spanning the maxillary and mandibular splints are lassoed with the wire loop, as seen in FIG. 12F. The wire loop is then tightened in the standard fashion around the recessed projection, one on each side of the central evacuation aperture.

The maxillary and mandibular splints may be further stabilized together in any particular manner, for example the tongue-and-groove mechanism/fitting as previously described and seen in FIGS. 11A-11D.

Additional wires may be placed at the discretion of the surgeon or operating team. The splints may be drilled with a standard drill bit or k-wire, using a steady hand and irrigation to minimize thermal damage to the surrounding splint material.

No mandibular incisions are required for splint placement if the patient has at least a majority of his/her teeth. This contrasts conventional technology where mandibular incisions are necessary in all cases with unstable mandibular fractures, regardless of how many teeth the patient possesses. However, incisions may be required with the current methodology if additional fracture fixation is indicated, specifically near the posterior portion of the mandible.

For maxillary splint placement, only two (2) limited maxillary buccal sulcus incisions are utilized to provide visualization of the pyriform aperture. These incisions may be closed with conventional techniques after the intersplint wires are positioned to secure the maxillary and mandibular splints to one another.

In an emergency situation, the intersplint wires can be cut easily to allow access to the patient's mouth and/or airway, though fracture reduction or posterior mandibular height may be lost. The patient can carry wire cutters in an accessible location, should there be a need for someone else to cut the patient's wires to release the splint. The intersplint wires can be reapplied without sedation, as long as the patient can tolerate the tongue-and-groove realignment of the maxillary and mandibular splints and as long as the maxillary and mandibular splints remain secure in an anatomic position.

Optionally, depending on the treatment plan decided on by the operating surgeon, the intersplint wires may be intentionally cut and elastics positioned around the recessed projections to provide a limited range of motion.

For removal of the reduction splint, the pyriform and circummandibular wires are cut at the level of the mucosa, and the wires are removed. Care should be taken to limit the tracking of oral contents through the wire tunnel as the wires are removed. The maxillary and mandibular splints are then easily removed. The empty wire tunnel does not need to be sutured, but it can be left to heal secondarily.

Standard operative techniques to reduce infection risk still apply, such as, but not limited to, irrigation, pre-operative/post-operative antibiotics, and routine oral hygiene procedures.

Non-Limiting Illustrative Glossary of Terms

Anterior-posterior plane: This term is used herein to refer to an imaginary flat surface disposed in a direction between the front of the subject or patient and the back of the subject or patient, such that the upper face of the plane faces the cranial direction and the lower face of the plane faces the caudal direction.

Cranial-caudal direction: This term is used herein to refer to a disposition of something along a route between the head end of the body and the tail end of the body, which is typically a substantially vertical direction in a human being. On the other hand, in a four-legged animal, for example, the cranial-caudal direction can refer to a disposition between the head end of that animal and the ground on which the animal stands (rather than the actual tail end of the animal).

Dimensions: This term is used herein to refer to various measures of spatial extent of an individual's jaw or head. Examples include, but are not limited to, palate width, palate length, maxillary length, maxillary width, maxillary anterior thickness, maxillary lateral thickness, maxillary curvature, posterior maxillary height, mandibular length, mandibular width, mandibular anterior thickness, mandibular lateral thickness, mandibular curvature, and posterior mandibular height of said plurality of individuals.

Distance: This term is used herein to refer to the amount of space between the outline of the upper palate and the outline of the lower palate.

Edentulous or partially edentulous: This term is used herein to refer to a subject or patient of any age being toothless to at least some degree due to one or more teeth being loose or absent. Complete edentulism refers to the absence of all teeth, whereas partial edentulism refers to the absence one or more teeth.

Evacuation aperture: This term is used herein to refer to an opening in the front of the splint used for evacuation of oral or gastric contents from the patient as needed, thus preventing aspiration.

Imaging: This term is used herein to refer to the creation of visual representations of the interior of a body of a subject or patient. These representations can be used for medical therapy, such as oral fracture reduction as enabled by the present invention. Examples of imaging include, but are not limited to, X-ray radiography, magnetic resonance imaging, computed tomography, medical ultrasonography or ultrasound, endoscopy, elastography, tactile imaging, thermography, medical photography and positron emission tomography.

Initial splint configuration: This term is used herein to refer to a preliminary representation of the oral splint being fabricated prior to finalization of the digital image of the splint.

Intersplint wires: This term is used herein to refer to wiring that secures together a mandibular splint and a corresponding maxillary splint.

Jaw: This term is used herein to refer to the mandibular and/or maxillary bones and their associated soft tissue and dentition.

Manipulate: This term is used herein to refer to analyzing and/or transforming a first set of data into a second set of data. As used herein, this second set of data is representative of the first set of data. This manipulation can be done, for example, by calculating a mean and a standard deviation of the first set of data. This mean and standard deviation (second set of data) would then be representative of that first set of data.

Normal position: This term is used herein to refer to the anatomic arrangement of bone and dentition in a subject or patient as present prior to oral fractures.

Oral fracture: This term is used herein to refer to breaks through the mandibular or maxillary bone or dentition of a subject or patient.

Oral splint: This term is used herein to refer to a device used in the oral cavity of a subject or patient to affix the maxilla and mandible in place during oral fracture reduction.

Outline: This term is used herein to refer to sketching or creating a line or contour along the boundary of a structure, such as the upper and lower palates of a subject or patient.

Outwardly: This term is used herein to refer to a direction toward the exterior of the splint or toward the exterior of the oral cavity of the subject or patient if the splint was hypothetically in place in the oral cavity. The virtual dentition size is increased so that the fit may be loosened and the splint may be more easily applied.

Palate: This term is used herein to refer to the floor (lower palate) and/or roof (upper palate) of the subject or patient's mouth, including the bone and the associated soft tissue.

Patient population: This term is used herein to refer to a set of individuals that are representative of a larger group of individuals and from which one or more reduction splints are fabricated to accommodate at least a majority of the individuals in that population.

Realign: This term is used herein to refer to the process of rearranging structures, such as bone and dentition, of a subject or patient into a "normal" or healthy position where the structures would be in that subject or patient without fracture.

Reduced fracture position: This term is used herein to refer to an arrangement of a splint in/on a subject or patient, such that any potential fracture of the underlying bone/dentition would be aligned properly.

Representative: This term is used herein to refer to one or more entities having the same or similar properties to a larger group of entities. For example, a plurality of people can be representative of a larger group of people by having similar properties or characteristics to that larger group of people. As another example, a single jaw structure can be representative of the jaws of a larger population by being an "average" of the larger population's jaws.

Snugly fit or contain: This term is used herein to refer to lining the splint along the exterior surface of the subject or patient's dentition/bone.

Split: This term is used herein to refer to dividing a structure into two or more parts/portions along a relatively straight line through the structure.

Tongue and groove fitting: This term is used herein to refer to a joint for fitting structures together, where one of the structures has a protrusion and the other structure has a channel in which the protrusion fits.

Wire aperture: This term is used herein to refer to a small opening allowing for the traversal of wiring that secures the mandibular splint to the mandible, the maxillary splint to the maxilla, and/or the mandibular splint to the maxillary splint.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of fabricating an oral splint for reduction of an oral fracture in an edentulous or partially edentulous subject or patient, comprising:

scanning or imaging a jaw of each of a plurality of individuals in a patient population to determine an array of dimensions of said jaws of said plurality of individuals;

manipulating said array of dimensions to generate a representative set of dimensions that is representative of a subset of said patient population;

importing results of said manipulation into one or more software applications that creates an image of a jaw representative of said subset of said patient population, said representative jaw including a maxilla and a mandible;

outlining an upper palate of said representative jaw on said one or more software applications;

outlining a lower palate of said representative jaw on said one or more software applications;

interpolating a distance between said outline of said upper palate and said outline of said lower palate on said one or more software applications;

indicating said distance as an initial splint configuration on said one or more software applications;

removing bone and dentition of said maxilla and said mandible from said image of said representative jaw on said one or more software applications; and splitting said initial splint configuration into a maxillary splint and a mandibular splint on said one or more software applications, thus forming a virtual image of said oral splint, wherein said oral splint is fabricated physically based on said virtual image of said oral splint.

2. A method as in claim 1, wherein said array of dimensions includes two or more of palate width, palate length, maxillary length, maxillary width, maxillary anterior thickness, maxillary lateral thickness, maxillary curvature, posterior maxillary height, mandibular length, mandibular width, mandibular anterior thickness, mandibular lateral thickness, mandibular curvature, and posterior mandibular height of said plurality of individuals.

3. A method as in claim 1, wherein said array of dimensions is manipulated by determining a mean value and a standard deviation of each of said array of dimensions of said jaws of said plurality of individuals.

4. A method as in claim 1, further comprising:
tessellating said maxilla and said mandible into a three-dimensional model after importing said results of said determination into said one or more software applications.

5. A method as in claim 1, further comprising:
expanding said initial splint configuration outwardly to snugly fit or contain said maxilla and said mandible.

6. A method as in claim 1, further comprising:
forming an evacuation aperture in an anterior portion of said initial splint configuration, wherein an upper portion of said evacuation aperture is disposed in said anterior portion of said maxillary splint and a lower portion of said evacuation aperture is disposed in said anterior portion of said mandibular splint.

7. A method as in claim 1, further comprising:
the step of splitting said initial splint configuration performed by positioning an anterior-posterior plane within a midsection of said initial splint configuration, wherein the position of said plane in a cranial-caudal direction is based on averaged dimensions of said patient population, and
separating said maxillary splint and said mandibular splint along said plane.

8. A method as in claim 1, further comprising:
disposing an extrusion on one of a superior surface of said mandibular splint or an inferior surface of said maxillary splint on said one or more software applications;
disposing a channel in the other of said superior surface of said mandibular splint or said inferior surface of said maxillary splint that did not receive said extrusion on said one or more software applications, wherein a position of said channel corresponds to a position of said extrusion,
said extrusion and said channel forming a tongue and groove fitting between said maxillary splint and said mandibular splint.

9. A method as in claim 8, further comprising:
said extrusion being U-shaped along a jaw line of said representative image, and
said channel being U-shaped along said jaw line of said representative image.

10. A method as in claim 1, further comprising:
forming a plurality of wire apertures in said maxillary splint and said mandibular splint to accommodate wiring to secure said maxillary splint to said maxilla and to accommodate wiring to secure said mandibular splint to said mandible.

11. A method as in claim 1, further comprising:
disposing a first maxillary projection and a second maxillary projection on said maxillary splint; and
disposing a first mandibular projection and a second mandibular projection on said mandibular splint,
wherein said first maxillary projection and said first mandibular projection are aligned with each other, and
wherein said second maxillary projection and said second mandibular projection are aligned with each other.

12. A method as in claim 1, further comprising:
said oral splint being fabricated physically by transmitting said virtual image to a three-dimensional printer for printing of said oral splint.

13. A method as in claim 1, further comprising:
trimming or filing an upper edge or a lower edge of said initial splint configuration to better fit said jaw of said subject or patient.

14. A method as in claim 1, further comprising:
prior to outlining said upper and lower palates, positioning a spacer on said maxilla or said mandible on said one or more software applications in order to provide proper spacing within said representative jaw of said patient population.

15. A surgical technique for reduction of an oral fracture in an edentulous or partially edentulous subject or patient, comprising:

scanning or imaging a jaw of each of a plurality of individuals in a patient population to determine an array of dimensions of said jaws of said plurality of individuals;

manipulating said array of dimensions to generate a representative set of dimensions that is representative of a subset of said patient population;

importing results of said manipulation into one or more software applications that creates an image of a jaw representative of said subset of said patient population, said representative jaw including a maxilla and a mandible;

outlining an upper palate of said representative jaw on said one or more software applications;

outlining a lower palate of said representative jaw on said one or more software applications;
interpolating a distance between said outline of said upper palate and said outline of said lower palate on said one or more software applications;
indicating said distance as an initial splint configuration on said one or more software applications;
removing bone and dentition of said maxilla and said mandible from said image of said representative jaw on said one or more software applications; and
splitting said initial splint configuration into a maxillary splint and a mandibular splint on said one or more software applications, thus forming a virtual image of said oral splint;
fabricating said oral splint based on said virtual image of said oral splint;
positioning and securing said maxillary splint of said fabricated oral splint on said maxilla of said subject or patient in a normal or reduced fracture position of said maxilla; and
positioning and securing said mandibular splint of said fabricated oral splint on said mandible of said subject or patient in a normal or reduced fracture position of said mandible.

16. A surgical technique as in claim 15, further comprising:
the step of fabricating said oral splint based on said virtual image of said oral splint performed by transmitting said virtual image to a three-dimensional printer for printing of said oral splint.

17. A surgical technique as in claim 15, further comprising:
the step of securing said maxillary splint on said maxilla of said subject or patient performed by a mechanism selected from the group consisting of a pyriform drop wire and transpalatal-pyriform wire.

18. A surgical technique as in claim 15, further comprising:
the step of securing said mandibular splint on said mandible of said subject or patient with circummandibular wires performed by utilizing an awl.

19. A surgical technique as in claim 18, further comprising:
disposing a first maxillary projection and a second maxillary projection on said maxillary splint;
disposing a first mandibular projection and a second mandibular projection on said mandibular splint,
wherein said first maxillary projection and said first mandibular projection are aligned with each other,
wherein said second maxillary projection and said second mandibular projection are aligned with each other; and
securing said maxillary splint and said mandibular splint together via intersplint wires wrapped around said first maxillary projection and said first mandibular projection and also around said second maxillary projection and said second mandibular projection.

20. A surgical technique as in claim 15, further comprising:
trimming or filing an upper edge or a lower edge of said initial splint configuration to better fit said jaw of said subject or patient.

* * * * *